(12) United States Patent
Melander et al.

(10) Patent No.: US 9,351,491 B2
(45) Date of Patent: May 31, 2016

(54) INHIBITION AND DISPERSION OF BIOFILMS IN PLANTS WITH IMIDAZOLE-TRIAZOLE DERIVATIVES

(71) Applicant: North Carolina State University, Raleigh, NC (US)

(72) Inventors: Christian Melander, Raleigh, NC (US); John Cavanagh, Cary, NC (US); David F. Ritchie, Durham, NC (US); Steven A. Rogers, Raleigh, NC (US); Robert W. Huigens, III, Apex, NC (US); Catherine S. Reed, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 110 days.

(21) Appl. No.: 13/946,523

(22) Filed: Jul. 19, 2013

(65) Prior Publication Data

US 2013/0315874 A1 Nov. 28, 2013

Related U.S. Application Data

(63) Continuation of application No. 13/132,979, filed as application No. PCT/US2009/066979 on Dec. 7, 2009, now abandoned.

(60) Provisional application No. 61/120,661, filed on Dec. 8, 2008.

(51) Int. Cl.
| | | |
|---|---|---|
| *A01N 43/647* | (2006.01) | |
| *A01N 63/00* | (2006.01) | |
| *A01N 59/20* | (2006.01) | |
| *A01N 43/653* | (2006.01) | |
| *C07D 403/06* | (2006.01) | |

(52) U.S. Cl.
CPC ............ *A01N 43/647* (2013.01); *A01N 43/653* (2013.01); *A01N 59/20* (2013.01); *A01N 63/00* (2013.01); *C07D 403/06* (2013.01)

(58) Field of Classification Search
CPC ...... A01N 43/647; A01N 63/00; A01N 59/20
See application file for complete search history.

(56) References Cited

U.S. PATENT DOCUMENTS

| | | | |
|---|---|---|---|
| 3,575,929 | A | 4/1971 | Jones |
| 4,514,382 | A | 4/1985 | Gaffar et al. |
| 5,358,960 | A | 10/1994 | Ulrich et al. |
| 5,670,055 | A | 9/1997 | Yu et al. |
| 5,814,668 | A | 9/1998 | Whittemore et al. |
| 5,834,411 | A | 11/1998 | Bolkan et al. |
| 6,143,774 | A | 11/2000 | Heckmann et al. |
| 7,087,661 | B1 | 8/2006 | Alberte et al. |
| 7,132,567 | B2 | 11/2006 | Alberte et al. |
| 7,160,879 | B2 | 1/2007 | DeSimone et al. |
| 7,514,458 | B2 | 4/2009 | Cogan et al. |
| 7,897,631 | B2 | 3/2011 | Melander et al. |
| 8,367,713 | B2 | 2/2013 | Melander et al. |
| 2003/0171421 | A1 | 9/2003 | Davies et al. |
| 2003/0194454 | A1 | 10/2003 | Bassette et al. |
| 2003/0196215 | A1 | 10/2003 | Olivier et al. |
| 2003/0226163 | A1 | 12/2003 | Cramer et al. |
| 2003/0229000 | A1 | 12/2003 | Merritt et al. |
| 2004/0024037 | A1 | 2/2004 | Ryu et al. |
| 2004/0235934 | A1 | 11/2004 | Fischer et al. |
| 2004/0249441 | A1 | 12/2004 | Miller et al. |
| 2005/0161859 | A1 | 7/2005 | Miller et al. |
| 2006/0018945 | A1 | 1/2006 | Britigan et al. |
| 2006/0228384 | A1 | 10/2006 | Eldridge |
| 2006/0276468 | A1 | 12/2006 | Blow |
| 2007/0033671 | A1 | 2/2007 | Jiang et al. |
| 2007/0087938 | A1 | 4/2007 | Hartfeldt |
| 2007/0142371 | A1 | 6/2007 | Cogan et al. |
| 2007/0185092 | A1 | 8/2007 | Zhu et al. |
| 2007/0231291 | A1 | 10/2007 | Huang et al. |
| 2008/0181923 | A1 | 7/2008 | Melander et al. |
| 2009/0143230 | A1 | 6/2009 | Melander et al. |
| 2009/0270475 | A1 | 10/2009 | Melander et al. |

FOREIGN PATENT DOCUMENTS

| | | | |
|---|---|---|---|
| WO | WO 2005/012263 | A1 | 2/2005 |
| WO | WO 2009/131654 | A2 * | 10/2009 |

OTHER PUBLICATIONS

International Search Report and Written Opinion, PCT/US09/66979, mailed Feb. 12, 2010.
International Search Report and Written Opinion for PCT/US08/01045, dated May 9, 2008.
Foley L and Büchi G. Biomimetic synthesis of dibromophakellin. J. Am. Chem. Soc. 1982; 104: 1776-1777.
Yamada A et al. Development of chemical substances regulating biofilm formation. Bull. Chem. Soc. Jpn. 1997; 70: 3061-3069.
Mourabit AA and Potier P. Sponge's molecular diversity through the ambivalent reactivity of 2-aminoimidazole: a universal chemical pathway to the oroidin-based pyrrole-imidazole alkaloids and their palau'amine congeners. Eur. J. Org. Chem. 2001: 237-243.

(Continued)

*Primary Examiner* — John Pak
*Assistant Examiner* — Nathan W Schlientz
(74) *Attorney, Agent, or Firm* — Myers Bigel & Sibley, P.A.

(57) ABSTRACT

Disclosure is provided for methods of preventing, removing or inhibiting microbial biofilm formation or microbial infection in a plant or plant part thereof, including applying thereto a treatment effective amount of an active compound as described herein, or an agriculturally acceptable salt thereof. Methods of enhancing a microbicide (e.g., including a copper, antibiotic, bacteriophage, etc.) and/or plant defense activator are also provided, including applying an active compound as described herein. Compositions comprising an active compound as described herein in an agriculturally acceptable carrier are also provided, and in some embodiments the compositions further include a microbicide (e.g., including copper, antibiotic, bacteriophage, etc.) and/or plant defense activator.

19 Claims, 7 Drawing Sheets

(56) References Cited

OTHER PUBLICATIONS

Hoffmann H and Lindel T. Synthesis of the pyrrole-imidazolealkaloids. Synthesis. 2003; 12: 1753-1783.
Kelly SR et al. Effects of Caribbean sponge extracts on bacterial attachment. Aquatic Microbial Ecology. Mar. 13, 2003; 31: 175-182.
Kelly SR et al. Effects of Caribbean sponge secondary metabolites on bacterial colonization. Aquatic Microbial Ecology. Sep. 6, 2005; 40: 191-203.
Musk Jr. D.J. and Hergenrother P.J. Chemical countermeasures for the control of bacterial biofilms: effective compounds and promising targets. Current Medicinal Chemistry 2006; 13: 2163-2177.
Huigens RW 3rd et al. Inhibition of pseudomonas aeruginosa biofilm formation with bromoageliferin analogues. J. Am. Chem. Soc. 2007; 129: 6966-6967.
Shore D. College Profile: Dr. John Cavanagh shows that in scientific collaboration—as in a community of molecules—the product is more powerful than the sum of its parts. Perspectives Online. North Carolina State University. Summer 2007: 4 pp.
Fishing for seafood safety. Scope. North Carolina State University College of Physical and Mathematical Sciences. Fall 2007: 11.
Ballard TE et al. Synthesis and antibiofilm activity of a second-generation reverse-amide oroidin library: a structure-activity relationship study. Chemistry. 2008; 14(34): 10745-61.
Galvin F. Marine inspiration for biofilm break up. Chemical Biology. RCS Publishing. Mar. 5, 2008: 2 pp.
Huigens RW 3rd et al. Control of bacterial biofilms with marine alkaloid derivatives. Molecular BioSystems. 2008; 4: 614-621.
Richards JJ et al. Inhibition and dispersion of Pseudomonas aeruginosa biofilms with reverse amide 2-aminoimidazole oroidin analogues. Organic & Biomolecular Chemistry. Apr. 21, 2008; 6(8): 1356-1363.
Richards JJ et al. Effects of N-pyrrole substitution on the anti-biofilm activities of oroidin derivatives against Acinetobacter baumannii. Bioorganic & Medicinal Chemistry Letters. 2008; 18: 4325-4327.
Richards JJ and Melander C. Synthesis of a 2-aminoimidazole library for antibiofilm screening utilizing the Sonogashira reaction. J. Org. Chem. 2008; 73(13): 5191-5193.
Richards JJ et al. Inhibition and dispersion of proteobacterial biofilms. Chem. Comm. 2008; 1698-1700.
Richards JJ et al. Synthesis and screening of an oroidin library against Pseudomonas aeruginosa biofilms. ChemBioChem. 2008; 9: 1267-1279.
Rogers SA and Melander C. Construction and screening of a 2-aminoimidazole library identifies a small molecule capable of inhibiting and dispersing bacterial biofilms across order, class, and phylum. Angew. Chem. Int. Ed. 2008; 47: 5229-5231.
Ballard TE et al. Antibiofilm activity of a diverse oroidin library generated through reductive acylation. J. Org. Chem. 2009; 74(4): 1755-1758.
Huigens RW 3rd et al. Inhibition of Acinetobacter baumannii, *Staphylococcus aureus* and Pseudomonas aeruginosa biofilm formation with a class of TAGE-triazole conjugates. Org. Biomol. Chem. 2009; 7: 794-802.
Melander C et al. Evaluation of dihydrooroidin as an antifouling additive in marine paint. International Biodeterioration & Biodegradation. 2009; 53: 529-532.
Rogers SA et al. Tandem dispersion and killing of bacteria from a biofilm. Organic & Biomolecular Chemistry. 2009; 7: 603-606.
Stokstad E. Sponging away antibiotic resistance. Findings. The Science Magazine News Blog. Feb. 14, 2009: 1 p.
Lydersen K. Scientists learning to target bacteria where they live. washingtonpost.com. The Washington Post. Mar. 9, 2009; A05: 3 pp.
Taking the Resistance out of drug-resistant infections. PhysOrg.com. Apr. 10, 2009: 2 pp.
Avery S. Slime-fighting molecule may rearm antibiotics. newsobserver.com. The News and Observer. Raleigh, NC. Apr. 22, 2009: 2 pp.
International Search Report and Written Opinion, PCT/US09/02101, mailed Jul. 13, 2009.
International Search Report and Written Opinion, PCT/US09/02446, mailed Aug. 31, 2009.
Casalinuovo IA et al. Fluconazole resistance in *Candida albicans*: a review of mechanisms. European Review for Medical and Pharmacological Sciences. 2004; 8(2): 69-77.
Rogers SA et al. A 2-aminobenzimidazole that inhibits and disperses gram-positive biofilms through a zinc-dependent mechanism. J. Am. Chem. Soc. 2009; 131(29): 9868-9869.
Richards JJ et al. Amide isosteres of oroidin: assessment of antibiofilm activity and *C. elegans* toxicity. Journal of Medicinal Chemistry. 2009; 52(15): 4582-4585.
Richards JJ and Melander C. Controlling bacterial biofilms. ChemBioChem. Epub ahead of print: Aug. 13, 2009; 9 pp.
Ginsburg I. The role of bacteriolysis in the pathophysiology of inflammation, infection and post-infectious sequelae. APMIS. 2002; 110: 753-770.
Salvatori M et al. Versatile access to C-4 substituted 2-amino-1,3-azoles from hydropyridines in oxidative conditions. J. Org. Chem. 2005; 70: 8208-8211.
Rice LB. Unmet medical needs in antibacterial therapy. Biochemical Pharmacology. 2006; 71: 991-995.
Canadian Paedriatric Society. Antimicrobial products in the home: The evolving problem of antibiotic resistance. Paediatrics & Child Health. 2006; 11(3): 169-173.
Breckle G et al. Document No. 139:164905 retrieved from CAPLUS on Jan. 3, 2010.
Kirk KL et al. Document No. 80:15172 retrieved from CAPLUS on Jan. 3, 2010.
Finn FM and Hofmann K. Document No. 62:66837 retrieved from CAPLUS on Jan. 3, 2010.
Rogers SA et al. Chemical synthesis and biological screening of 2-aminoimidazole-based bacterial and fungal antibiofilm agents. Chembiochem. Feb. 2010; 11: 396-410.
Rogers SA et al. Synergistic effects between conventional antibiotics and 2-aminoimidazole-derived antibiofilm agents. Antimicrob. Agents Chemother. Mar. 8, 2010: 1-34.
Wang B et al. Drug Delivery: Principles and Applications, 2005 John Wiley & Sons, Inc. Publication, Section 8.3, pp. 136-137.
Rautio J et al. Prodrugs: design and clinical applications. Nature Reviews Drug Discovery. Mar. 2008; 7: 255-270.
Smith DA. Do prodrugs deliver? Current Opinion in Drug Discovery & Development. 2007; 10(5): 550-559.
Testa B. Current Opinion in Chemical Biology. 2009; 13: 338-344.
Danhorn T and Fuqua C. Biofilm formation by plant-associated bacteria. Annu. Rev. Microbio. (2007). vol. 61, pp. 401-422.
Walker TS et al. Pseudomonas aeruginosa—plant root interactions. Plant Physiology. Jan. 2004; 134: 320-331.
Fux CA et al. Bacterial biofilms: a diagnostic and therapeutic challenge. Expert Review of Anti-infective Therapy. Dec. 2003, vol. 1, No. 4 : pp. 667-683.

* cited by examiner

INHIBITION AND DISPERSION OF BIOFILMS IN PLANTS WITH IMIDAZOLE-TRIAZOLE DERIVATIVES

RELATED APPLICATIONS

This application is a continuation of application Ser. No. 13/132,979, which application has a 371(c) date of Aug. 16, 2011, as a national phase entry of PCT Application PCT/US2009/066979, filed Dec. 7, 2009, and published in English on Jul. 8, 2010, as International Publication No. WO 2010/077603, which claims the benefit under 35 U.S.C. §119(e) of U.S. Application No. 61/120,661, filed Dec. 8, 2008 the disclosure of each of which is incorporated herein by reference in its entirety. This application is related to U.S. application Ser. No. 12/426,742, filed Apr. 20, 2009, and published Oct. 22, 2009, as publication no. 2009/0263438, now U.S. Pat. No. 7,897,631, the disclosure of which is incorporated herein by reference in its entirety.

FIELD OF THE INVENTION

This invention relates to compositions and methods useful for controlling biofilms and microorganisms in plants, particularly vascular plants.

BACKGROUND OF THE INVENTION

New approaches are urgently needed to improve agricultural production, given the steadily growing global population that is predicted to reach 6-9 billion persons by mid-century, the continual strain on existing and finite agricultural lands, and the recent diversion of valuable agricultural land from production of crops to production of biomass for fuels. Here we describe new approaches to increase agricultural production by controlling the adverse effects of microorganisms on plants.

The five main crops on which modern societies depend most heavily include corn, cotton, rice, soybeans, and wheat. All of these crops are affected in a deleterious manner by biofilm formation. In addition, other valuable plants such as those producing fruits and vegetables are similarly affected. Plants grown for biomass stand to increase as a valuable crop, albeit not for food, and also can benefit from protection from biofilm formation. Forestry crops and ornamentals also suffer from biofilms.

SUMMARY OF THE INVENTION

The present invention is a method of preventing, removing or inhibiting microbial biofilm formation or microbial infection in a plant or plant part thereof, comprising applying to the plant or plant part a treatment effective amount of a compound selected from the group consisting of compounds of Formula (I), Formula (I)(a)(1), Formula (I)(b)(1), Formula (I)(a)(2), Formula (I)(b)(2), Formula (I)(i), Formula (I)(i)(a), Formula (II), Formula (II)(a), Formula (II)(i), Formula (II)(i)(a), Formula (III), Formula (III)(a), Formula (III)(b), Formula (III)(b)(i), Formula (III)(b)(ii), Formula (IV), Formula (IV)(a), Formula (IV)(i), Formula (IV)(i)(a), Formula (V), Formula (V)(a), Formula (V)(i), Formula (V)(i)(a), Formula (VI), Formula (VI)(a), Formula (VI)(i) and Formula (VI)(i)(a) as described herein, or an agriculturally acceptable salt thereof.

In some embodiments, the plant is a fruit or a vegetable crop plant.

In some embodiments, the plant is a citrus tree, and the compound is applied in an amount effective to treat or control a bacterial disease selected from the group consisting of canker, bacterial spot, Black Pit (fruit), Blast, citrus variegated chlorosis, and Citrus Huanglongbing. In some embodiments, the citrus tree is selected from the group consisting of orange, grapefruit, Mandarin, lemon, lime and Kumquat.

In some embodiments, the plant is a pome fruit, and the compound is applied in an amount effective to treat or control a bacterial disease selected from the group consisting of Fire Blight, Crown Gall, Blister spot and Hairy root. In some embodiments, the pome fruit is selected from the group consisting of apple, pear, quince, Asian pear, and loquats.

In some embodiments, the plant is a *Musa* species such as a banana, and the compound is applied in an amount effective to treat or control *Ralstonia solanacearum*.

In some embodiments, the plant is a cole (Brassicaceae) such as cabbage or broccoli, and the compound is applied in an amount effective to treat or control black rot (*Xanthononas campestris*).

In some embodiments, the plant is a winegrape, and the compound is applied in an amount effective to treat or control for Pierce's disease (*Xylella fastidosa*) or crown gall (*Agrobacterium vitas, A. tumefaciens*).

In some embodiments, the plant is a stone fruit or nut (e.g., peaches, nectarines, plums, almonds, walnuts), and the compound is applied in an amount effective to treat or control bacterial spot and/or blight caused by *Xanthomonas arboricola*; blight caused by *Pseudomonas syringae*); crown gall caused by *Agrobacterium tumefaciens*; phony peach and plum; or almond leaf scorch caused by *Xylella fastidosa*.

In some embodiments, the plant is a landscape and/or shade tree (e.g., oak, maple, birch, etc.) for bacterial leaf scorch disease (e.g., cause by *Xylella fastidosa*).

In some embodiments, the plant is a potato, and the compound is applied in an amount effective to treat or control soft rot or black leg (*Erwinia, Pectobacterium*).

In some embodiments, the plant is a pepper plant, and the compound is applied in an amount effective to treat or control a bacterial disease selected from the group consisting of Bacterial Spot, Bacterial wilt, Bacterial canker, and Syringae seedling blight and leaf spot.

In some embodiments, the plant is a tomato plant, and the compound is applied in an amount effective to treat or control a bacterial disease selected from the group consisting of: bacterial canker, bacterial speck, bacterial spot, bacterial stem rot and fruit rot, Bacterial wilt, Pith necrosis, and Syringae leaf spot.

In some embodiments, the plant is a soybean plant, and the compound is applied in an amount effective to treat or control a bacterial disease selected from the group consisting of Bacterial blight, Bacterial pustules, Bacterial wilt, Bacterial crinkle leaf, Bacterial tan spot, and Wildfire.

In some embodiments, the plant is corn, and the compound is applied in an amount effective to treat or control a bacterial disease selected from the group consisting of: Bacterial leaf blight, stalk rot, bacterial stripe, chocolate spot, *holcus* spot all causes by *Pseudomonas* species, Bacterial leaf spot caused by *Xanthomomas* species, Bacterial stalk rot, top rot and Stewart's disease caused by *Erwinia* species, seed rot-seedling blight caused by *Bacillus* species, Purple leaf sheath caused by *Hemiparasitic* bacteria, Corn stunt caused by *Spriroplasma kunkelii*, Goss's bacterial wilt and blight caused by *Clivibacter michiganensis*.

In some embodiments, the plant is cotton, and the compound is applied in an amount effective to treat or control a bacterial disease selected from the group consisting of Bacterial blight caused by *Xanthomonas* species, and Crown gall caused by *Agrobacterium* species and Lint degradation caused by *Erwinia* species.

In some embodiments, the plant is wheat, and the compound is applied in an amount effective to treat or control a bacterial disease selected from the group consisting of Bacterial leaf blight, bacterial sheath rot and Basal glume rot caused by *Pseudomonas* species, Bacterial mosaic and Spike blight caused by *Clavibacter* species, Black chaff caused by *Xanthomonas* species, and Pink seed caused by *Erwinia* (Pantoea) species.

In some embodiments, the plant is rice, and the compound is applied in an amount effective to treat or control a bacterial disease selected from the group consisting of bacterial blight and leaf streak caused by *Xanthomonas* species, Foot rot caused by *Erwinia* species, Grain rot caused by *Burkholderia* species, and Sheath brown rot caused by *Pseudomonas* species.

In some embodiments, the plant is pineapple, and the compound is applied in an amount effective to treat or control a bacterial disease selected from the group consisting of bacterial heart rot, fruit collapse, bacterial fruitlet brown rot, marbled fruit, pink fruit and soft rot caused by *Erwinia* species, and Acetic souring caused by Acetic acid bacteria.

In some embodiments, the microbial biofilm formation or microbial infection is caused by a fungi. In some embodiments, the compound is applied to the plant in an amount effective to treat or control a fungal disease selected from the group consisting of rots, leaf molds, blights, wilts, damping-off, spot, root rot, stem rot, mildew, brown spot, gummosis, melanose, post-bloom fruit drop, scab, *alternaria*, canker, flyspeck, fruit blotch, dieback, downy mildews, ear rots, anthracnose bunts, smut, rust, eyespot and pecky rice.

In some embodiments, the plant is citrus, and the compound is applied in an amount effective to treat or control a fungal disease selected from the group consisting of: *Alternaria* brown spot caused by *Alternaria alternaria*, Brown rot caused by *Phytophtora citricola*, Greasy spot and Greasy spot rind blotch caused by *Mycosphaerella citri*, Melanose caused by *Diaporthe citri*, *Phytophthora* foot rot, gummosis and root rot caused by *Phytophthora citrophthora*, *Phytophthora palmivora*, *Phytophthora syringae* and other *Phytophthora* spp, Post bloom fruit drop caused by *Colletotrichum acutatum*, and Scab caused by *Elsinoe fawcettii*.

In some embodiments, the plant is Pome fruit, and the compound is applied in an amount effective to treat or control a fungal disease selected from the group consisting of: Apple scab caused by *Venturia inaequalis*, Bitter rot caused by *Colletotrichum gloeosporioides*, Diplodia canker caused by *Dilpodia mutila*, *Phytophthora* crown, collar, root and fruit rot caused by *Phytophthora* spp., Powdery mildew caused by *Podosphaera leucotricha*, Pacific Coast pear rust, Cedar apple rust, Quince rust caused by *Gymnosporangium* spp., and Flyspeck caused by *Schizothyrium pomi*.

In some embodiments, the plant is Peppers, and the compound is applied in an amount effective to treat or control a fungal disease selected from the group consisting of: Anthracnose caused by *Colletotrichum* spp., Damping-off and root rot caused by *Rhizoctonia solani*, *Phytophthora* spp., *Fusarium* spp., and *Pythium* spp., *Phytophthora* blight caused by *Phytophthora capsici*, and *Verticillium* wilt caused by *Verticillium albo-atrium*.

In some embodiments, the plant is Tomato, and the compound is applied in an amount effective to treat or control a fungal disease selected from the group consisting of: *Alternaria* stem canker caused by *Alternaria alternaria*, Anthracnose caused by *Colletotrichum* spp., *Fusarium* crown, root rot and wilt caused by *Fusarium oxysporum*, Gray mold caused by *Botrytis cinerea*, Late blight caused by *phytophthora infestans*, *Pythium* damping-off and fruit rot caused by *Pythium* spp., *Rhizoctonia* damping-off and fruit rot caused by *Rhizoctonia solani*, *Septoria* leaf spot caused by *Septoria lycopersici*, *Verticillium* wilt caused by *Verticillium albo-atrum*, and White mold caused by *Sclerotinia sclerotiorum*.

In some embodiments, the plant is Soybean, and the compound is applied in an amount effective to treat or control a fungal disease selected from the group consisting of: *Phytophthora* root and stem rot caused by *Phytophthora sojae*, *Pythium* root rot, damping-off and seed decay caused by *Pythium* spp., Brown stem rot caused by *Phialophora gregata*, *Rhizoctonia* root and stem rot caused by *Rhizoctonia solani*, Stem canker, pod and stem blight caused by *Diaporthe phaseolorum*, *Phomopsis* seed decay caused by *Phomopsis longicolla*, Charcoal rot caused by *Macrophomina phaseolina*, *Sclerotinia* stem rot caused by *Sclerotinia sclerotiorum*, Sudden death syndrome caused by *Fusarium solani*, and Soybean Rust caused by *Phakopsora pachyrhizi*.

In some embodiments, the plant is Grape, and the compound is applied in an amount effective to treat or control a fungal disease selected from the group consisting of: *Alternaria* rot caused by *Alternaria alternaria*, Angular leaf spot caused by *Mycosphaerella angulata*, *Botrytis* bunch rot and blight caused by *Botrytis cinerea*, *Diplodia* cane dieback and bunch rot caused by *Diplodia natalensis*, Downy mildew caused by *Plasmopara viticola*, *Phytophthora* crown and root rot caused by *Phytophthora* spp., Powdery mildew caused by *Uncinula necator*, Ripe rot caused by *Glomerella cingulata*, *Septoria* leaf spot caused by *Septoria ampelopsidis*, and *Verticillium* wilt caused by *Verticillium dahliae*.

In some embodiments, the plant is Potato, and the compound is applied in an amount effective to treat or control a fungal disease selected from the group consisting of: Brown spot, Black pit and Early blight caused by *Alternaria* spp., *Fusarium* dry rot and wilt caused by *Fusarium* spp., Gangrene caused by *Phoma* spp., Late blight and Pink rot caused by *Phytophthora* spp., *Rhizoctonia* canker and black scurf caused by *Rhizoctonia solani*, *Rosellinia* black rot caused by *Rosellinia* spp., *Septoria* leaf spot caused by *Septoria lycopersici*, Stem rot caused by *Sclerotium rolfsii*, *Verticillium* wilt caused by *Verticillium albo-atrum*, and White mold caused by *Sclerotinia sclerotiorum*.

In some embodiments, the plant is Pineapple, and the compound is applied in an amount effective to treat or control a fungal disease selected from the group consisting of: Anthracnose caused by *Colletotrichum ananas*, Butt rot and White leaf spot caused by *Chalara paradoxa*, Leaf spot caused by *Curvularia eragrostidis*, *Phytophthora* heart rot caused by *Phytophthora cinnamomi* and *Phytophthora parasitica*, Root rot and Seedling blight caused by *Pythium* spp., and Leaking brown ring caused by *Tofflieadis dimenationa*.

In some embodiments, the plant is Cotton, and the compound is applied in an amount effective to treat or control a fungal disease selected from the group consisting of: Anthracnose caused by *Glomerella gossypii*, Boll rot caused by *Colletotrichum gossypii*, *Fusarium* spp., *Phytophthora* spp., or *Rhizoctonia solani*, *Fusarium* wilt caused by *Fusarium oxysporum*, Leaf spot caused by *Alternaria* spp., *Cercospora gossypina*, *Rhizoctonia solani*, and *Stemphylium solani*, Lint contamination caused by *Aspergillus flavus*, Powdery mildew caused by *Leveillula taurica*, Cotton rust caused by *Puccinia schedonnardii*, Southwestern cotton rust caused by *Puccinia cacabata*, Tropical cotton rust caused by *Phakopsora gossypii*, Southern blight caused by *Sclerotium rolfsii*, Seedling disease complex caused by *Colletotrichum gossypii*, Fusarium spp., Pythium spp., Rhizoctonia solani, or Thielaviopsis basicola, Stem canker caused by Phoma exigua, and Verticillium wilt caused by Verticillium dahliae.

In some embodiments, the plant is Corn, and the compound is applied in an amount effective to treat or control a fungal disease selected from the group consisting of: Anthracnose caused by Colletotrichum graminicola, Aspergillus ear and kernel rot caused by Aspergillus flavus, Banded leaf, sheath spot, root rot and stalk rot caused by Rhizoctonia solani, Brown spot, Black spot and Stalk rot caused by Physoderma maydis, Curvularia leaf spot caused by Curvularia clavata, Diplodia ear rot, stalk rot, seed rot and seedling blight caused by Dilpodia spp., Downey mildews caused by Sclerophthora spp. or Peronosclerospora spp., Ear rots caused by Alternaria alternaria, Ergot caused by Claviceps gigantea, Fusarium ear, stalk, kernel, root, seed rot, seedling blight caused by Fusarium spp., Cercospora leaf spot caused by Cercospora zeae-maydis, Helminthosporium ear rot caused by Helminthosporium carbonum, Pythium root rot and stalk rot caused by Pythium spp., Rhizoctonia ear rot caused by Rhizoctonia zeae, Common corn rust and Southern corn rust caused by Puccinia spp., Southern blight caused by Athelia rolfsii, Common smut caused by Ustilago zeae, Southern corn leaf blight and stalk rot caused by Cochliobolus heterostrophus, and storage rots caused by Aspergillus spp. and Penicillium spp.

In some embodiments, the plant is Rice, and the compound is applied in an amount effective to treat or control a fungal disease selected from the group consisting of: Black kernel caused by Curvularia lunata, Blast caused by Pyricularia oryzae, Brown spot caused by Cochliobolus miyabeanus, Downy mildew caused by Sclerophthora macrospora, False smut caused by Ustilaginoidea virens, Narrow brown leaf spot caused by Cercospora janseana, Pecky rice caused by Fusarium spp., Microdochium oryzae, or Sarocladium oryzae, Root rot caused by Fusarium spp, or Pythium spp., Seedling blight caused by fungi (e.g., Cochliobolus miyabeanus, Curvularia spp., Fusarium spp., Rhizoctonia solani, Sclerotium rolfsii and Athelia rolfsii), Stackburn caused by Alternaria padwickii, Stem rot caused by Magnaporthe salvinii, Water-mold (seed-rot and seedling disease) caused by Achlya spp., Fusarium spp., or Pythium spp.

In some embodiments, the plant is Wheat, and the compound is applied in an amount effective to treat or control a fungal disease selected from the group consisting of: Alternaria leaf blight caused by Alternaria triticina, Anthracnose caused by Colletotrichum graminicola, Black head molds caused by Cladosporium spp., Epicoccum spp., Sporobolomyces spp. or Stemphylium spp., Common bunt caused by Tilletia spp., Crown rot, seedling blight and dryland root rot caused by Fusarium spp. or Gibberella spp., Downey mildew caused by Sclerophthora macrospora, Dwarf bunt caused by Tilletia controversa, Ergot caused by Claviceps purpurea, Eyespot caused by Tapesia yallundae, Leaf rust caused by Puccinia triticina, Loose smut caused by Ustilago tritici, Microscopia leaf spot caused by Phaeosphaeria microscopia, Phoma spot caused by Phoma spp., Powdery mildew caused by Erysiphe graminis, Pythium root rot, Snow rot caused by Pythium spp., Rhizoctonia root rot caused by Rhizoctonia solani, Scab (head blight) caused by Fusarium spp. or Gibberella spp., Southern blight caused by Sclerotium rolfsii, Speckled snow mold caused by Typhula spp., Stem rust caused by Puccinia graminis, storage molds caused by Aspergillus spp. or Penicillium spp., Take-all caused by Gaeumannomyces graminis, and Zoosporic root rot caused by Lagena radicola.

A further aspect of the present invention is an agricultural composition comprising: (a) an agriculturally acceptable carrier (e.g., an aqueous carrier or a solid particulate carrier); and (b) an antimicrobial or biofilm preventing, removing or inhibiting compound selected from the group consisting of compounds of Formula (I), Formula (I)(a)(1), Formula (I)(b)(1), Formula (I)(a)(2), Formula (I)(b)(2), Formula (I)(i), Formula (I)(i)(a), Formula (II), Formula (II)(a), Formula (II)(i), Formula (II)(i)(a), Formula (III), Formula (III)(a), Formula (III)(b), Formula (III)(b)(i), Formula (III)(b)(ii), Formula (IV), Formula (IV)(a), Formula (IV)(i), Formula (IV)(i)(a), Formula (V), Formula (V)(a), Formula (V)(i), Formula (V)(i)(a), Formula (VI), Formula (VI)(a), Formula (VI)(i) and Formula (VI)(i)(a) as described herein, or an agriculturally acceptable salt thereof. In some embodiments, the composition further includes a microbicide. In some embodiments, the microbicide comprises copper (e.g., copper hydroxide). In some embodiments, the microbicide comprises an antibiotic or a bacteriophage. In some embodiments, the composition further includes a plant defense activator. In some embodiments, the composition further includes both a plant defense activator and a microbicide. In some embodiments, the compound is a compound of Formula (II)(a)(5)(D):

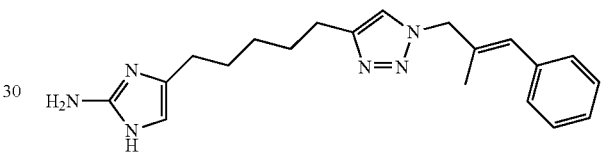

(II)(a)(5)(D)

or an agriculturally acceptable salt thereof.

Further provided are methods of enhancing the effects of a microbicide comprising applying an active compound selected from the group consisting of compounds of Formula (I), Formula (I)(a)(1), Formula (I)(b)(1), Formula (I)(a)(2), Formula (I)(b)(2), Formula (I)(i), Formula (I)(i)(a), Formula (II), Formula (II)(a), Formula (II)(i), Formula (II)(i)(a), Formula (III), Formula (III)(a), Formula (III)(b), Formula (III)(b)(i), Formula (III)(b)(ii), Formula (IV), Formula (IV)(a), Formula (IV)(i), Formula (IV)(i)(a), Formula (V), Formula (V)(a), Formula (V)(i), Formula (V)(i)(a), Formula (VI), Formula (VI)(a), Formula (VI)(i) and Formula (VI)(i)(a) as described herein, in combination with said microbicide. In some embodiments, the microbicide comprises copper (e.g., copper hydroxide). In some embodiments, the microbicide is an antibiotic or a bacteriophage. In some embodiments, the applying step is carried out by applying the active compound and the microbicide simultaneously. In some embodiments, the applying step is carried out by applying the active compound and the microbicide sequentially. In some embodiments, the compound is a compound of Formula (II)(a)(5)(D):

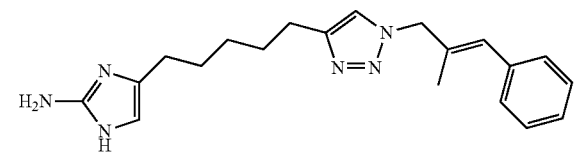

(II)(a)(5)(D)

or an agriculturally acceptable salt thereof.

Also provided are methods of enhancing the effects of a plant defense activator comprising applying an active compound selected from the group consisting of compounds of Formula (I), Formula (I)(a)(1), Formula (I)(b)(1), Formula (I)(a)(2), Formula (I)(b)(2), Formula (I)(i), Formula (I)(i)(a), Formula (II), Formula (II)(a), Formula (II)(i), Formula (II)(i)(a), Formula (III), Formula (III)(a), Formula (III)(b), Formula (III)(b)(i), Formula (III)(b)(ii), Formula (IV), Formula (IV)(a), Formula (IV)(i), Formula (IV)(i)(a), Formula (V), Formula (V)(a), Formula (V)(i), Formula (V)(i)(a), Formula (VI), Formula (VI)(a), Formula (VI)(i) and Formula (VI)(i)(a) as described herein, in combination with said plant defense activator. In some embodiments, the applying step is carried out by applying the active compound and the microbicide simultaneously. In some embodiments, the applying step is carried out by applying the active compound and the microbicide sequentially. In some embodiments, the compound is a compound of Formula (II)(a)(5)(D):

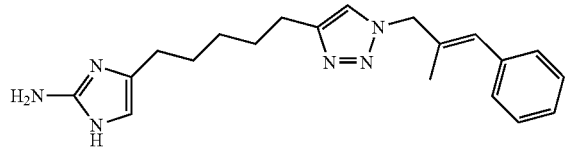

(II)(a)(5)(D)

or an agriculturally acceptable salt thereof.

A further aspect of the present invention is an antimicrobial or biofilm preventing, removing or inhibiting compound selected from the group consisting of compounds of Formula (I), Formula (I)(a)(1), Formula (I)(b)(1), Formula (I)(a)(2), Formula (I)(b)(2), Formula (I)(i), Formula (I)(i)(a), Formula (II), Formula (II)(a), Formula (II)(i), Formula (II)(i)(a), Formula (III), Formula (III)(a), Formula (III)(b), Formula (III)(b)(i), Formula (III)(b)(ii), Formula (IV), Formula (IV)(a), Formula (IV)(i), Formula (IV)(i)(a), Formula (V), Formula (V)(a), Formula (V)(i), Formula (V)(i)(a), Formula (VI), Formula (VI)(a), Formula (VI)(i) and Formula (VI)(i)(a) as described herein, for use in treating or preventing a bacterial or fungal infection in a plant or plant part as described above and below.

DETAILED DESCRIPTION OF THE PREFERRED EMBODIMENTS

Figure 1:
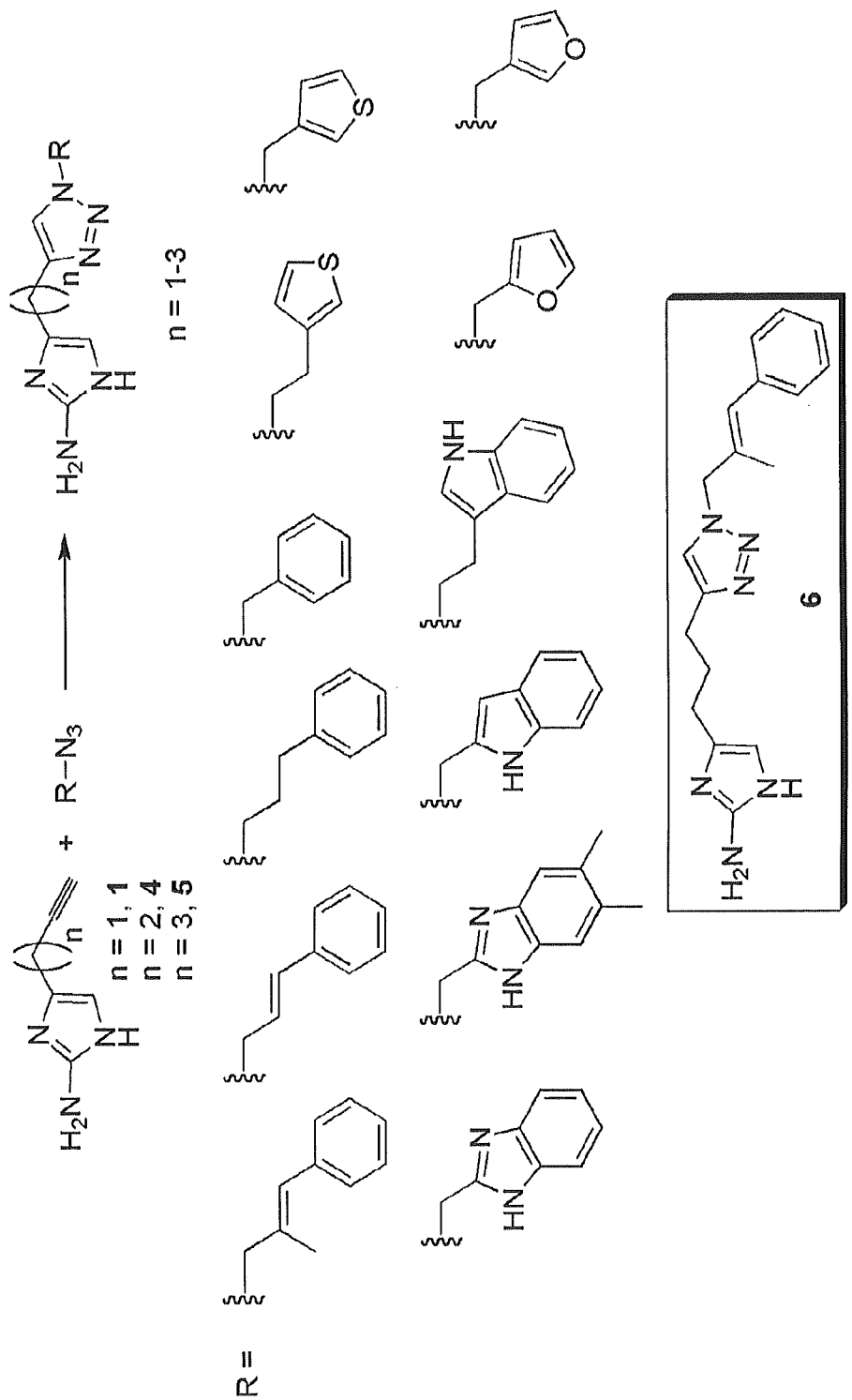
FIG. 1. Construction of the initial 2-AIT library.
Figure 2:
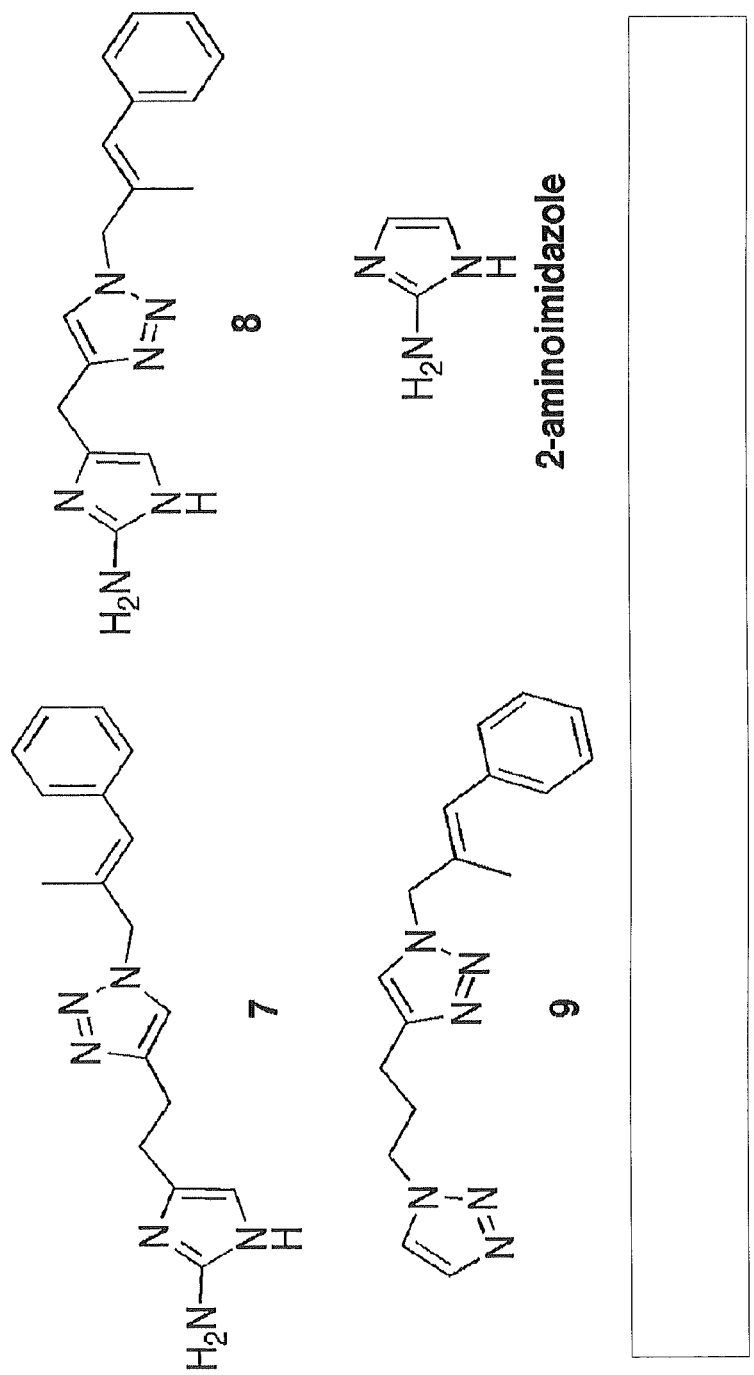
FIG. 2. Variation on tether length.
Figure 3:
FIG. 3. Effects of bacterial spot disease on pepper plants and crops.
Figure 4:
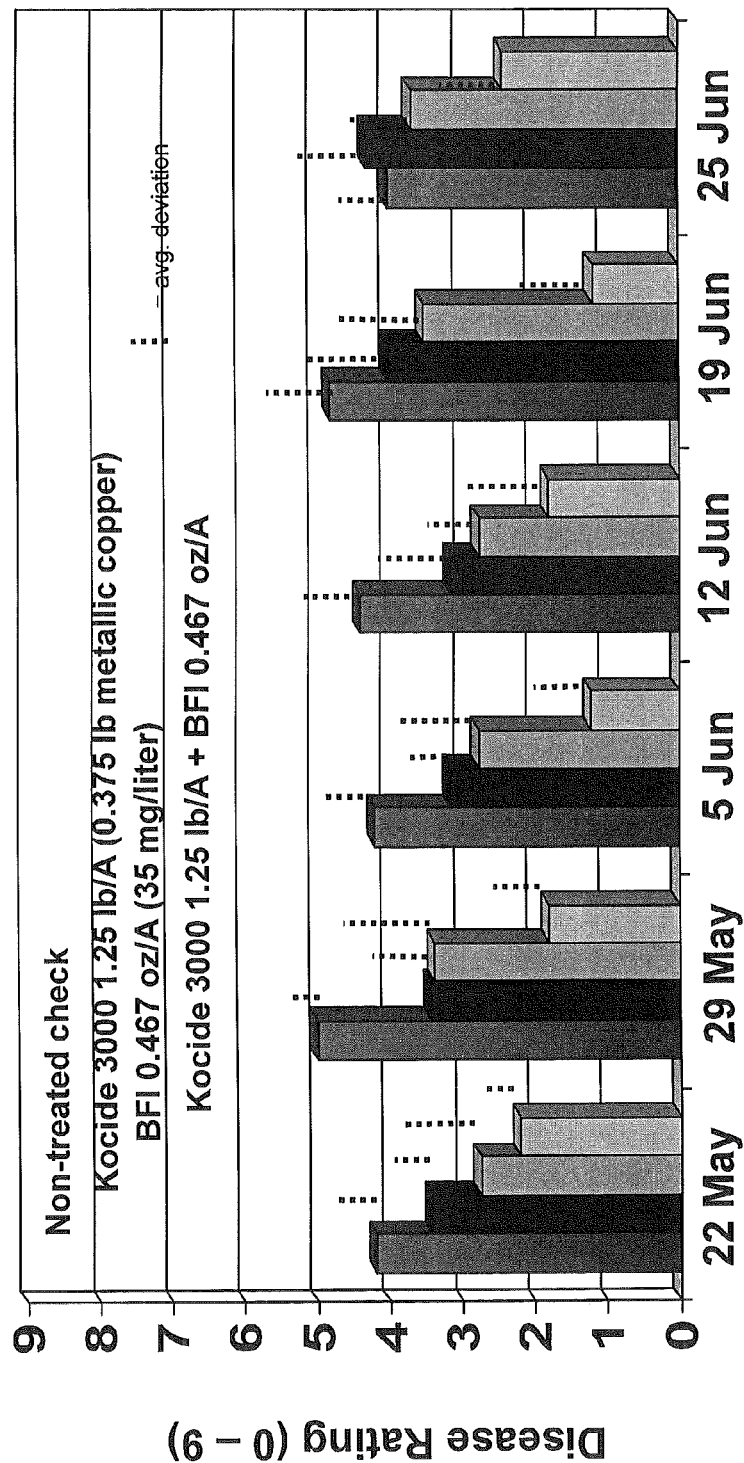
FIG. 4. Evaluation of foliar disease on inoculated pepper plants.
Figure 5:
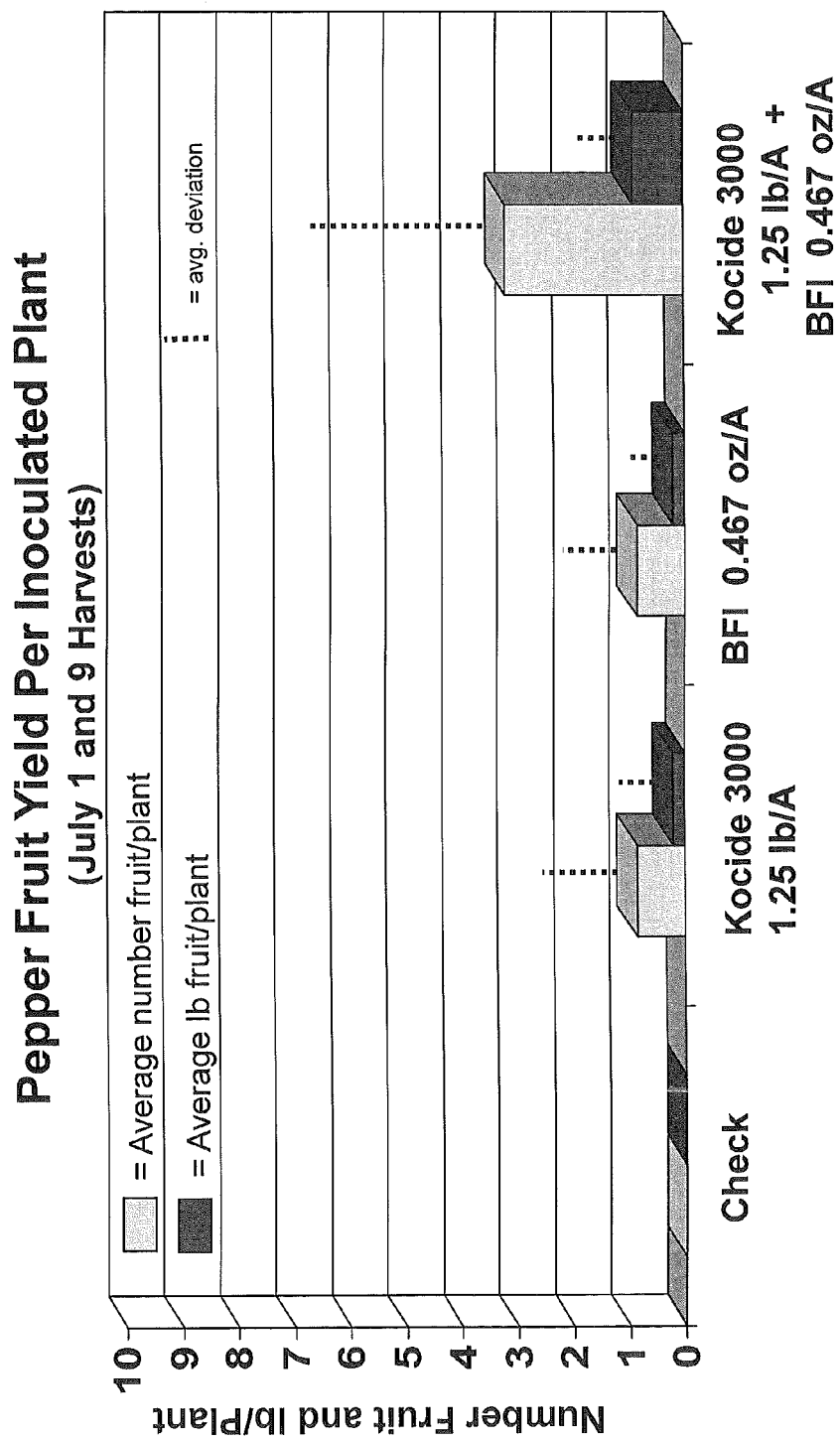
FIG. 5. Pepper fruit yield per inoculated plant.
Figure 6:
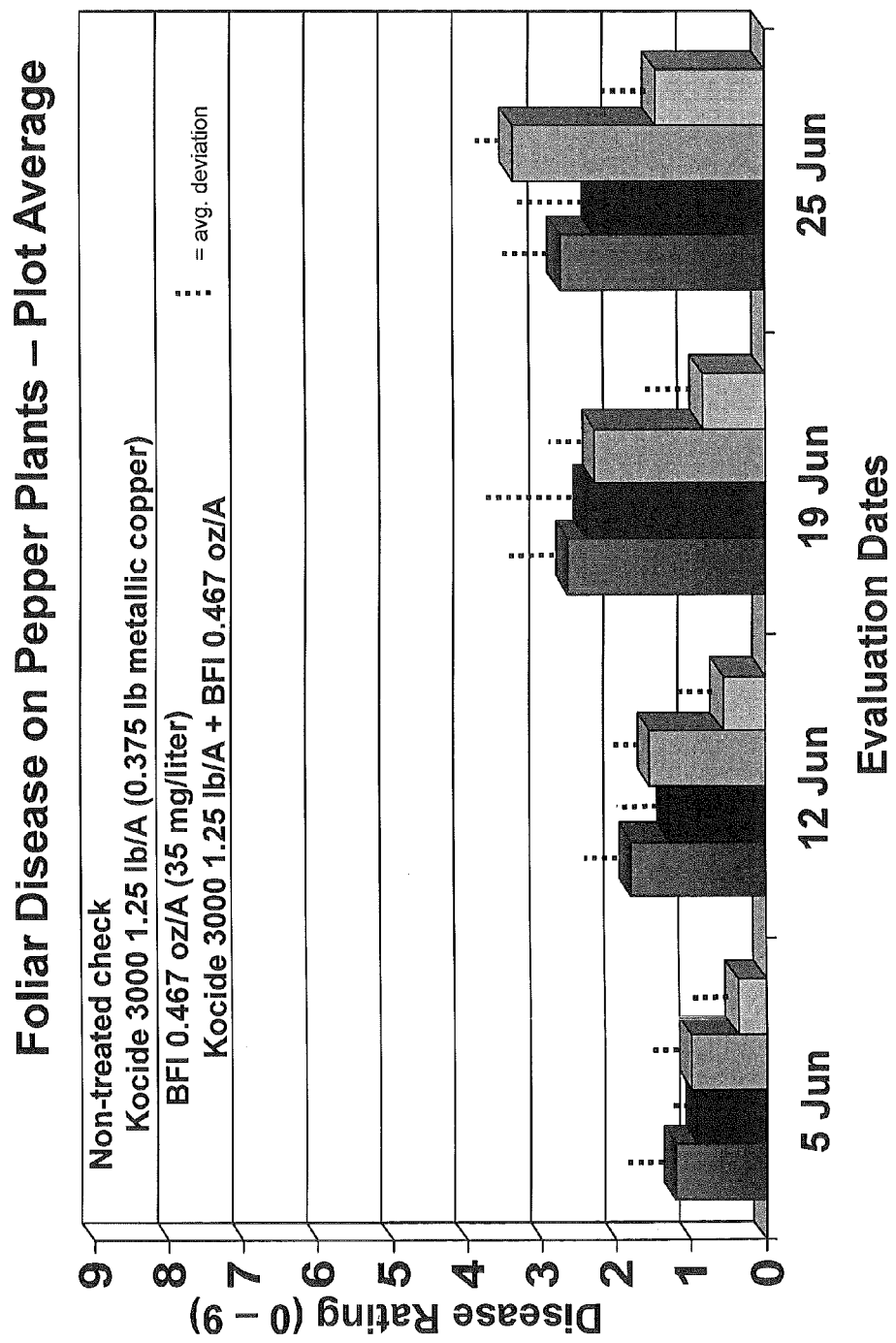
FIG. 6. Evaluation of foliar disease on pepper plants measured by plot average.
Figure 7:
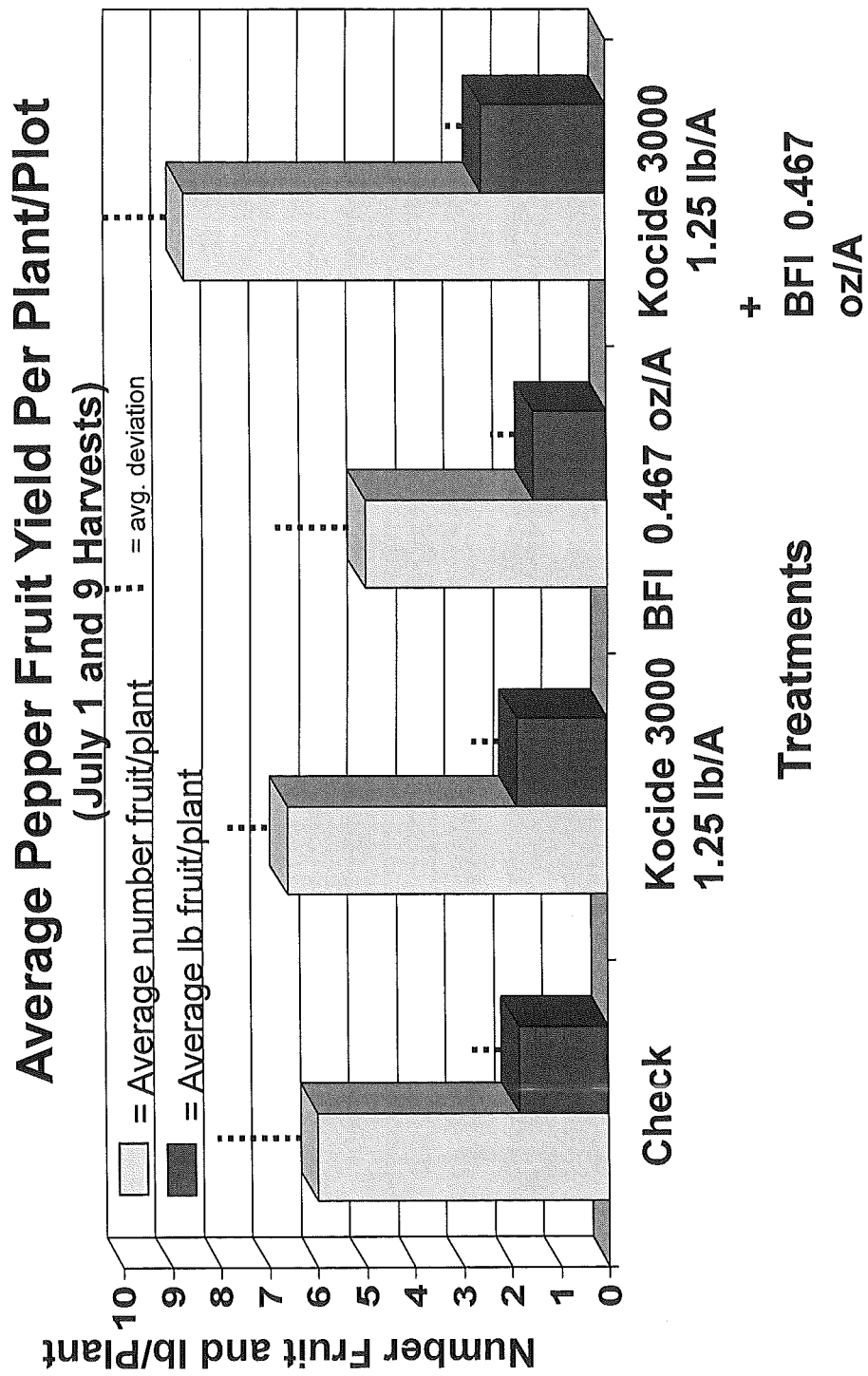
FIG. 7. Average pepper fruit yield per plant/plot, July 1 and 9 harvests.

The present invention is further described below. All patent references referred to in this patent application are hereby incorporated by reference in their entirety as if set forth fully herein.

A. Definitions

"Active compound" as used herein refers to the various embodiments of compounds described in Section B (triazole derivatives) set forth below.

"Plant" as used herein includes all members of the plant kingdom, including higher (or "vascular") plants and lower ("non-vascular") plants, and particularly including all plants in the divisions Filicinae, Gymnospermae (or "gymnosperm"), and Angiospermae (or "Angiosperm"). Nonvascular plants of the present invention include, but are not limited to, bryophytes.

A plant of the present invention includes, but is not limited to, a crop plant, a turf grass, an ornamental species, a species grown for timber or pulp, a species grown for biofuels or species grown for pharmaceuticals. Additionally, plants of the present invention include, but are not limited to, tobacco, tomato, potato, sugar beet, pea, carrot, cauliflower, broccoli, soybean, canola, sunflower, alfalfa, cotton, rapeseed, *Arabidopsis*, peach, pepper, apple, chile, peanut, orange, grape, coffee, cassaya, spinach, lettuce, cucumber, wheat, maize, rye, rice, turfgrass, oat, barley, sorghum, millet, sugarcane, or banana.

"Angiosperm" as used herein includes, but is not limited to, plants of the sub-classes Monocotyledoneae (or monocots) and Dicotyledoneae (or dicots).

Monocotyledoneae (or monocots) as used herein includes but is not limited to Amaryllidaceae—the Amaryllis Family, Gramineae (Poaceae)—the Grass Family, Liliaceae—the Lily Family, Orchidaceae—the Orchid Family, Palmae (Aracaceae)—the Palm Family; and Lemnacea—the duckweed family.

Dicotyledoneae (or dicots) as used herein includes but is not limited to Cactacae—the Cactus Family, Compositae (Asteraceae)—the Sunflower Family, Cruciferae (Brassicaceae)—the Mustard Family, Cucurbitaceae—the Gourd Family, Ericaceae—the Heath Family, Euphorbiaceae—the Spurge Family, Lauraceae—the Laurel Family, Leguminosae (Fabaceae)—the Pea Family, Rosaceae—the Rose Family, Rutaceae—the Rue Family, Solanaceae—the Nightshade Family, and Umbelliferae (Apiaceae)—the Carrot family.

Gymnospermae (or "Gymnosperms") as used herein includes but is not limited to conifers.

"Conifer," as used herein, refers to a member of the order Coniferae in the sub-phylum Gymnospermae in the phylum Spermaphyta. Exemplary conifers which may be used in practicing the present invention are the members of the family Pinaceae, which include, for example, loblolly pine (*Pinus taeda*), slash pine (*Pinus elliotii*), longleaf pine (*Pinus palustris*), shortleaf pine (*Pinus echinata*), ponderosa pine (*Pinus ponderosa*), red pine (*Pinus resinosa*), jack pine (*Pinus banksiana*), Eastern white pine (*Pinus strobus*), Western white pine (*Pinus monticola*), sugar pine (*Pinus lambertiana*), lodgepole pine (*Pinus contorta*), Monterey pine (*Pinus radiata*), Afghan pine (*Pinus eldarica*), Scots pine (*Pinus sylvestris*), and Virginia pine (*Pinus virginiana*); Douglas-fir (*Pseudotsuga menziesii*); Western hemlock (*Tsuga canadensis*); Sitka spruce (*Picea glauca*); redwood (*Sequoia sempervirens*); the true firs including silver fir (*Abies amabilis*), grand fir (*Abies grandis*) noble fir (*Abies procera*), white fir (*Abies concolor*), balsam fir (*Abies balsamea*); and the cedars which include Western red cedar (*Thuja plicata*), incense cedar (*Libocedrus decurrens*), Port Orford cedar (*Chamaecyparis lawsoniona*), and Alaska yellow-cedar (*Chamaecyparis nootkatensis*); and Western larch (*Laryx occidentalis*). See, e.g., U.S. Pat. No. 5,122,466 to Stomp et al.

"Duckweed" as used herein includes plants of the genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Spirodela* (*S. intermedia, S. polyrrhiza, S. punctata*); genus *Wolffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*) and genus *Wolfiella* (*Wl. caudata, Wl. denticulata, Wl. gladiata, Wl. hyalina, Wl. lingulata, Wl. repunda, Wl. rotunda, and Wl. neotropica*). See, e.g., U.S. Pat. No. 7,161,064 to Stomp et al.

Particular examples of plants include but are not limited to all cereal and grain crops, herbs and spices, oil seed crops, sugarcane, vegetable crops, brassica vegetables, bulb vegetables, cucurbit vegetables and fruit, leafy vegetables, fruiting vegetables, legume vegetables, root and tuber vegetables, tree, vine and shrub crops, berry crops, citrus (e.g., orange, grapefruit, Mandarin (including Tangerine and Satsuma), lemon, lime, and kumquat), pome fruit (e.g., apple, pear, quince, Asian pear, loquat, etc.), stone fruit (e.g., peach, apricot, prune, plum, cherries, almond, etc.), miscellaneous tree food crops, non-food tree crops, tree nuts, tropical and subtropical trees and fruit, vine crops, pasture grasses, forage legumes, and rangeland, grass seed or sod production, pastures, cotton, corn, soybeans, rice, wheat, greenhouse/shadehouse grown plants, ornamental, plant nurseries, Christmas trees, golf courses and turf, forestry, tobacco, orchids, flowers and roses, foliage crops, algae such as green algae, bryophytes (mosses, liverworts, hornworts), etc. Note that "foliage crops" refers to the types of plants (ferns, etc.) that are typically used in home or commercial settings for decorative purposes; this alone constitutes a very large commercial industry.

"Plant part" as used herein refers to seeds, roots, leaves, shoots, fruits (e.g., apples, pineapples, citrus fruit, etc.), vegetables, tubers, flowers (e.g., cut flowers such as roses, as well as the reproductive parts of plants), petals, stem, trunk, etc., harvested or collected from a plant as described herein. The plant part of a vascular plant may be a non-vascular part, such as a seed or meristem (growing tip of a shoot).

"Applying" as described herein can be carried out directly or indirectly by any suitable technique, including topically applying to the plant or plant part, applying to the media in which the plant or plant part is grown, stored, displayed or maintained (e.g., adding to water in which the stems of cut flowers are placed), etc. Note that the plant may be grown in any suitable media, including but not limited to soil, potting soil, soilless media such as sand and hydroponic media (including solution culture, medium culture, and deep water culture), etc.

"Agricultural composition" as described herein may be in any suitable form, including but not limited to: wettable powders, dry flowables, soluble powders, water dispersibles, liquids, dusts, emulsifiable concentrates, flowables, fumigants, water dispersible granules, liquid concentrates, granules, water soluble packages, wettable powders in water soluble films, emulsions, etc.

"Triazole" refers to the commonly known structures:

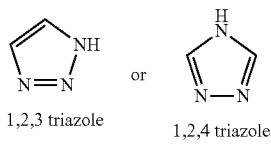 [SMILES: c1c[nH]nn1 ; c1nnc[nH]1]

1,2,3 triazole    1,2,4 triazole

"Imidazole" refers to the commonly known structure:

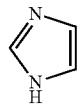

"H" refers to a hydrogen atom. "C" refers to a carbon atom. "N" refers to a nitrogen atom. "O" refers to an oxygen atom. "Halo" refers to F, Cl, Br or I. The term "hydroxy," as used herein, refers to an —OH moiety. "Br" refers to a bromine atom. "Cl" refers to a chlorine atom, "I" refers to an iodine atom. "F" refers to a fluorine atom.

An "acyl group" is intended to mean a group —C(O)—R, where R is a suitable substituent (for example, an acetyl group, a propionyl group, a butyroyl group, a benzoyl group, or an alkylbenzoyl group).

"Alkyl," as used herein, refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. In some embodiments, alkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As generally understood by those of ordinary skill in the art, "saturation" refers to the state in which all available valence bonds of an atom (e.g., carbon) are attached to other atoms. Similarly, "unsaturation" refers to the state in which not all the available valence bonds are attached to other atoms; in such compounds the extra bonds usually take the form of double or triple bonds (usually with carbon). For example, a carbon chain is "saturated" when there are no double or triple bonds present along the chain or directly connected to the chain (e.g., a carbonyl), and is "unsaturated" when at least one double or triple bond is present along the chain or directly connected to the chain (e.g., a carbonyl). Further, the presence or absence of a substituent depending upon chain saturation will be understood by those of ordinary skill in the art to depend upon the valence requirement of the atom or atoms to which the substituent binds (e.g., carbon).

The term "optionally substituted" indicates that the specified group is either unsubstituted, or substituted by one or more suitable substituents. A "substituent" is an atom or atoms substituted in place of a hydrogen atom on the parent chain or cycle of an organic molecule, for example, H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkenyl," as used herein, refers to a straight or branched chain hydrocarbon containing from 1 or 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. In some embodiments, alkenyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkynyl," as used herein, refers to a straight or branched chain hydrocarbon group containing from 1 or 2 to 10 or 20 or more carbon atoms, and containing at least one carbon-carbon triple bond. Representative examples of alkynyl include, but are not limited, to acetylenyl, 1-propynyl, 2-propynyl, 3-butynyl, 2-pentynyl, 1-butynyl and the like. In some embodiments, alkynyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "cycloalkyl," as used herein, refers to a saturated cyclic hydrocarbon group containing from 3 to 8 carbons or more. Representative examples of cycloalkyl include, cyclopropyl, cyclobutyl, cyclopentyl, cyclohexyl, cycloheptyl, and cyclooctyl. In some embodiments, cycloalkyl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Heterocyclo," as used herein, refers to a monocyclic or a bicyclic ring system. Monocyclic heterocycle ring systems are exemplified by any 5 or 6 member ring containing 1, 2, 3, or 4 heteroatoms independently selected from the group consisting of: O, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. In some embodiments, heterocyclo groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Aryl" as used herein refers to a fused ring system having one or more aromatic rings. Representative examples of aryl include, azulenyl, indanyl, indenyl, naphthyl, phenyl, tetrahydronaphthyl, and the like. The aryl groups of this invention can be substituted with 1, 2, 3, 4, or 5 substituents independently selected from alkenyl, alkenyloxy, alkoxy, alkoxyalkoxy, alkoxycarbonyl, alkyl, alkylcarbonyl, alkylcarbonyloxy, alkylsulfinyl, alkylsulfonyl, alkylthio, alkynyl, aryl, aryloxy, azido, arylalkoxy, arylalkyl, aryloxy, carboxy, cyano, formyl, halogen, haloalkyl, haloalkoxy, hydroxy, hydroxyalkyl, mercapto, nitro, sulfamyl, sulfo, sulfonate, —NR'R" (wherein, R' and R" are independently selected from hydrogen, alkyl, alkylcarbonyl, aryl, arylalkyl and formyl), and —C(O)NR'R" (wherein R' and R" are independently selected from hydrogen, alkyl, alkylcarbonyl, aryl, arylalkyl, and formyl). In some embodiments, aryl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O. In some embodiments, heteroaryl groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

"Alkoxy," as used herein, refers to an alkyl group, as defined herein, appended to the parent molecular moiety through an oxy group, as defined herein. Representative examples of alkoxy include, but are not limited to, methoxy, ethoxy, propoxy, 2-propoxy, butoxy, tert-butoxy, pentyloxy, hexyloxy and the like. In some embodiments, alkoxy groups as described herein are optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

An "amine" or "amino" is intended to mean the group —NH$_2$. "Optionally substituted" amines refers to —NH$_2$ groups wherein none, one or two of the hydrogens is replaced by a suitable substituent as described herein, such as alkyl, alkenyl, alkynyl, cycloalkyl, heterocyclo, aryl, heteroaryl, alkoxy, carbonyl, carboxy, etc. In some embodiments, one or two of the hydrogens are optionally substituted with independently selected, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide. Disubstituted amines may have substituents that are bridging, i.e., form a heterocyclic ring structure that includes the amine nitrogen.

An "amide" as used herein refers to an organic functional group having a carbonyl group (C=O) linked to a nitrogen atom (N), or a compound that contains this group, generally depicted as:

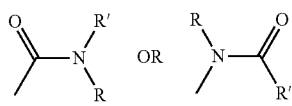

wherein, R and R' can independently be any covalently-linked atom or atoms, for example, H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A "thiol" or "mercapto" refers to an —SH group or to its tautomer =S.

A "sulfone" as used herein refers to a sulfonyl functional group, generally depicted as:

wherein, R can be any covalently-linked atom or atoms, for example, H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

A "sulfoxide" as used herein refers to a sulfinyl functional group, generally depicted as:

wherein, R can be any covalently-linked atom or atoms, for example, H, halohydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

The term "oxo," as used herein, refers to a =O moiety. The term "oxy," as used herein, refers to a —O— moiety.

"Nitro" refers to the organic compound functional group —NO$_2$.

"Carbonyl" is a functional group having a carbon atom double-bonded to an oxygen atom (—C=O). "Carboxy" as used herein refers to a —COOH functional group, also written as —(C=O)—OH.

"Amino acid sidechain" as used herein refers to any of the 20 commonly known groups associated with naturally-occurring amino acids, or any natural or synthetic homologue thereof. An "amino acid" includes the sidechain group and the amino group, alpha-carbon atom, and carboxy groups, as commonly described in the art. Examples of amino acids include glycine, and glycine that is substituted with a suitable substituent as described herein, such as alkyl, alkenyl, alkynyl, cycloalkyl, heterocyclo, aryl, heteroaryl, alkoxy, carbonyl, carboxy, etc., or an agriculturally acceptable salt thereof. For example, "Histidine" is one of the 20 most commonly known amino acids found naturally in proteins. It contains an imidazole side chain substituent. Other examples of naturally-occurring amino acids include lysine, arginine, aspartic acid, glutamic acid, asparagine, glutamine, serine, threonine, tyrosine, alanine, valine, leucine, isoleucine, phenylalanine, methionine, cryptophan, and cysteine. Also included in the definitions of "amino acid sidechain" and "amino acid" is proline, which is commonly included in the definition of an amino acid, but is technically an imino acid. As used in this application, both the naturally-occurring L-, and the non-natural D-amino acid enantiomers are included. The single letter code for amino acids is A (Ala), C (Cys), D (Asp), E (Glu), F (Phe), G (Gly), H(His), I (Ile), K (Lys), L (Leu), M (Met), N (Asn), P (Pro), Q (Gln), R (Arg), S (Ser), T (Thr), V (Val), W (Trp), and Y (Tyr). A "peptide" is a linear chain of amino acids covalently linked together, typically through an amide linkage, and contains from 1 or 2 to 10 or 20 or more amino acids, and is also optionally substituted and/or branched.

"Agriculturally acceptable salt" is intended to mean a salt that retains the biological effectiveness of the free acids and bases of a specified compound and that is not biologically or otherwise undesirable. Examples of agriculturally acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

The term "optionally substituted" indicates that the specified group is either unsubstituted, or substituted by one or more suitable substituents. A "substituent" is an atom or atoms substituted in place of a hydrogen atom on the parent chain or cycle of an organic molecule.

B. Active Compounds

Active compounds are provided below. In some of the embodiments provided in the present invention, active compounds are derivatives of triazole. In some embodiments, active compounds include imidazole-triazole conjugates. In some embodiments, active compounds include 2-aminoimidazole-triazole conjugates ("2-AIT"). Active compounds as described herein can be prepared as detailed below or in accordance with known procedures or variations thereof that will be apparent to those skilled in the art.

As will be appreciated by those of skill in the art, the active compounds of the various formulas disclosed herein may contain chiral centers, e.g. asymmetric carbon atoms. Thus, the present invention is concerned with the synthesis of both: (i) racemic mixtures of the active compounds, and (ii) enantiomeric forms of the active compounds. The resolution of racemates into enantiomeric forms can be done in accordance with known procedures in the art. For example, the racemate may be converted with an optically active reagent into a diastereomeric pair, and the diastereomeric pair subsequently separated into the enantiomeric forms.

Geometric isomers of double bonds and the like may also be present in the compounds disclosed herein, and all such stable isomers are included within the present invention unless otherwise specified. Also included in active compounds of the invention are tautomers (e.g., tautomers of triazole and/or imidazole) and rotamers.

All chains defined by the formulas herein which include three or more discrete carbons may be saturated or unsaturated unless otherwise indicated.

Carbons or other atoms along a chain identified by the Formulas herein may be identified by number, and when identified by number shall be numbered from left to right. For example:

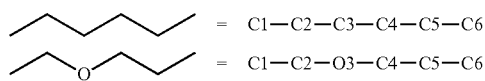

To illustrate where there are two or more discrete chains, for Formula (II)(i)(a) described below, wherein $R^2$, $R^3$, $R^4$, $R^5$, $R^7$ and $R^8$=H, and $R^6$=phenyl:

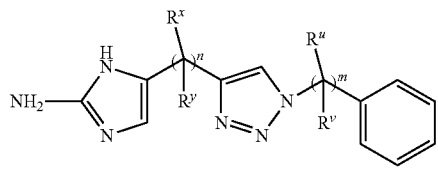

the exemplary structure below shows n=5, saturated, one of either $R^x$ or $R^y$=methyl at C4; m=3, unsaturated, $R^u$=methyl at C2 ($R^v$ is absent at C2); and $R^x$, $R^y$, $R^u$ and $R^v$=H at all other occurrences:

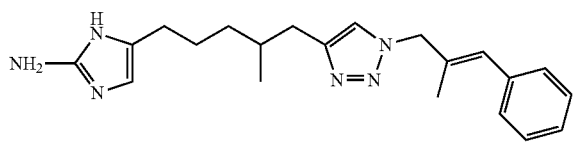 [SMILES: C/C(=C\c1ccccc1)Cn1cc(CC(C)CCCc2cnc(N)[nH]2)nn1]

Active compounds for carrying out the present invention include compounds of Formula (I):

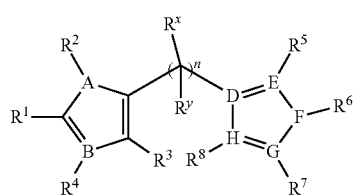

wherein:

$R^1$, $R^2$, $R^3$, $R^4$, $R^5$, $R^6$, $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^x$ and $R^y$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and A, B, D, E, F, G and H are each independently selected from carbon, N, S and O, wherein at least one of D, E, F, G and H is carbon; and n=0 to 20, saturated or unsaturated;

or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As will be appreciated by those of skill in the art, a given substituent ($R^1$-$R^8$) may be present or absent depending upon the valence requirement of the atom or atoms to which the substituent binds (e.g., carbon versus nitrogen).

In some embodiments of Formula (I), $R^1$ is a substituted amino, A, B, F, G and H are each N, and D and E are each carbon, generally depicted by Formulas (I)(a)(1)-(I)(b)(1):

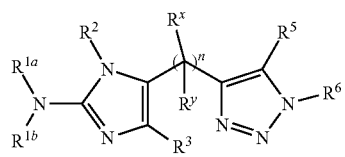

wherein:

$R^{1a}$, $R^{1b}$, $R^2$, $R^3$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and each occurrence of $R^x$ and $R^y$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and n=0 to 20;

or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

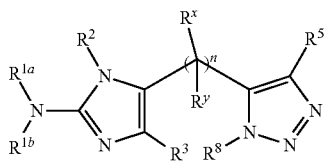

(I)(a)(2)

wherein:

$R^{1a}$, $R^{1b}$, $R^2$, $R^3$, $R^5$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and each occurrence of $R^x$ and $R^y$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and n=0 to 20;

or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (I), $R^1$ is a substituted amino, A, B, F, G and D are each N, and D and E are each carbon, generally depicted by Formula (I)(b)(2):

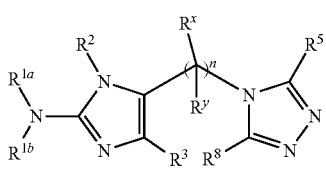

(I)(b)(2)

wherein:

$R^{1a}$, $R^{1b}$, $R^2$, $R^3$, $R^5$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^x$ and $R^y$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and n=0 to 20;

or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Active compounds further include compounds of Formula (I)(i):

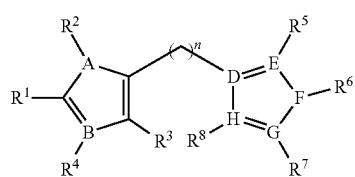

(I)(i)

wherein:

$R^1$, $R^2$, $R^3$, $R^4$, $R^5$, $R^6$, $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20, saturated or unsaturated;

or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As will be appreciated by those of skill in the art, a given substituent ($R^1$-$R^8$) may be present or absent depending upon the valence requirement of the atom or atoms to which the substituent binds (e.g., carbon versus nitrogen).

In some embodiments of Formula (I)(i), $R^1$ is a substituted amino; $R^2$, $R^3$, $R^4$, $R^5$, $R^7$ and $R^8$=H; A, B, F, G and H are each N, and D and E are each carbon, generally depicted by Formula (I)(i)(a):

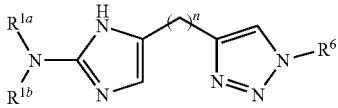

(I)(i)(a)

wherein:

$R^6$ is selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide; and n=0 to 20, saturated or unsaturated;

or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Active compounds for carrying out the present invention include compounds of Formula (II):

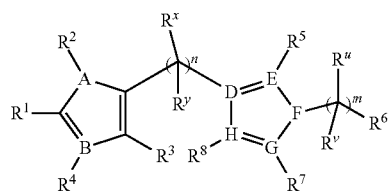

wherein:

R$^1$, R$^2$, R$^3$, R$^4$, R$^5$, R$^6$, R$^7$ and R$^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of R$^x$, R$^y$, R$^u$ and R$^v$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20; and m=0 to 20;

or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As will be appreciated by those of skill in the art, a given substituent (R$^1$-R$^8$) may be present or absent depending upon the valence requirement of the atom or atoms to which the substituent binds (e.g., carbon versus nitrogen).

In some embodiments of Formula (II), R$^1$ is a substituted amino, A, B, F, G and H are each N, and D and E are each carbon, generally depicted by Formula (II)(a):

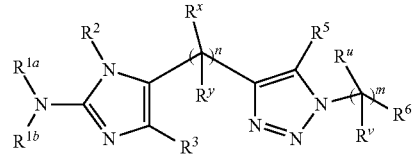

wherein:

R$^{1a}$, R$^{1b}$, R$^2$, R$^3$, R$^5$ and R$^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of R$^x$, R$^y$, R$^u$ and R$^v$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20; and m=0 to 20;

or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (II)(a), R$^{1a}$, R$^{1b}$, R$^2$, R$^3$ and R$^5$ are each H and R$^6$ is phenyl, examples of which include, but are not limited to, the following exemplary Formulas. Each occurrence of R$^x$, R$^y$, R$^u$ and R$^v$ present is H unless otherwise indicated.

Formulas (II)(a)(1)(A)-(II)(a)(1)(D), wherein n=1:

m = 1:

(II)(a)(1)(A)

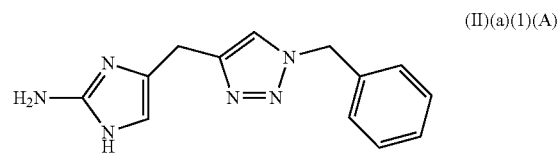

m = 2:

(II)(a)(1)(B)

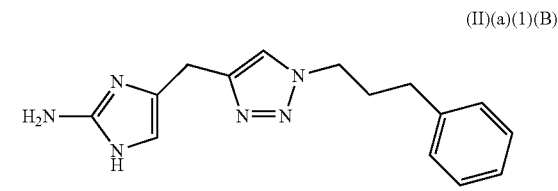

m = 3:

(II)(a)(1)(C)

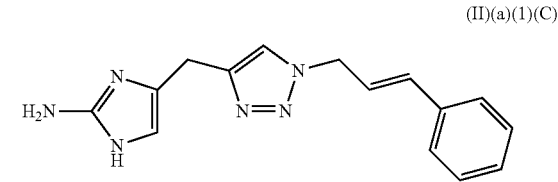

m = 3, R$^u$ = methyl at C2

(II)(a)(1)(D)

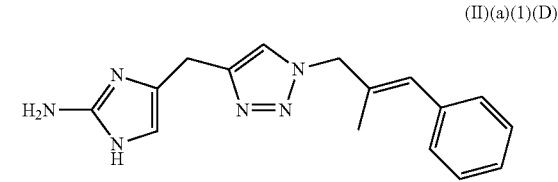

Formulas (II)(a)(2)(A)-(II)(a)(2)(D), wherein n=2:
m = 1:
(II)(a)(2)(A)
m = 2:
(II)(a)(2)(B)
m = 3:
(II)(a)(2)(C)
m = 3, $R^u$ = methyl at C2:
(II)(a)(2)(D)
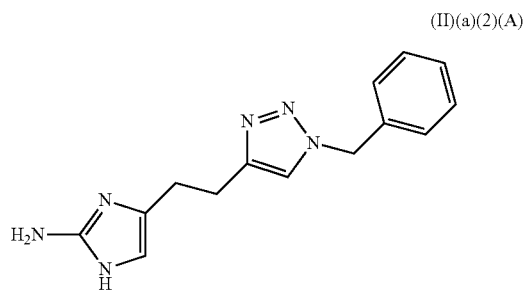
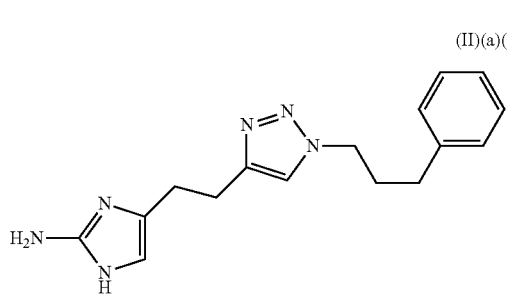
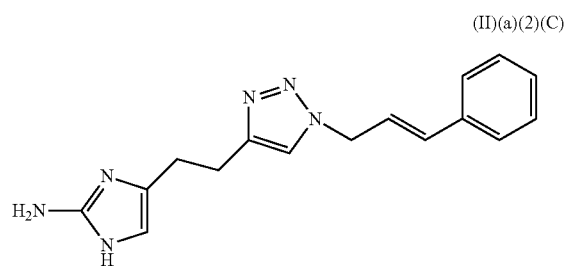
Formulas (II)(a)(3)(A)-(II)(a)(3)(D), wherein n=3:
m = 1:
(II)(a)(3)(A)
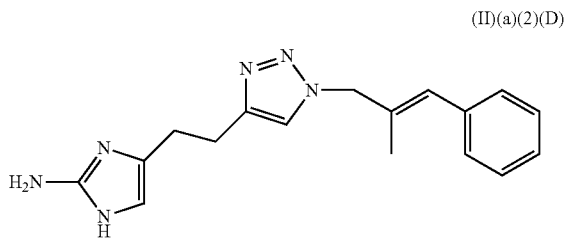
m = 2:
(II)(a)(3)(B)
m = 3:
(II)(a)(3)(C)
m = 3, $R^u$ = methyl at C2:
(II)(a)(3)(D)
Formula (II)(a)(4)(D), wherein n=4; m=3, $R^u$=methyl at C2:
(II)(a)(4)(D)
Formula (II)(a)(5)(D), wherein n=5; m=3, $R^u$=methyl at C2:
(II)(a)(5)(D)
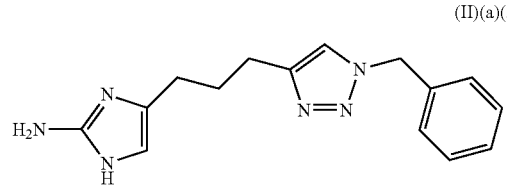

Formula (II)(a)(6)(D), wherein n=6; m=3, R$^u$=methyl at C2:

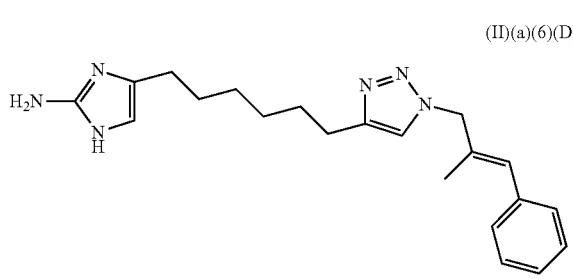 [SMILES: C/C(=C\c1ccccc1)Cn1cc(CCCCCCc2c[nH]c(N)n2)nn1]

Active compounds further include compounds of Formula (II)(i):

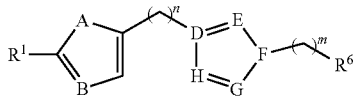

wherein:
R$^1$ and R$^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
A, B, D, E, F, G and H are each independently selected from carbon, N, S and O, wherein at least one of D, E, F, G and H is carbon;
n=0 to 20, saturated or unsaturated; and
m=0 to 20, saturated or unsaturated;
or an agriculturally acceptable salt thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (II)(i), R$^1$ is a substituted amino, A, B, F, G and H are each N, and D and E are each carbon, generally depicted by Formula (II)(i)(a):

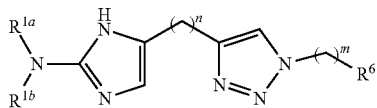

wherein:
R$^{1a}$, R$^{1b}$ and R$^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;
n=0 to 20, saturated or unsaturated; and
m=0 to 20, saturated or unsaturated;
or an agriculturally acceptable salt thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (II)(i)(a), R$^{1a}$ and R$^{1b}$ are each H, and R$^6$ is heteroaryl, examples of which include, but are not limited to, the following exemplary Formulas:

Formulas (II)(i)(a)(1)(E)-(II)(i)(a)(1)(L), wherein n=1:

m = 1; R$^4$ is thiophenyl:

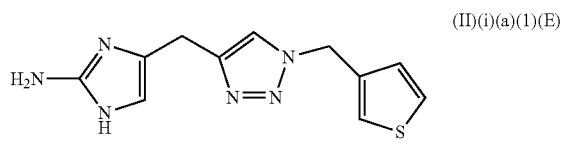

m = 2; R$^4$ is thiophenyl:

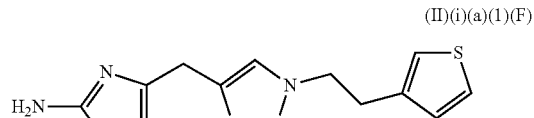

m = 1; R$^4$ is furyl:

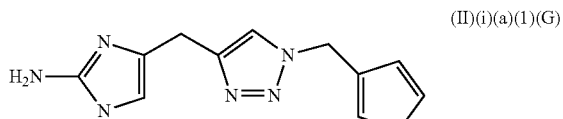

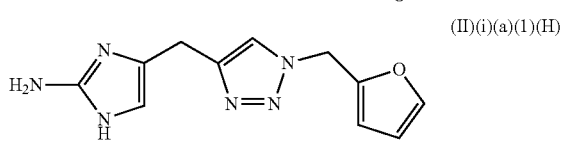

m = 1; R$^4$ is indolyl:

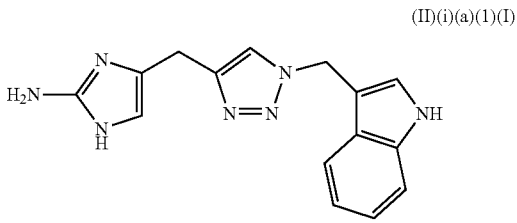

m = 2; R$^4$ is indolyl:

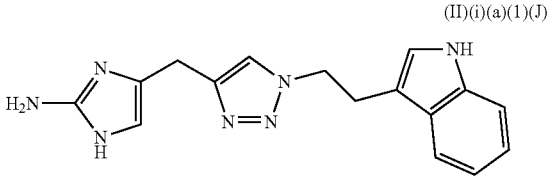

m = 1; R$^4$ is benzimidazolyl:

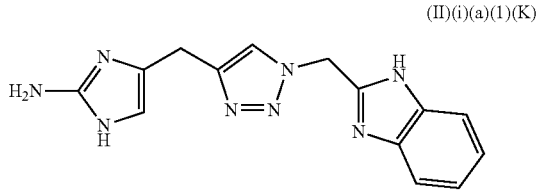

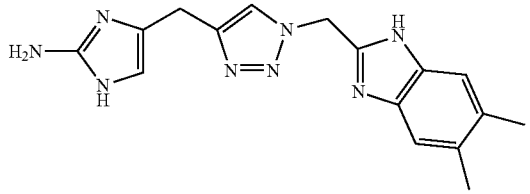

(II)(i)(a)(1)(L)

Further embodiments include Formulas (II)(i)(a)(2)(E)-(II)(i)(a)(2)(L), wherein n=2; Formulas (II)(i)(a)(3)(E)-(II)(i)(a)(3)(L), wherein n=3; Formulas (II)(i)(a)(4)(E)-(II)(i)(a)(4)(L), wherein n=4; Formulas (II)(i)(a)(5)(E)-(II)(i)(a)(5)(L), wherein n=5; Formulas (II)(i)(a)(6)(E)-(II)(i)(a)(6)(L), wherein n=6; and so on.

These formulas may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Also provided are compounds of Formula (III):

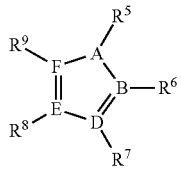

(III)

wherein:

$R^5$, $R^6$, $R^7$, $R^8$ and $R^9$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and A, B, D, E and F are each independently selected from carbon, N, S and O, wherein at least one of A, B, D, E and F is carbon;

or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

As will be appreciated by those of skill in the art, a given substituent ($R^5$-$R^9$) may be present or absent depending upon the valence requirement of the atom or atoms to which the substituent binds (e.g., carbon versus nitrogen).

In some embodiments of Formula (III), B, D and E are each N, and A and F are each carbon, generally depicted as Formula (III)(a):

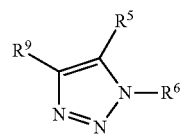

(III)(a)

wherein:

$R^5$, $R^6$ and $R^9$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (III), A, D and E are each N, and B and F are each carbon, generally depicted as Formula (III)(b):

(III)(b)

wherein:

$R^5$, $R^6$ and $R^9$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (III)(b), $R^6$ and $R^9$ are each H, generally depicted by Formula (III)(b)(i):

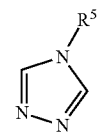

(III)(b)(i)

wherein:

$R^5$ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (III)(b), $R^5$ and $R^6$ are each H, generally depicted by Formula (III)(b)(ii):

(III)(b)(ii)

wherein:
$R^9$ is selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide; and
or an agriculturally acceptable salt thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Also provided are compounds of Formula (IV):

(IV)

wherein:
$R^1$, $R^2$, $R^3$, $R^4$, $R^5$, $R^6$, $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
A, B, D, E, F, G and H are each independently selected from carbon, N, S and O, wherein at least one of D, E, F, G and H is carbon; and
n=0 to 20;
m=0 to 20; and
p=0 to 20
or an agriculturally acceptable salt thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (IV), $R^1$ is a substituted amino, A, B, F, G and H are each N, and D and E are each carbon, generally depicted by Formula (IV)(a):

(IV)(a)

wherein:
$R^{1a}$, $R^{1b}$, $R^2$, $R^3$, $R^5$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;
each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
n=0 to 20;
m=0 to 20; and
p=0 to 20
or an agriculturally acceptable salt thereof.
This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments, $R^6$ is a group:

(i)

wherein:
X, Y and Z are each independently selected from the group consisting of: H, methyl, Br and Cl.
In some embodiments, $R^6$ is a group:

(ii)

wherein:
$R^{20}$, $R^{21}$, $R^{22}$, $R^{23}$ and $R^{24}$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Further provided are compounds of Formula (IV)(i):

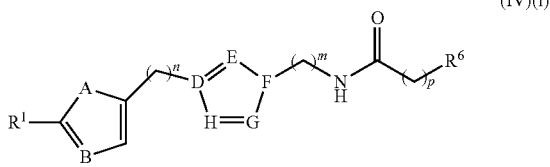

(IV)(i)

wherein:

R¹ and R⁶ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon;

n=0 to 20, saturated or unsaturated;
m=0 to 20, saturated or unsaturated; and
p=0 to 20, saturated or unsaturated;

or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (IV)(i), R¹ is a substituted amino, A, B, F, G and H are each N, and D and E are each carbon, generally depicted by Formula (IV)(i)(a):

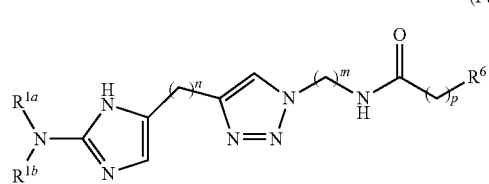

(IV)(i)(a)

wherein:

R¹ᵃ, R¹ᵇ and R⁶ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

n=0 to 20, saturated or unsaturated;
m=0 to 20, saturated or unsaturated; and
p=0 to 20, saturated or unsaturated;

or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (IV)(i)(a), R¹ᵃ, R¹ᵇ and R⁶ are each H. In some embodiments of Formula (IV)(i)(a), R¹ᵃ and R¹ᵇ are each H, and R⁶ is aryl or heteroaryl.

Also provided are compounds of Formula (V):

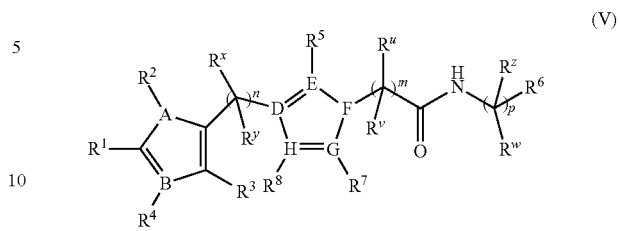

(V)

wherein:

R¹, R², R³, R⁴, R⁵, R⁶, R⁷ and R⁸ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of Rˣ, Rʸ, Rᵘ, Rᵛ, Rᶻ and Rʷ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=~0 to 20;
m=0 to 20; and
p=0 to 20 or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (V), R¹ is a substituted amino, A, B, F, G and H are each N, and D and E are each carbon, generally depicted by Formula (V)(a):

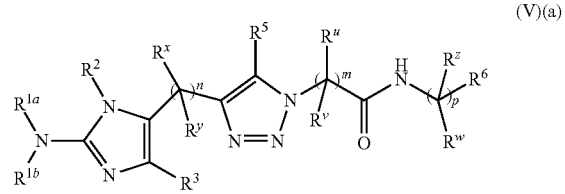

(V)(a)

wherein:

R¹ᵃ, R¹ᵇ, R², R³, R⁵ and R⁶ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of Rˣ, Rʸ, Rᵘ, Rᵛ, Rᶻ and Rʷ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20;
m=0 to 20; and
p=0 to 20
or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Further provided are compounds of Formula (V)(i):

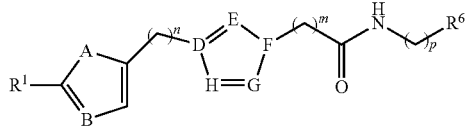

(V)(i)

wherein:

$R^1$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon;

n=0 to 20, saturated or unsaturated;
m=0 to 20, saturated or unsaturated; and
p=0 to 20, saturated or unsaturated;
or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (V)(i), $R^1$ is a substituted amino, A, B, F, G and H are each N, and D and E are each carbon, generally depicted by Formula (V)(i)(a):

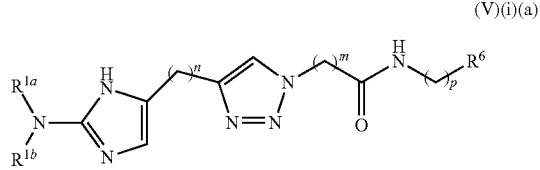

(V)(i)(a)

wherein:

$R^{1a}$, $R^{1b}$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

n=0 to 20, saturated or unsaturated;
m=0 to 20, saturated or unsaturated; and
p=0 to 20, saturated or unsaturated;
or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (V)(i)(a), $R^{1a}$, $R^{1b}$ and $R^6$ are each H, alkyl, cycloalkyl or heterocyclo. In some embodiments of Formula (V)(i)(a), $R^{1a}$ and $R^{1b}$ are each H, and $R^6$ is aryl.

Also provided are compounds of Formula (VI):

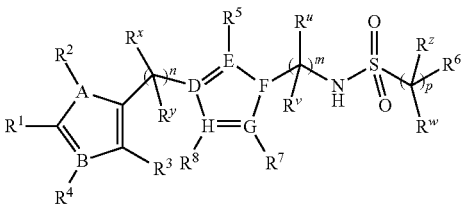

(VI)

wherein:

$R^1$, $R^2$, $R^3$, $R^4$, $R^5$, $R^6$, $R^7$ and $R^8$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon; and n=0 to 20;
m=0 to 20; and
p=0 to 20;
or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (VI), $R^1$ is a substituted amino, A, B, F, G and H are each N, and D and E are each carbon, generally depicted by Formula (VI)(a):

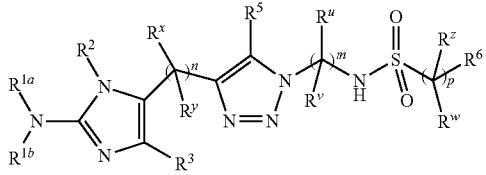

(VI)(a)

wherein:

$R^{1a}$, $R^{1b}$, $R^2$, $R^3$, $R^5$ and $R^6$ are each independently selected from the group consisting of: H, hydroxy, acyl, alkyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

each occurrence of $R^x$, $R^y$, $R^u$, $R^v$, $R^z$ and $R^w$ is present or absent (depending upon chain saturation), and is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

n=0 to 20;
m=0 to 20; and
p=0 to 20;
or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

Further provided are compounds of Formula (VI)(i):

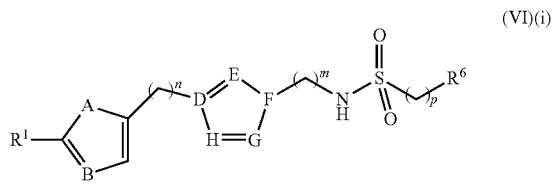

(VI)(i)

wherein:
$R^1$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;

A, B, D, E, F, G and H are each independently selected from carbon, N, S and O, wherein at least one of D, E, F, G and H is carbon;

n=0 to 20, saturated or unsaturated;
m=0 to 20, saturated or unsaturated; and
p=0 to 20, saturated or unsaturated;
or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (VI)(i), $R^1$ is a substituted amino, A, B, F, G and H are each N, and D and E are each carbon, generally depicted by Formula (VI)(i)(a):

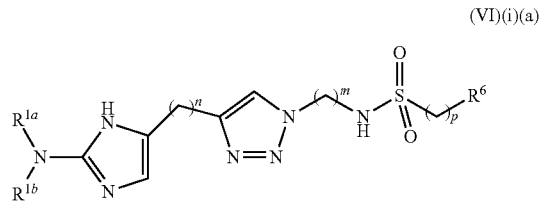

(VI)(i)(a)

wherein:
$R^{1a}$, $R^{1b}$ and $R^6$ are each independently selected from the group consisting of: H, hydroxy, acyl, alkyl, alkenyl, alkynyl, cycloalkyl, heterocyclo, aryl, heteroaryl, alkoxy, amino, amide, sulfone, sulfoxide, oxo, oxy, nitro, carbonyl, carboxy, amino acid sidechain, amino acid and peptide;

n=0 to 20, saturated or unsaturated;
m=0 to 20, saturated or unsaturated; and
p=0 to 20, saturated or unsaturated;
or an agriculturally acceptable salt thereof.

This formula may be optionally substituted (e.g., from 1 to 3 or 4 times) with independently selected H, halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide.

In some embodiments of Formula (VI)(i)(a), $R^{1a}$ and $R^{1b}$ are each H, and $R^6$ is aryl or heteroaryl.

C. Microbicides and Plant Defense Activators

In some embodiments, an active compound described herein is applied in combination with a microbicide. "Microbicide" as used herein refers to a substance with the ability to kill or to inhibit the growth of microorganisms (e.g., bacteria, fungal cells, protozoa, etc.), which microbicide is not an active compound in the group herein disclosed of triazole derivatives. Common microbicides used for microbial control in plants include copper compounds. Examples of copper compounds include, but are not limited to, Bordeaux mixture, copper hydroxide, copper oxychloride, copper sulfate, cuprous oxide, mancopper or oxine-copper. However, microorganisms (e.g., bacteria such as *Xanthomonas* and *Pseudomonas*) may become resistant to treatment with copper.

In some embodiments, resistant microorganisms (e.g., copper-resistant bacteria) are rendered more susceptible to a microbicides and/or the effectiveness of treatment with a microbicides is enhanced upon application in combination with an active compound described herein (e.g., fruit or vegetable yield is increased as compared to diseased plant producing the fruit or vegetable that is untreated or treated only with the microbicide).

Other microbicides include, but are not limited to, azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, SSF-129, methyl 2[(2-trifluoromethyl)-pyrid-6-yloxymethyl]-3-methoxy-acrylate or 2-[{α[(α-methyl-3-trifluoromethyl-benzyl)imino]-oxy}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthiodicarboximides such as captafol, captan, dichlofluanid, fluoromide, folpet or tolyfluanid; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-S-methyl, harpin, anilazine, blasticidin-S, chinomethionat, chloroneb, chlorothalonil, cymoxanil, dichione, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenylamino-3,5-di-hydroimidazol-4-o-ne (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfon-amide (IKF-916), N-(1-cyano-1,2-dimethylpropyl)-2-(2,4-dichlorophenoxy)-propionamide (AC 382042) or iprovalicarb (SZX 722).

An "antibiotic" as used herein is a type of "microbicide." Common antibiotics include aminoglycosides, carbacephems (e.g., loracarbef), carbapenems, cephalosporins, glycopeptides (e.g., teicoplanin and vancomycin), macrolides, monobactams (e.g., aztreonam) penicillins, polypeptides (e.g., bacitracin, colistin, polymyxin B), quinolones, sulfonamides, tetracyclines, etc. Antibiotics treat infections by either killing or preventing the growth of microorganisms. Many act to inhibit cell wall synthesis or other vital protein synthesis of the microorganisms.

Aminoglycosides are commonly used to treat infections caused by Gram-negative bacteria. Examples of aminoglycosides include, but are not limited to amikacin, gentamicin, kanamycin, neomycin, netilmicin, streptomycin, tobramycin, and paromomycin.

Carbapenems are broad-spectrum antibiotics, and include, but are not limited to, ertapenem, doripenem, imipenem/cilstatin, and meropenem.

Cephalosporins include, but are not limited to, cefadroxil, cefazolin, cefalotin (cefalothin), cefalexin, cefaclor, cefamandole, cefoxitin, cefprozil, loracarbef, cefuroxime, cefixime, cefdinir, cefditoren, cefoperazone, cefotaxime, cefpodoxime, ceftazidime, ceftibuten, ceftizoxime, ceftriaxone, cefepime, cefpirome, and ceftobiprole.

Macrolides include, but are not limited to, azithromycin, clarithromycin, dirithromycin, erythromycin, roxithromycin, troleandomycin, telithromycin and spectinomycin.

Penicillins include, but are not limited to, amoxicillin, ampicillin, azlocillin, bacampicillin, carbenicillin, cloxacillin, dicloxacillin, flucloxacillin, mezlocillin, meticillin, nafcillin, oxacillin, penicillin, piperacillin and ticarcillin.

Quinolones include, but are not limited to, ciprofloxacin, enoxacin, gatifloxacin, gemifloxacin, levofloxacin, lomefloxacin, moxifloxacin, norfloxacin, ofloxacin and trovafloxacin.

Sulfonamides include, but are not limited to, mafenide, prontosil, sulfacetamide, sulfamethizole, sulfanilamide, sulfasalazine, sulfisoxazole, trimethoprim, and co-trimoxazole (trimethoprim-sulfamethoxazole).

Tetracyclines include, but are not limited to, demeclocycline, doxycycline, minocycline, oxytetracycline and tetracycline.

Other antibiotics include arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin (rifampicin), tinidazole, etc.

Other microbicides that may be used in combination with the active compounds of the present invention include bacteriophages (bacterial viruses) such as *Bacillus*. Examples of bacteriophage microbicides include, but are not limited to, AgriPhage™ (OmniLytics, Inc., Salt Lake City, Utah) and Serenade® (AgraQuest, Davis, Calif.). See, e.g., U.S. Pat. Nos. 5,919,447 and 6,077,506 to Marrone et al.; U.S. Pat. No. 6,103,228 to Heins et al.; and U.S. Patent Application Publication 20080152684.

In some embodiments, an active compound described herein is applied in combination with a plant defense activator. A "plant defense activator" as used herein is a compound that improves disease resistance by activating a plant's natural defense mechanisms, e.g., induces the plant to produce disease-fighting compounds. Examples of plant defense activators include, but are not limited to, prohexadione-calcium (Apogee), Cropset (plant booster element complex), probenazole, potassium phosphate (e.g., ProPhyt®, Helena Chemical Company), harpin protein (e.g., Messenger®, Eden Biosciences Ltd, Bothell, Wash.), acibenzolar or acibenzolar-S-methyl (e.g., Actigard™, Syngenta Crop Production, Inc, Greensboro, N.C.), streptomycin sulfate, reynoutria sachalinensis extract (reysa), etc.

D. Agrochemical Compositions

Active compounds of the present invention can be used to prepare agrochemical compositions in like manner as other antimicrobial compounds. See, e.g., U.S. Pat. Application 2006/0094739; see also U.S. Pat. Nos. 6,617,330; 6,616,952; 6,569,875; 6,541,500, and 6,506,794.

Active compounds described herein can be used for protecting plants against diseases that are caused by microorganisms, including biofilm-forming microorganisms. The active compounds can be used in the agricultural sector and related fields as active ingredients for controlling plant pests. The active compounds can be used to inhibit or destroy the pests that occur on plants or parts of plants (fruit, blossoms, leaves, stems, tubers, roots) of different crops of useful plants, optionally while at the same time protecting also those parts of the plants that grow later e.g. from phytopathogenic microorganisms.

Active compounds may be used as dressing agents for the treatment of plant propagation material, in particular of seeds (fruit, tubers, grains) and plant cuttings (e.g. rice), for the protection against fungal infections as well as against phytopathogenic fungi occurring in the soil.

The active compounds can be used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides, plant growth regulators, plant activators or mixtures of several of these preparations, if desired together with further carriers, surfactants or application promoting adjuvants customarily employed in the art of formulation.

Suitable carriers and adjuvants can be solid or liquid and are substances useful in formulation technology, e.g. natural or regenerated mineral substances, solvents, dispersants, wetting agents, tackifiers, thickeners, binders or fertilizers.

The active compounds are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances.

The formulation, i.e. the compositions containing the active compound and, if desired, a solid or liquid adjuvant, are prepared in known manner, typically by intimately mixing and/or grinding the compound with extenders, e.g. solvents, solid carriers and, optionally, surface active compounds (surfactants).

Suitable carriers and adjuvants may be solid or liquid and correspond to the substances ordinarily employed in formulation technology, such as, e.g. natural or regenerated mineral substances, solvents, dispersants, wetting agents, tackifiers, thickeners, binding agents or fertilizers. Such carriers are for example described in WO 97/33890.

Further surfactants customarily employed in the art of formulation are known to the expert or can be found in the relevant literature.

The agrochemical formulations will usually contain from 0.1 to 99% by weight, preferably from 0.1 to 95% by weight, of a compound described herein, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The compositions may also contain further adjuvants such as stabilizers, antifoams, viscosity regulators, binders or tackifiers as well as fertilizers, micronutrient donors or other formulations for obtaining special effects.

E. Methods of Use

Target crops or plants to be treated with active compounds and compositions of the invention typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fiber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) or plants such as tobacco, nuts, coffee, eggplants, sugar cane, tea, pepper, vines including grape-bearing vines, hops, bananas, pineapple, turf and natural rubber plants, as well as ornamentals (flowers, shrubs, broad-leafed trees and evergreens, such as conifers). This list does not represent any limitation.

1. Bacterial Infections.

The methods, active compounds and compositions can be used to treat bacterial infections in a variety of plants, with specific examples including but not limited to those set forth below.

Citrus.

In citrus trees (including orange, lemon, lime, and grapefruit) active compounds and compositions as described herein can be used to treat or control a variety of microbial diseases, including but not limited to canker (caused by *Xanthomonas campestris* or *Xanthomonas axonopodis* infection), bacterial spot (caused by *Xanthomonas campestris* pv. *Citrumelo* infection); Black Pit (fruit) (caused by *Pseudomonas syringae* infection); Blast (caused by *Pseudomonas syringae* infection) citrus variegated chlorosis (caused by *Xylella fastidiosa* infection), and Citrus Huanglongbing (HLB) caused by *Candidatus* Liberibacter asiaticus.

Pome Fruit.

In pome fruits (including apple, pear, quince, Asian pear, and loquat), active compounds and compositions as described herein can be used to treat or control a variety of microbial infections, including but not limited to Fire Blight (caused by *Erwinia amylovora* infection), Crown Gall (caused by *Agrobacterium tumefaciens* infection); Blister spot (caused by *Pseudomonas syringae* infection) and Hairy root (caused by *Agrobacterium rhizogenes* infection).

Peppers.

In pepper plants, active compounds and compositions as described herein can be used to treat or control a variety of microbial infections, including but not limited to: Bacterial Spot (caused by *Xanthomonas campestris* pv. *vesicatoria* infection); Bacterial wilt (caused by *Ralstonia solanacearum* infection), and Syringae seedling blight and leaf spot (caused by *Pseudomonas sryingae* infection).

Tomatoes.

In tomato plants, active compounds and compositions as described herein can be used to treat or control a variety of microbial infections, including but not limited to: Bacterial canker (caused by *Clavibacter michiganesis*), Bacterial speck (caused by *Pseudomonas syringae*), Bacterial spot (caused by *Xanthomonas campestris* vesicatoria), Bacterial stem rot and fruit rot (caused by *Erwinia carotovora*), Bacterial wilt (caused by *Ralstonia solanacearum*), Pith necrosis (caused by *Pseudomonas corrugate*), and Syringae leaf spot (caused by *Pseudomonas syringae*).

Soybeans.

In soybeans, active compounds and compositions as described herein can be used to treat or control a variety of microbial infections, including but not limited to: Bacterial blight (caused by *Pseudomonas amygdale*), Bacterial pustules (caused by *Xanthomonas axonopodis* pv. *Glycines*), and Bacterial wilt (caused by *Ralstonia solanacearum* or *Curtobacterium flaccumfaciens*).

Corn, Cotton, Wheat and Rice.

In corn, cotton, wheat and rice, active compounds and compositions as described herein can be used to treat or control a variety of microbial infections, including but not limited to: bacterial blights, leaf spots and leaf streak caused by *Xanthomonas* species; bacterial sheath rot, stripe and spot caused by *Pseudomonas* species; and to bacterial stalk and top rot, wilt, foot rot, pink seed and lint degradation caused by *Erwinia* species.

Pineapple.

In pineapple, active compounds and compositions as described herein can be used to treat or control a variety of microbial infections, including but not limited to: Bacterial heart rot and Fruit collapse (caused by *Erwinia chrysanthemi*), Bacterial fruitlet brown rot (caused by *Erwinia ananas*), Marbled fruit and Pink fruit (caused by *Erwinia herbicola*), Soft rot (caused by *Erwinia carotovora*), and Acetic souring (caused by Acetic acid bacteria).

The above listing is but a sampling, and active compounds and compositions as described herein may also be used to treat or control bacteria (some of which are named above) in a variety of plants. For example, the bacteria *Xylella fastid-*

*iosa* infects citrus trees as noted above (citrus variegated chlorosis), and also infects grapevines (Pierce's disease). Other plant hosts of *Xylella fastidiosa* include, but are not limited to, ornamentals, oleander (leaf scorch), almond, coffee, maple, mulberry, elm, sycamore, alfalfa, etc. Similarly, *Ralstonia solanacearum* infects soybeans (bacterial wilt) as well as banana (Moko disease), tobacco (Granville wilt), geranium (southern bacterial wilt), potato (brown rot) and a wide variety of other plants, including ginger and mulberry.

2. Fungal Infections.

In addition to treating or controlling bacterial infections, active compounds and compositions as described herein can be used to treat or control fungal infections such as rots, leaf molds, blights, wilts, damping-off, spot, root rot, stem rot, mildew, brown spot, gummosis, melanose, post-bloom fruit drop, scab, *alternaria*, canker, flyspeck, fruit blotch, dieback, downy mildews, ear rots, anthracnose bunts, smut, rust, eyespot and pecky rice. Genera of plant-pathogenic fungi that can be treated or controlled by the active compounds, compositions, and methods described herein include but are not limited to: *Pythium* spp., *Fusarium* spp., *Rhizoctonia* spp., *Cercospora* spp., *Alternaria* spp., *Colletotrichum* spp., *Ustilago* spp., *Phoma* spp., *Gibberella* spp. *Penicillium* spp., *Glomerella* spp. *Diplodia* spp., *Curvularia* spp., *Sclerospora* spp., *Peronosclerospora* spp., *Cercospora* spp., *Puccinia* spp., *Ustilago* spp., *Aspergillus* spp., *Phomopsis* spp., *Diaporthe* spp., *Botrytis* spp., *Verticillium* spp., *Phytophthors* spp.

Particular fungal infections that can be treated or controlled by the methods, compounds and compositions described herein, in vegetables and greenhouse crops, include *Phytophthora* blight (caused by *Phytophthora capsici*) and *Pythium* damping-off (caused by *Pythium* spp).

Note that *Phytophthora* also has adverse effects on crops ranging from pineapples to cotton. It can kill woody citrus seedlings and young citrus trees (oranges, grapefruits, lemons, limes). In the greenhouse, germinating seed and seedlings are very susceptible to damping-off caused by *Phytophthora, Pythium, Sclerotina* and *Rhizoctonia* species. The cost to the grower to lose his crop to any of these fungi is substantial. The loss can happen at transplant time or when the crop is ready to be harvested.

The problems of fungi are not restricted to traditional crops but also extend to forestry products and have worldwide scope. *Phytophthora cinnamomi* is a soil-borne water mould that leads to a condition in plants called "root rot" or "dieback." *P. cinnamomi* causes root rot affecting woody ornamentals including azalea, dogwood, forsythia, Fraser fir, hemlock, Japanese holly, juniper, rhododendron, white pine, and American chestnut. *P. cinnamomi* is responsible for the destruction of the elegant American chestnut tree. In Australia, *P. cinnamomi* has spread through the forests of western Australia, and into coastal forests of Victoria, where entire plant ecosystems are being obliterated. Given that *P. cinnamomi* is a soil-borne water mould that infects the roots, almost the entire action takes place below ground. This problem highlights the importance of developing new compounds to counter fungal infections, even those that directly affect only the roots of the plant rather than the more visible effects on fruits or vegetables.

Active compounds of the invention can be applied to plants or plant loci in accordance with known techniques. The compound(s) can be tank mixed with other agricultural, turf, ornamental nursery, forestry and all other plant-labeled compatible pesticides. The compound(s) can be applied to seed. The compound(s) can be applied to edible and non-edible crops. The compound(s) can be applied to roots and all other parts of all plants. The compound(s) can be applied in greenhouses. The compound(s) can be applied and used in food-processing facilities. The compound(s) can be applied to plastic food bags and containers. The compound(s) can be applied as a solid, as its free base, or as a salt. The salts can include, but are not limited to, HI, HCl, HBr, $H_2SO_4$, acetic acid, and trifluoroacetic acid. The compound(s) can applied as a solution from 0.0001% to 99.9%. The compound(s) can be applied as a solid or solution with copper-based cidal compounds. The compound(s) can be applied with specific additional active agents, including but not limited to bactericides, fungicides, pesticides, biological insecticides and microbial insecticides.

Application can be carried out with any suitable equipment or technique, such as: Aerial—Fixed wing and Helicopter; Ground Broadcast Spray—Boom or boomless system, pull-type sprayer, floaters, pick-up sprayers, spray coupes, speed sprayers, and other broadcast equipment, water wagons and water bags; Low pressure boom sprayers, High pressure sprayers; Air blast sprayers; Low volume air sprayers (mist blowers); Ultra-low volume sprayers (ULV); Aerosol Generators (foggers); Dusters; Soil Injector; Hand-Held or High-Volume Spray Equipment—knapsack and backpack sprayers, pump-up pressure sprayers, hand guns, motorized spray equipment; Selective Equipment—Recirculating sprayers, shielded and hooded sprayers; Controlled droplet applicator (CDA) hand-held or boom-mounted applicators that produce a spray consisting of a narrow range of droplet size; Any and all greenhouse sprayers; Micro-sprinkler or drip irrigation systems; Chemigation.

One method of applying an active compound of the invention, or an agrochemical composition which contains at least one of said compounds, is foliar application. The frequency of application and the rate of application will depend on the risk of infestation by the corresponding pathogen. However, the active compounds can also penetrate the plant through the roots via the soil (systemic action) by drenching the locus of the plant with a liquid formulation, or by applying the compounds in solid form to the soil, e.g. in granular form (soil application). In crops of water such as rice, such granulates can be applied to the flooded rice field. The active compounds may also be applied to seeds (coating) by impregnating the seeds or tubers either with a liquid formulation of the fungicide or coating them with a solid formulation.

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, and germinated or soaked seeds.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

F. Combination Treatments

In some embodiments, methods of enhancing the effects of a microbicide (such as a microbicide comprising copper, e.g., Kocide® 2000 or Kocide® 3000 (DuPont™, with active ingredient copper hydroxide) are disclosed, comprising the step of applying an active compound in combination with a microbicide, the active compound being applied in an amount effective to enhance the effects of the microbicide.

In some embodiments, methods of enhancing the effects of a plant defense activator are disclosed, comprising the step of applying an active compound in combination with a plant defense activator, the active compound being applied in an amount effective to enhance the effects of the plant defense activator.

"Enhancing" the effects of a microbicide by applying an active compound in combination with the microbicide refers to increasing the effectiveness of the microbicide, such that the microorganism killing and/or growth inhibition is higher at a certain concentration of the microbicide applied in combination with the active compound than without. In some embodiments, a bacteria or other microorganism is "sensitized" to the effects of a microbicide, such that the bacteria or other microorganism that was resistant to the microbicide prior to applying the active compound (e.g., little to none, or less than 20, 10, 5 or 1% are killed upon application) is rendered vulnerable to that microbicide upon or after applying the active compound (e.g., greater than 20, 30, 40, 50, 60, 70, 80, 90, or 95% or more are killed).

Similarly, "enhancing" the effects of a plant defense activator by applying an active compound in combination with the plant defense activator refers to increasing the effectiveness of the plant defense activator, such that the microorganism killing and/or growth inhibition is higher at a certain concentration of the plant defense activator applied in combination with the active compound than without. In some embodiments, a bacteria or other microorganism is "sensitized" to the effects of a plant defense activator, such that the bacteria or other microorganism that was resistant to the effects of the plant defense activator prior to applying the active compound (e.g., little to none, or less than 20, 10, 5 or 1% are killed upon application) is rendered vulnerable to the effects of that plant defense activator upon or after applying the active compound (e.g., greater than 20, 30, 40, 50, 60, 70, 80, 90, or 95% or more are killed).

As used herein, the application of two or more compounds (inclusive of active compounds and microbicides) "in combination" means that the two compounds are applied closely enough in time that the application of or presence of one alters the biological effects of the other. The two compounds may be applied simultaneously (concurrently) or sequentially.

Simultaneous application of the compounds may be carried out by mixing the compounds prior to application, or by applying the compounds at the same point in time but at different sites of the plant or using different types of applications, or applied at times sufficiently close that the results observed are indistinguishable from those achieved when the compounds are applied at the same point in time.

Sequential application of the compounds may be carried out by applying, e.g., an active compound at some point in time prior to application of a microbicide, such that the prior application of active compound enhances the effects of the microbicide (e.g., percentage of microorganisms killed and/or slowing the growth of microorganisms). In some embodiments, an active compound is applied at some point in time prior to the initial application of a microbicide. Alternatively, the microbicide may be applied at some point in time prior to the application of an active compound, and optionally, applied again at some point in time after the application of an active compound.

EXAMPLES

Example 1

Synthesis of 2-Aminoimidazole-Triazole (2-AIT) Chemical Library

There is a paucity of reactions that have been reported to be compatible with 2-aminoimidazoles. To test the applicability of the Cu(I)-catalyzed [3+2] alkyne/azide cycloaddition (Click reaction, see Kolb et al., *Angewandte Chemie-International Edition* 2001, 11, 2004-2021; Rodionov et al., *Angewandte Chemie-International Edition* 2005, 15, 2210-2215), we synthesized the alkyne derived 2-aminoimidzole 1 and tested its ability to participate in a Cu(I)-catalyzed [3+2] cycloaddition with benzyl azide.

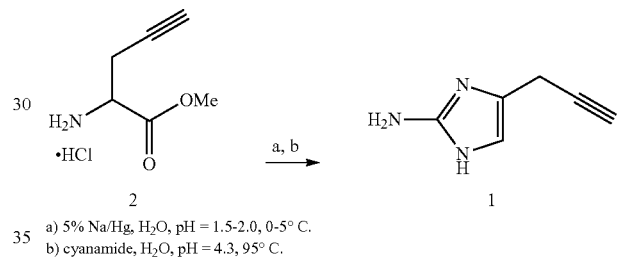

Scheme 1. Synthesis of alkyne 2-aminoimidazole 1.

a) 5% Na/Hg, $H_2O$, pH = 1.5-2.0, 0-5° C.
b) cyanamide, $H_2O$, pH = 4.3, 95° C.

The alkyne derived 2-aminoimidazole (2-AI) was synthesized as outlined in Scheme 1. Amino acid 2 (Kotha et al., *Tetrahedron* 2002, 45, 9203-9208) was subjected to small scale Akabori reduction (Akabori, *Berichte Der Deutschen Chemischen Gesellschaft* 1933, 66, 151-158), which, followed by condensation with cyanamide (Xu Yz et al., *J Org Chem* 1997, 3, 456-464) delivered the target alkyne 2-AI 1 in 88% yield. With 1 in hand, we explored various conditions to elicit the Cu-catalyzed [3+2] cycloaddition between 1 and benzyl azide (Table 1).

TABLE 1

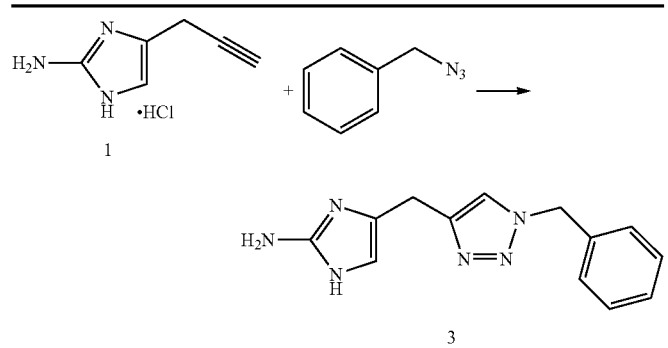

| Scale (mg) | Cu(I) Source[a] | Solvent | Base | Temp | Yield |
|---|---|---|---|---|---|
| 20 | CuI | THF | DIEA | RT | NR |
| 20 | CuI | THF | DIEA | 40° C. | NR |

TABLE 1-continued

| 20 | CuSO$_4$/NaAsc | EtOH/H$_2$O (1:1) | — | RT | NR |
| 20 | CuSO$_4$/NaAsc | EtOH/H$_2$O (1:1) | — | 40° C. | 86% |
| 100 | CuSO$_4$/NaAsc | EtOH/H$_2$O (1:1) | — | 40° C. | Decomp |
| 100 | CuSO$_4$/NaAsc | t-BuOH/H$_2$O/CH$_2$Cl$_2$ (1:1:1) | — | RT | 93% |

$^a$NaAsc = Sodium Ascorbate

Reactions in THF using Cu(I) yielded no reaction and only returned starting material. We then switched to using CuSO$_4$ and sodium ascorbate in a 1:1 solvent mixture of H$_2$O/EtOH. Again, no reaction was noted. However, when the reaction was heated to 40° C. we noted clean conversion to the desired 2-AIT conjugate 3 in 86% yield. Unfortunately, when the reaction was scaled up, we observed a significant amount of decomposition. Room temperature click reactions have been noted when a 1:1:1 solvent mixture of H$_2$O/EtOH/CH$_2$Cl$_2$ (Lee et al., *Tetrahedron Letters* 2006, 29, 5105-5109) is employed instead of the 1:1 H$_2$O/EtOH mixture. When these reaction conditions were tested, we observed conversion to 3 in 93% yield.

With the methodology established to access 2-AIT conjugates, we employed the synthetic approach outlined in Scheme 1 to synthesize 2-AI alkynes 4 and 5 in which we systematically extended the methylene space between the alkyne and the 2-AI. The click reaction was then performed between each of the 2-AI alkynes and 12 azides to yield an initial 2-AIT library (shown below). Each compound was characterized ($^1$H NMR, $^{13}$C NMR, HRMS).

In conclusion, we have developed a synthetic approach to access 2-aminoimidazole/triazole (2-AIT) conjugates that is underpinned by the Cu(I)-catalyzed [3+2] alkyne/azide cycloaddition. Using this chemistry we have assembled a focused library of 2-AIT conjugates.

1. Experimental Protocols for 2-AIT Conjugate Synthesis

All reagents used for chemical synthesis were purchased from commercially available sources and used without further purification. Chromatography was performed using 60 Å mesh standard grade silica gel from Sorbtech (Sorbent Technologies, Inc., Atlanta, Ga.). NMR solvents were obtained from Cambridge Isotope Laboratories, Inc. (Andover, Mass.) and used as received. $^1$H NMR (300 MHz or 400 MHz) and $^{13}$C NMR (75 MHz or 100 MHz) spectra were recorded at 25° C. on Varian Mercury spectrometers. Chemical shifts (δ) are given in ppm relative to tetramethylsilane or the respective NMR solvent; coupling constants (J) are in hertz (Hz). Abbreviations used are s=singlet, bs=broad singlet, d=doublet, dd=doublet of doublets, t=triplet, dt=doublet of triplets, bt=broad triplet, qt=quartet, m=multiplet, bm=broad multiplet and br=broad. High and low resolution mass spectra were obtained at the North Carolina State Mass Spectrometry Laboratory for Biotechnology. FAB experiments were carried out with a JOEL HX110HF mass spectrometer while ESI experiments were carried out on an Agilent LC-TOF mass spectrometers.

Chemical Library:

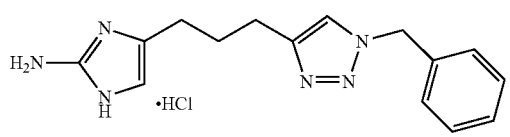

-continued

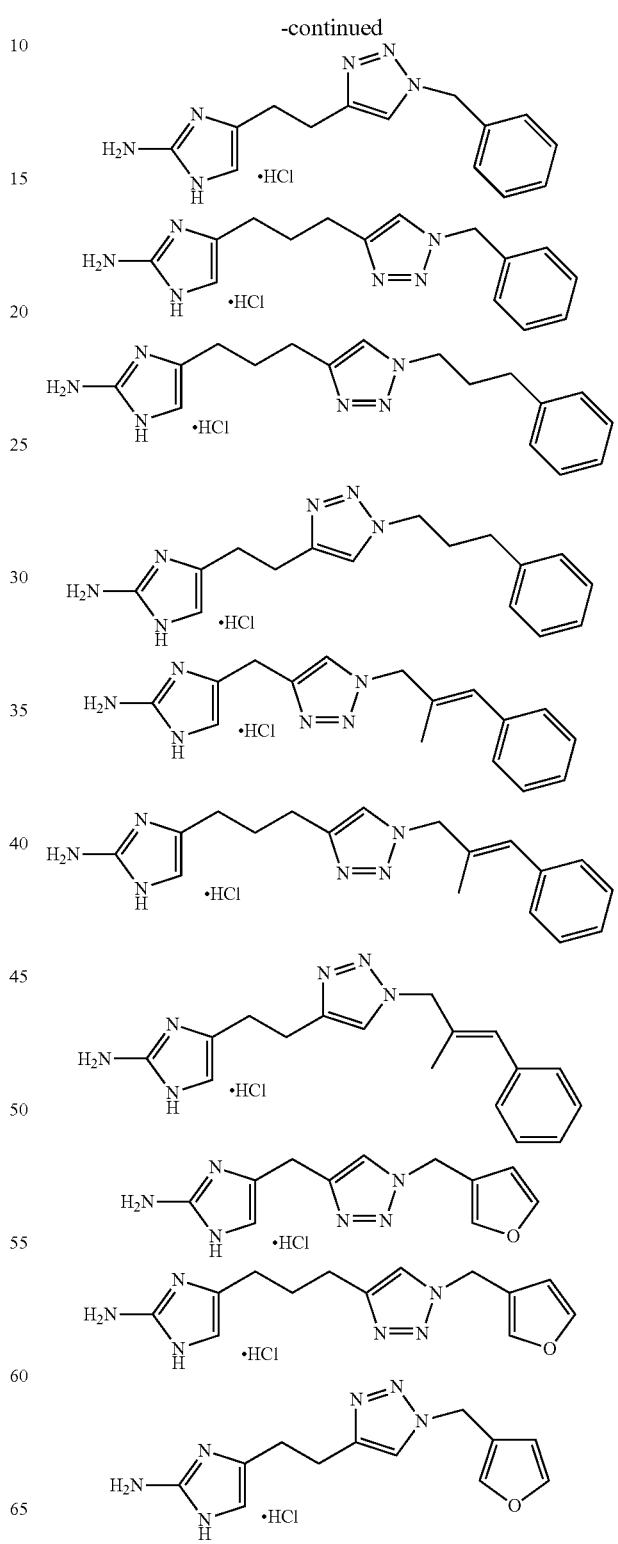

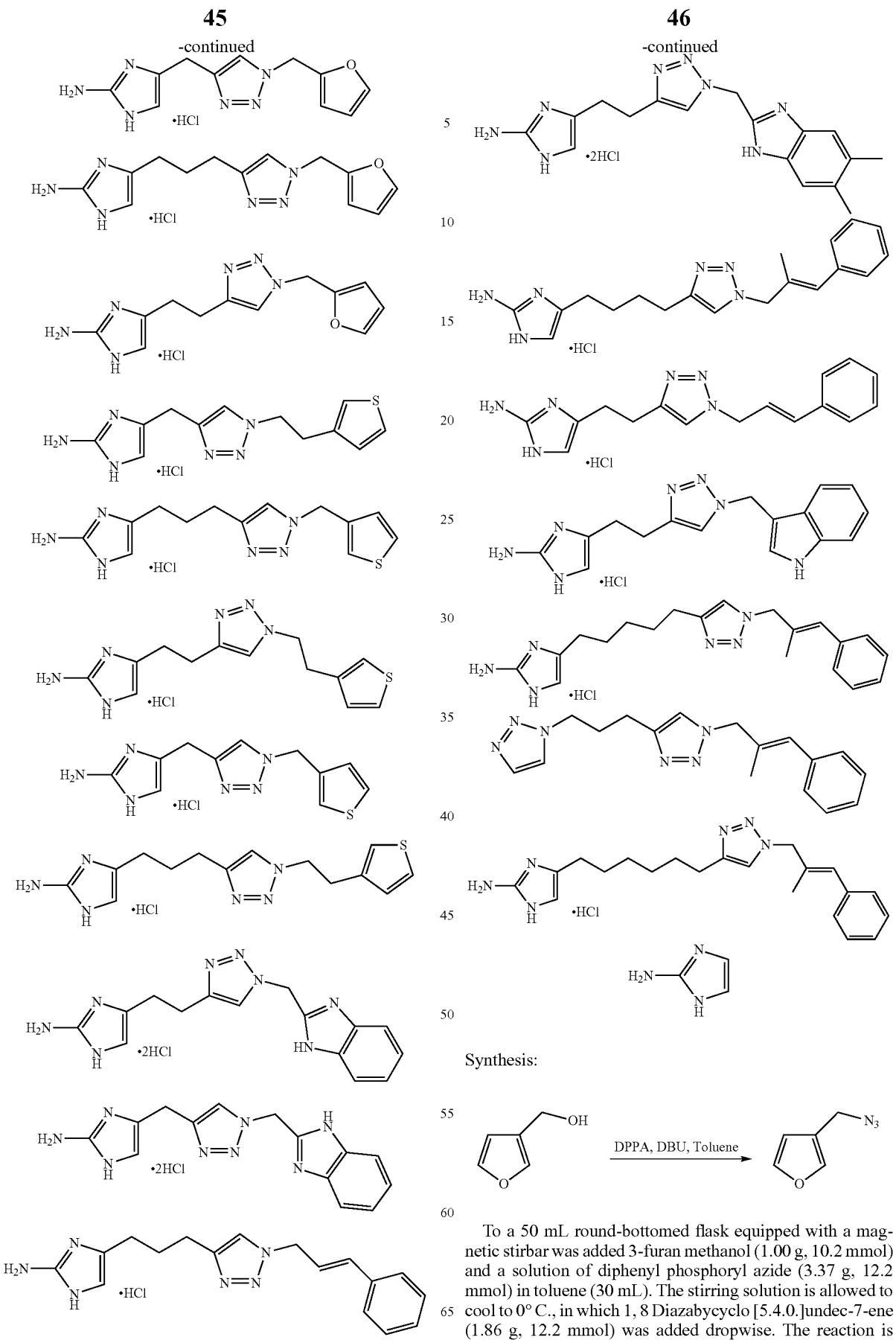
Synthesis:
To a 50 mL round-bottomed flask equipped with a magnetic stirbar was added 3-furan methanol (1.00 g, 10.2 mmol) and a solution of diphenyl phosphoryl azide (3.37 g, 12.2 mmol) in toluene (30 mL). The stirring solution is allowed to cool to 0° C., in which 1, 8 Diazabycyclo [5.4.0.]undec-7-ene (1.86 g, 12.2 mmol) was added dropwise. The reaction is allowed to slowly warm to ambient temperature for an additional 16 hours of stirring. After this period, the reaction mixture is washed with water (2×20 mL) and then with 5% HCl (20 mL). Volatiles are evaporated under reduced pressure. The resulting residue is then purified by column chromatography (1:9 ethyl acetate/hexane) providing 3-azidomethyl furan (1.19 g, 95%) as a colorless oil. $^1$H NMR (400 MHz, CDCl$_3$) δ 7.46 (d, 1H), δ 7.44 (s, 1H), δ 6.42 (d, 1H), δ 4.20 (s, 2H). ppm; $^{13}$C NMR (75 MHz, CDCl$_3$) δ 144.1, 141.1, 110.4, 92.1, 45.8 ppm; LRMS (EI) calcd for C$_5$H$_5$N$_3$O (M$_+$) 123. found 123.

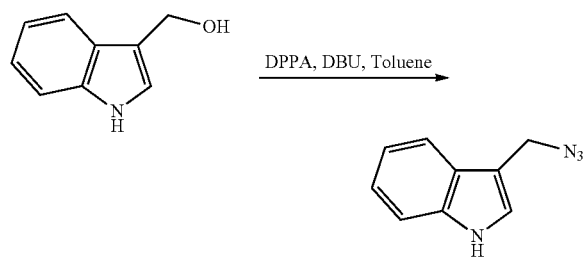

Following the same procedure used to synthesize 3-azidomethyl furan, indole-3-methanol (2.00 g, 13.6 mmol) was converted to 3-azodomethyl indole (1.31 g, 56%) as a yellow oil. $^1$H NMR (300 MHz, CDCl$_3$) δ 8.19 (bs, 1H), δ 7.71 (d, 1H), δ 7.39 (m, 2H), δ 7.19 (m, 2H), δ 4.54 (s, 2H) ppm; $_{13}$C NMR (75 MHz, CDCl$_3$) δ 130.3, 125.9, 125.3, 122.2, 120.3, 120.3, 119.7, 118.7, 111.9 ppm; LRMS (EI) calcd for C$_9$H$_8$N$_4$ (M$_+$) 172. found 172.

Following the same procedure used to synthesize 3-azidomethyl furan, furfuryl alcohol (2.50 g, 25.5 mmol) was converted to 2-azidomethyl furan (2.96 g, 95%) as a colorless oil. $^1$H NMR (300 MHz, CDCl$_3$) δ 7.43 (d, 1H), δ 6.36 (m, 2H), δ 4.29 (s, 2H) ppm; $_{13}$C NMR (75 MHz, CDCl$_3$) δ 148.2, 110.7, 109.6, 47.2 ppm; LRMS (EI) calcd for C$_5$H$_5$N$_3$O (M$_+$) 123. found 123.

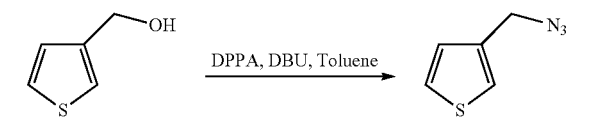 [SMILES: OCc1ccsc1 ; [N-]=[N+]=NCc1ccsc1]

Following the same procedure used to synthesize 3-azidomethyl furan, thiophene-3-methanol (3.14 g, 27.6 mmol) was converted to 3-azidomethyl thiophene (3.72 g, 97%) as a colorless oil. $^1$H NMR (300 MHz, CDCl$_3$) δ 7.38 (d, 1H), δ 7.23 (s, 1H), δ 7.10 (d, 1H), δ 4.36 (s, 2H) ppm; $^{13}$C (75 MHz, CDCl$_3$) δ 136.4, 127.6, 127.1, 124.0, 49.9 ppm; LRMS (EI) calcd for C$_5$H$_5$N$_3$S (M$_+$) 139. found 139.

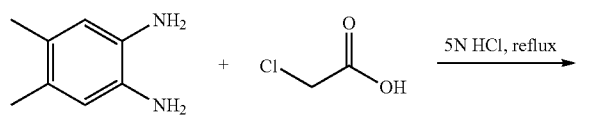

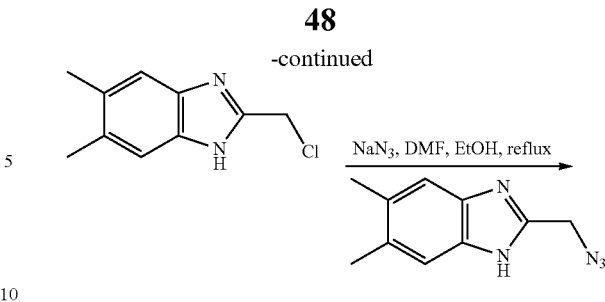

2-chloroethyl-5,6-dimethyl-1H-benzimidazole was synthesized through the treatment of 4,5-dimethyl-1,2-phenylenediamine to conditions outlined by Hortelano (Raban et al., Org. Chem. 1985, 50 (13), 2205-2210). The resulting product was transformed to 2-azidomethyl-5,6-dimethyl-1H-benzimidazole following conditions outlined by Hankovszky resulting in a yellow solid (Hiales et al., Synthesis 1978, 4, 313-315). H NMR (300 MHz, CDCl$_3$) δ 7.26 (s, 2H), δ 4.72 (s, 2H), δ 2.37 (s, 6H) ppm; $_{13}$C NMR (75 MHz, DMSO) δ 153.7, 134.3, 130.1, 125.1, 124.6, 117.2, 113.6, 48.0, 20.6, 19.6 ppm; HRMS (FAB) calcd for C$_{10}$H$_{11}$N$_5$ (M$_+$) 201.1014. found 201.1010.

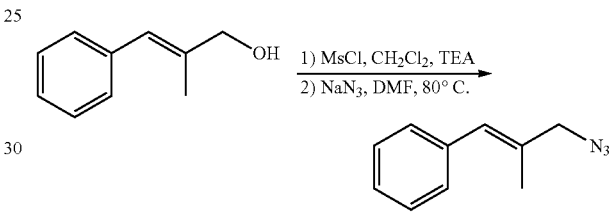

To a 100 mL round-bottomed flask equipped with a magnetic stir was added trans-2-methyl-3-phenyl-2-propen-1-ol (2.00 g, 13.5 mmol) and 75 mL of methylene chloride. The solution was then cooled to 0° C. while stirring. Then, triethylamine (2.75 g, 27.0 mmol) is added followed by a dropwise addition of methanesulfonyl chloride (2.34 g, 20.4 mmol) and a two hour stir period. The reaction mixture is washed with water (2×75 mL), dried with sodium sulfate and then concentrated de vacuo. The crude mixture is then dissolved in 75 mL of DMF and then stirred via magnetic stir bar. To this mixture, sodium azide (1.76 g, 27.0 mmol) is added. The reaction mixture is then heated to 80° C. and allowed to stir for two hours. At this time, volatiles are concentrated de vacuo and the resulting residue is purified via column chromatography (1:9 ethyl acetate/hexane) providing (3-Azido-2-methyl propenyl)-benzene (2.08 g, 89%) as a colorless oil. $_1$H NMR (300 MHz, CDCl$_3$) δ 7.36-7.25 (m, 5H), δ 6.53 (s, 1H), δ 3.87 (s, 2H) ppm; $_{13}$C NMR (75 MHz, CDCl$_3$) δ 129.4, 129.2, 128.9, 128.6, 128.4, 127.1, 59.9, 52.0, 22.3, 16.5 ppm; LRMS (EI) calcd for C$_{10}$H$_{11}$N$_3$(M$_+$) 173. found 173.

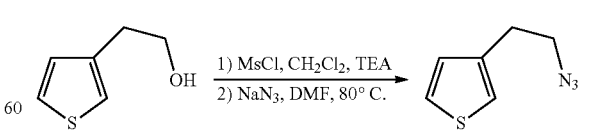

Following the same procedure used to synthesize (3-Azido-2-methyl-propenyl) benzene, thiophene-3-ethanol (2.00 g, 15.5 mmol) was converted to 3-azidoethyl-thiophene (2.06 g, 86%) as a colorless oil. $_1$H NMR (300 MHz, CDCl$_3$) δ 7.36 (s, 1H), δ 7.14 (d, 1H), δ 7.04 (d, 1H), δ 3.54 (t, 2H), δ

2.98 (t, 2H) ppm; $_{13}$C NMR (75 MHz, CDCl$_3$) δ 138.7, 128.4, 126.3, 122.2, 52.0, 30.1 ppm; LRMS (EI) calcd for C$_6$H$_7$N$_3$S (M$_+$) 153. found 153.

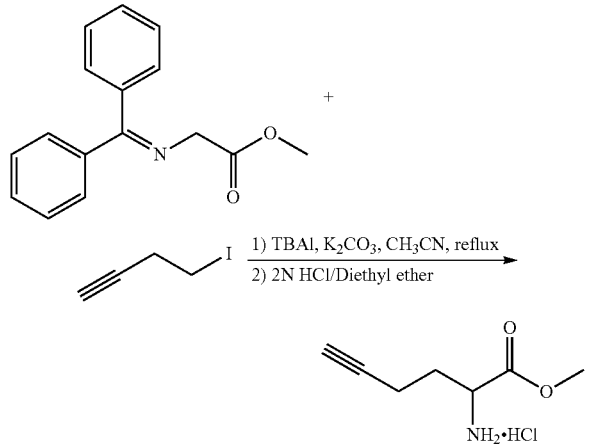

2-Amino-hex-5-ynoic acid methyl ester hydrochloride was synthesized using the same methods previously reported for the synthesis of 2-Amino-pent-4-ynoic acid methyl ester hydrochloride (Kotha et al., Tetrahedron 2002, 58, 9203-9208). $_1$H NMR (300 MHz, D$_2$O) δ 4.16 (t, 1H), δ 3.71 (s, 3H), δ 2.32 (t, 1H), δ 2.29 (m, 2H), δ 2.06 (m, 2H) ppm; $_{13}$C NMR (75 MHz, D$_2$O) δ 170.4, 82.4, 71.4, 53.9, 52.1, 28.7, 14.4 ppm; HRMS (ESI) calcd for C$_7$H$_{11}$NO$_2$ (M$_+$) 142.0859. found 142.862.

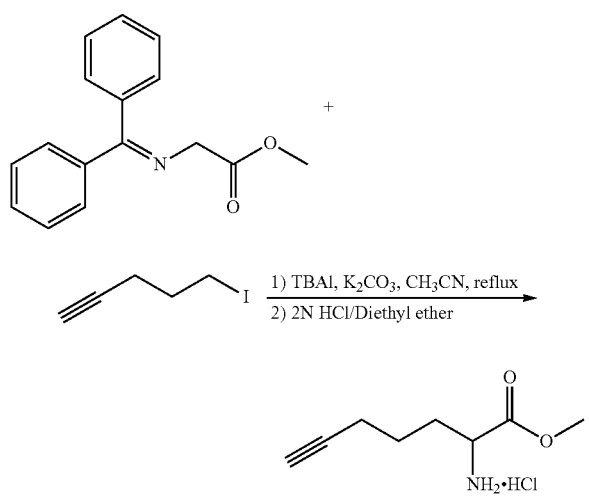

2-Amino-hept-6-ynoic acid methyl ester hydrochloride was synthesized using the same methods previously reported for the synthesis of 2-Amino-pent-4-ynoic acid methyl ester hydrochloride (Kotha et al., Tetrahedron 2002, 58, 9203-9208). $_1$H NMR (300 MHz, DMSO) δ 8.75 (s, 2H), δ 3.99 (m, 1H), δ 3.72 (s, 3H), δ 2.82 (t, 1H), δ 2.17 (m, 2H), δ 1.89 (m, 2H), δ 1.51 (m, 2H) ppm; $_{13}$C NMR (75 MHz, DMSO) δ 163.7, 83.1, 69.2, 60.9, 30.6, 29.5, 23.9, 17.6 ppm; HRMS (ESI) calcd for C$_8$H$_{13}$NO$_2$ (M$_+$) 156.1019. found 156.1017.

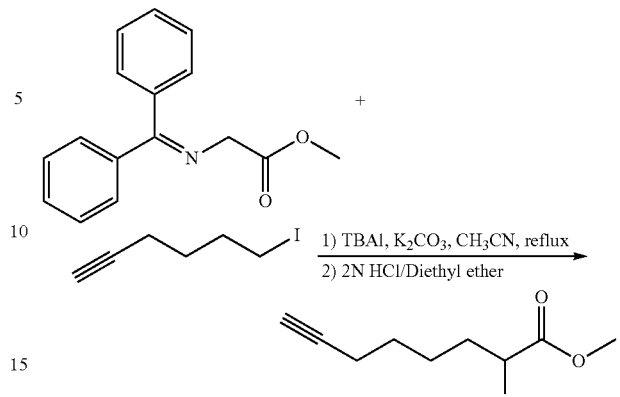

2-Amino-oct-7-ynoic acid methyl ester hydrochloride was synthesized using the same methods previously reported for the synthesis of 2-Amino-pent-4-ynoic acid methyl ester hydrochloride (Kotha et al., Tetrahedron 2002, 58, 9203-9208). $_1$H NMR (300 MHz, D$_2$O) 4.16 (t, 1H), δ 3.84 (s, 31-1), δ 2.35 (t, 1H), δ 2.24 (m, 21-1), δ 1.95 (m, 2H), δ 1.52 (m, 4H) ppm; $_{13}$C NMR (75 MHz, D$_2$O) δ 170.9, 85.6, 69.6, 53.6, 52.9, 29.3, 27.0, 23.4, 17.3 ppm; HRMS (ESI) calcd for C$_9$H$_{15}$NO$_2$(M$_+$) 170.1176. found 170.1171.

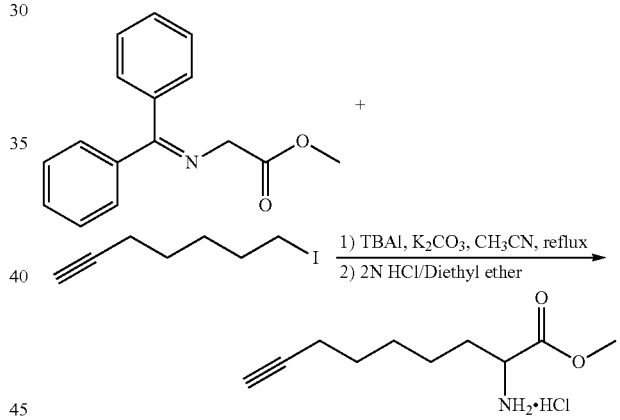

2-Amino-non-8-ynoic acid methyl ester hydrochloride was synthesized using the same methods previously reported for the synthesis of 2-Amino-pent-4-ynoic acid methyl ester hydrochloride (Kotha et al., Tetrahedron 2002, 58, 9203-9208). $_1$H NMR (300 MHz, D$_2$O) δ 4.21 (t, 1H), δ 3.90 (s, 3H), δ 2.41 (t, 1H), δ 2.28 (m, 2H), δ 2.01 (m, 2H), δ 1.51 (m, 6H) ppm; $_{13}$C NMR (75 MHz, D$_2$O) δ 171.1, 86.4, 69.4, 53.7, 53.1, 29.8, 27.5, 27.4, 23.8, 17.6 ppm; HRMS (ESI) calcd for C$_{10}$H$_{18}$NO$_2$(M$_+$) 184.1332. found 184.1329.

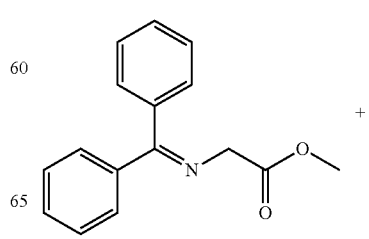

-continued

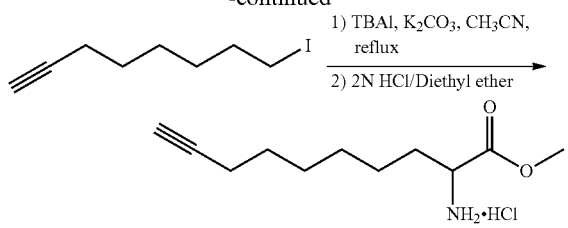

2-Amino-dec-9-ynoic acid methyl ester hydrochloride was synthesized using the same methods previously reported for the synthesis of 2-Amino-pent-4-ynoic acid methyl ester hydrochloride (Kotha et al., Tetrahedron 2002, 58, 9203-9208). $_1$H NMR (300 MHz, D$_2$O) δ 4.16 (t, 1H), δ 3.86 (s, 3H), δ 2.36 (t, 1H), δ 2.21 (m, 2H), δ 1.98 (m, 2H), δ 1.55-1.39 (m, 8H) ppm; $_{13}$C NMR (75 MHz, D$_2$O) δ 171.2, 86.7, 69.3, 53.7, 53.1, 29.8, 27.7, 27.7, 27.6, 24.1, 17.6 ppm; HRMS (ESI) calcd for C$_{11}$H$_{20}$NO$_2$(M$_+$) 198.1488. found 198.1488.

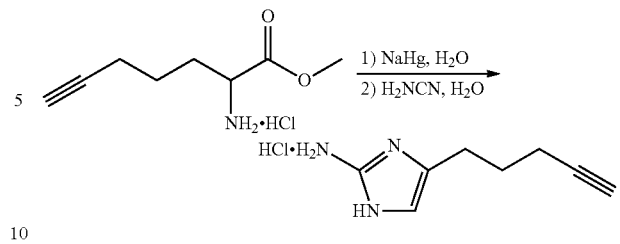

2-Amino-hept-6-ynoic acid methyl ester hydrochloride (2.00 g, 10.4 mmol) was treated to an Akabori reduction followed by a cyanamide condensation employing conditions previously reported to produce 4-Pent-4-ynyl-1H-imidazol-2-ylamine hydrochloride (1.75 g, 90%) as a pale oil (Olofson et al., Journal of Organic Chemistry 1997, 62, (23), 7918-7919). $_1$H NMR (300 MHz, CDCl$_3$) δ 6.68 (bs, 2H), δ 6.24 (s, 1H), δ 2.51 (t, 2H), δ 2.17 (t, 1H), δ 1.95 (s, 1H), δ 1.74 (m, 2H) ppm; $_{13}$C NMR (75 MHz, CDCl$_3$) δ 148.3, 132.7, 111.6, 84.4, 69.1, 28.0, 26.0, 18.2 ppm; HRMS (ESI) calcd for C$_{10}$H$_{16}$N$_3$ (M$_+$) 150.1026. found 150.1029.

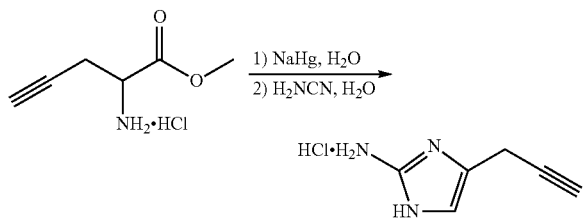

2-Amino-pent-4-ynoic acid methyl ester hydrochloride (2.91 g, 17.8 mmol) was treated to an Akabori reduction followed by a cyanamide condensation employing conditions previously reported to produce 4-Prop-2-ynyl-1H-imidazol-2-ylamine hydrochloride (1.65 g, 59%) as a yellow oil (Olofson et al., Journal of Organic Chemistry 1997, 62, (23), 7918-7919). $_1$H NMR (300 MHz, CD$_3$OD) δ 6.30 (s, 1H), δ 5.02 (d, 2H), δ 2.26 (t, 1H) ppm; $_{13}$C NMR (75 MHz, CD$_3$OD) δ 150.1, 127.2, 109.6, 83.6, 69.8, 15.9 ppm; HRMS (ESI) calcd for C$_6$H$_7$N$_3$ (M$_+$) 122.0712. found 122.0713.

2-Amino-oct-7-ynoic acid methyl ester hydrochloride (2.90 g, 14.1 mmol) was treated to an Akabori reduction followed by a cyanamide condensation employing conditions previously reported to produce 4-Hex-5-ynyl-1H-imidazol-2-ylamine hydrochloride (2.45 g, 87%) as a pale yellow solid (Olofson et al., Journal of Organic Chemistry 1997, 62, (23), 7918-7919). $_1$H NMR (300 MHz, CD$_3$OD) δ 6.43 (s, 1H), δ 2.44 (t, 2H), 2.14 (t, 1H), δ 2.12 (m, 2H), δ 1.64 (m, 2H), δ 1.47 (m, 2H) ppm; $_{13}$C NMR (75 MHz, CD$_3$OD) δ 147.3, 127.6, 108.5, 83.4, 68.7, 27.7, 27.1, 23.8, 17.5 ppm; HRMS (ESI) calcd for C$_9$H$_{14}$N$_3$ (M$_+$) 164.1182. found 164.1182.

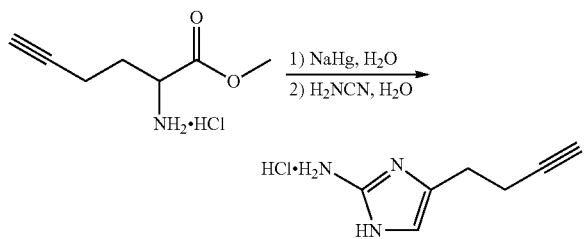

2-Amino-hex-5-ynoic acid methyl ester hydrochloride (2.53 g, 14.2 mmol) was treated to an Akabori reduction followed by a cyanamide condensation employing conditions previously reported to produce 4-But-3-ynyl-1H-imidazol-2-ylamine hydrochloride (1.17 g, 48%) as a pale yellow oil (Olofson et al., Journal of Organic Chemistry 1997, 62, (23), 7918-7919). $_1$H NMR (300 MHz, CD$_3$OD) δ 6.52 (s, 1H), δ 2.61 (t, 2H), δ 2.42 (m, 2H), δ 2.27 (t, 1H) ppm; $_{13}$C NMR (75 MHz, CD$_3$OD) δ 147.4, 126.2, 109.4, 81.9, 69.9, 23.8, 17.4 ppm; HRMS (ESI) calcd for C$_7$H$_{10}$N$_3$(M$_+$) 136.0869. found 136.0865.

2-Amino-non-8-ynoic acid methyl ester hydrochloride (2.02 g, 9.20 mmol) was treated to an Akabori reduction followed by a cyanamide condensation employing conditions previously reported to produce 4-Hept-6-ynyl-1H-imidazol-2-ylamine hydrochloride (1.04 g, 53%) as a pale yellow solid (Olofson et al., Journal of Organic Chemistry 1997, 62, (23), 7918-7919). $_1$H NMR (300 MHz, CD$_3$OD) δ 6.17 (s, 1H), δ 2.19 (t, 2H), δ 1.90 (t, 1H), δ 1.86 (m, 2H), δ 1.24-1.13 (m, 6H) ppm; $_{13}$C NMR (75 MHz, CD$_3$OD) δ 147.5, 128.3, 108.8, 83.8, 65.5, 28.4, 28.3, 28.2, 24.5, 17.8 ppm; HRMS (ESI) calcd for C$_{10}$H$_{16}$N$_3$ (M$_+$) 178.1338. found 178.1337.

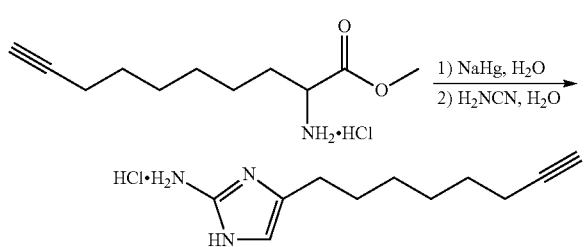

2-Amino-dec-9-ynoic acid methyl ester hydrochloride (1.50 g, 6.42 mmol) was treated to an Akabori reduction followed by a cyanamide condensation employing conditions previously reported to produce 4-Oct-7-ynyl-1H-imidazol-2-ylamine hydrochloride (0.774 g, 53%) as a pale yellow solid (Olofson et al., Journal of Organic Chemistry 1997, 62, (23), 7918-7919). $_1$H NMR (400 MHz, CD$_3$OD) δ 6.09 (s, 1H), δ 2.19 (t, 2H), δ 1.95 (t, 1H), 1.93 (m, 2H), δ 1.39-1.11 (m, 8H) ppm; $_{13}$C NMR (75 MHz, CD$_3$OD) δ 148.5, 131.0, 110.1, 83.9, 68.3, 28.6, 28.5, 28.4, 28.3, 25.7, 17.8 ppm; HRMS (ESI) calcd for C$_{11}$H$_{18}$N$_3$ (M$_+$) 192.1495. found 192.1495.

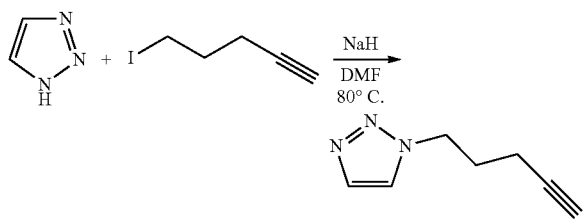

To a 50 mL round-bottomed flask equipped with a magnetic stirbar was added 1-H-1,2,3-triazole (0.192 g, 2.78 mmol) and DMF (10 mL) and then cooled to 0° C. while stirring. Then, sodium hydride (60% dispersion in mineral oil) (0.133 g, 3.33 mmol) is added to the reaction mixture and was slowly allowed to warm to ambient temperature. Then, 1-iodo-4 pentyne (0.647 g, 3.33 mmol) was added dropwise. The reaction mixture was then heated to 80° C. and allowed to stir for 2.5 hours. Water (20 mL) was then added to the reaction mixture and then extracted with ethyl acetate (2×20 mL) The organic phase was dried with sodium sulfate and concentrated. de vacuo followed by a purification by column chromatography (ethyl acetate/hexane) to produce 1-Pent-4-ynyl-1H-[1,2,3]triazole (0.349 g, 93%) as a colorless oil. $_1$H NMR (300 MHz, CDCl$_3$) δ 7.67 (s, 1H), δ 7.59 (s, 1H), δ 4.53 (t, 2H), δ 2.20 (t, 2H), δ 2.17 (m, 2H), δ 2.04 (s, 1H) ppm; $_{13}$C NMR (75 MHz, CDCl$_3$) δ 133.9, 123.9, 82.2, 70.4, 48.7, 28.9. 15.7 ppm; HRMS (ESI) calcd for C$_7$H$_{10}$N$_3$ (M$_+$) 136.0869. found 136.0866.

General Procedure for Click Reactions:

The terminal alkyne (1.0 equiv.) was dissolved in a 1:1:1 mixture of tert-butyl alcohol, water and methylene chloride (ca. 10 mL per 0.300 g of terminal alkyne). To this solution, the appropriate azide (1.2 equiv.) was added while stirring vigorously at room temperature. Copper (II) sulfate pentahydrate (15 mol %) and sodium ascorbate (45 mol %) were then added sequentially to the solution. Reaction mixtures were allowed to stir until completion via TLC analysis (12-24 hrs). The solvents were then removed de vacuo in which the resulting residue was dissolved in methanol and purified by flash chromatography (10-20% ammonia saturated methanol:methylene chloride). The resulting fractions were evaporated under reduced pressure followed by a 24 hr high vacuum treatment to remove all ammonia traces. Methanol saturated with HCl is then added to the purified product in which all volatiles are then removed under reduced pressure.

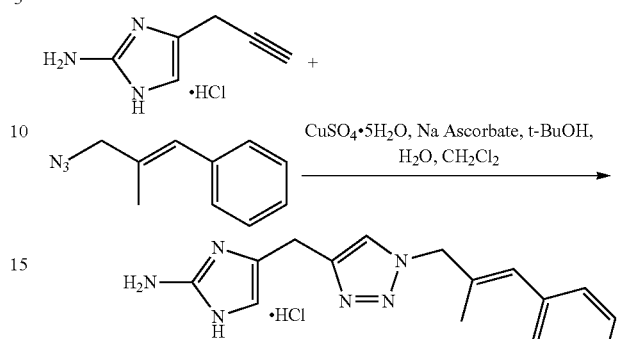

4-Prop-2-ynyl-1H-imidazol-2-ylamine hydrochloride (0.127 g, 0.809 mmol) was reacted with (3-Azido-2-methyl-propenyl)-benzene (0.168 g, 0,971 mmol) following the general procedure for click reactions outlined above to produce 4-[1-(2-Methyl-3-phenyl-allyl)-1H [1,2,3]triazol-4-ylmethyl]-1H-imidazol-2-ylamine hydrochloride (0.244 g, 91%) of a pale yellow solid. $_1$H NMR (300 MHz, D$_2$O) δ 7.94 (s, 1H), δ 7.40-7.35 (m, 5H), δ 6.56 (s, 1H), δ 5.10 (s, 2H), δ 3.99 (s, 2H), δ 1.76 (s, 3H) ppm; $_{13}$C δ 145.8, 138.1, 136.9, 136.5, 136.4, 132.8, 128.3, 128.0, 127.6, 125.3, 123.4, 49.3, 23.8, 23.4; HRMS (ESI) calcd for C$_{16}$H$_{18}$N$_6$ (M$_+$) 295.1665. found 295.1665.

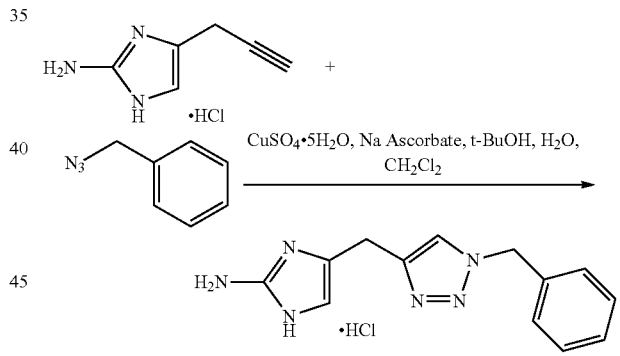

4-Prop-2-ynyl-1H-imidazol-2-ylamine hydrochloride (0.095 g, 0.603 mmol) was reacted with benzyl azide (0.096 g, 0.723 mmol) following the general procedure for click reactions outlined above to produce 4-(1-Benzyl-1H-[1,2,3]triazol-4-ylmethyl)-1H-imidazol 2-ylamine hydrochloride (0.151 g, 86%) of a pale yellow solid. $_1$H NMR (300 MHz, D$_2$O) δ 7.79 (s, 1H), δ 7.42-7.35 (m, 5H), δ 6.43 (s, 1H), δ 5.58 (s, 21-1), δ 3.86 (s, 2H) ppm; $_{13}$C δ 145.4, 136.6, 136.4, 128.8, 128.7, 126.9, 126.8, 126.3, 124.1, 121.8, 109.6, 53.3, 24.1 ppm; HRMS (ESI) calcd for C$_{13}$H$_{16}$N$_6$O (M$_+$) 254.1352. found 254.1352.

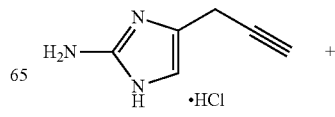

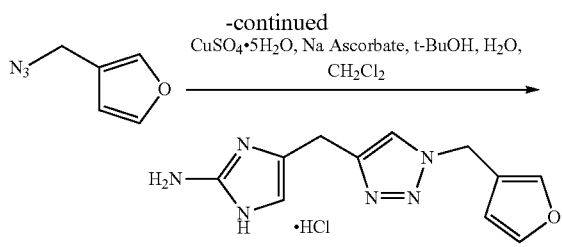

4-Prop-2-ynyl-1H-imidazol-2-ylamine hydrochloride (0.101 g, 0.639 mmol) was reacted with 3-azidomethyl-furan (0.094 g, 0.767 mmol) following the general procedure for click reactions outlined above to produce 4-(1-Furan-3-ylmethyl-1H-[1,2,3]triazol-4-ylmethyl)-1H-imidazol-2-ylamine hydrochloride (0.077 g, 43%) of a pale yellow solid. $_1$H NMR (300 MHz, CD$_3$OD) δ 8.12 (s, 1H), δ 7.60 (s, 1H), δ 7.38 (s, 1H), δ 6.53 (s, 1H), δ 6.37 (s, 1H), δ 5.46 (s, 2H), δ 3.95 (s, 2H) ppm; $_{13}$C NMR (75 MHz, CD$_3$OD) δ 146.1, 145.3, 144.1, 141.0, 123.3, 123.1, 110.3, 110.2, 109.9, 51.3, 19.9 ppm; HRMS (ESI) calcd for C$_{11}$H$_{12}$N$_6$O (M$_+$) 244.1145. found 244.1145.

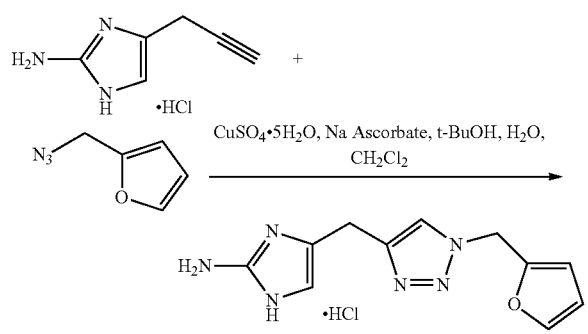

4-Prop-2-ynyl-1H-imidazol-2-ylamine hydrochloride (0.096 g, 0.061 mmol) was reacted with 2-azidomethyl-furan (0.089 g, 0.729 mmol) following the general procedure for click reactions outlined above to produce 4-(1-Furan-2-ylmethyl-1H-[1,2,3]triazol-4-ylmethyl)-1H-imidazol-2-ylamine hydrochloride (0.078 g, 46%) as a pale yellow solid. $_1$H NMR (300 MHz, CD$_3$OD) δ 7.93 (s, 1H), δ 7.41 (s, 1H), 6.49 (s, 2H), δ 6.32 (s, 1H), δ 5.56 (s, 2H), δ 3.89 (s, 2H) ppm; $_{13}$C NMR (75 MHz, CD$_3$OD) δ 146.2, 146.1, 142.4, 141.5, 122.3, 122.2, 108.9, 109.2, 108.8, 51.6, 18.9 ppm; HRMS (ESI) calcd for C$_{11}$H$_{12}$N$_6$O (M$_+$) 245.1145. found 245.1147.

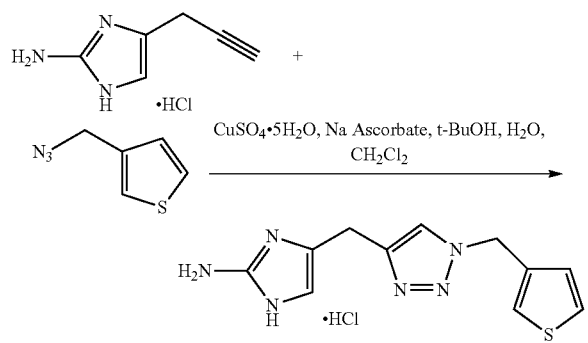

4-Prop-2-ynyl-1H-imidazol-2-ylamine hydrochloride (0.096 (0.061 mmol) was reacted with 3-azidomethyl thiophene (0.102 g, 0.732 mmol) following the general procedure for click reactions outlined above to produce 4-(1-Thiophen-3-ylmethyl-1H-[1,2,3]triazol-4-ylmethyl)-1Himidazol-2-ylamine hydrochloride (0.079 g, 44%) of a pale yellow solid. $_1$H NMR (300 MHz, CD$_3$OD) δ 8.18 (s, 1H), δ 7.44 (s, 1H), δ 7.30 (d, 1H), δ 6.98 (d, 1H), δ 6.53 (s, 1H), δ 5.57 (s, 2H), δ 3.95 (s, 2H) ppm; $_{13}$C (75 MHz, CD$_3$OD) δ 145.7, 145.1, 143.7, 139.7, 129.8, 121.8, 111.5, 109.8, 109.2, 52.7, 21.5 ppm; HRMS (ESI) calcd for C$_{11}$H$_{12}$N$_6$S (M$_+$) 260.0919. found 260.0919.

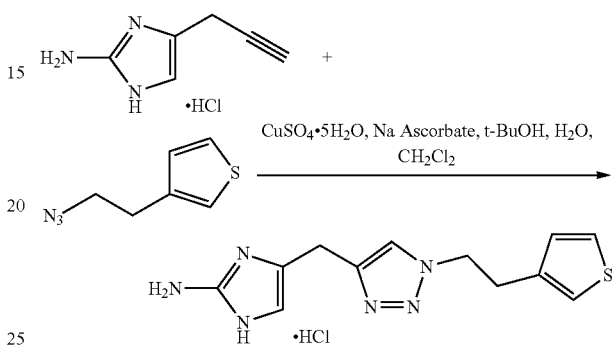

4-Prop-2-ynyl-1H-imidazol-2-ylamine hydrochloride (0.101 g, 0.641 mmol was reacted with 3-(2-Azido-ethyl)-thiophene (0.118 g, 0.769 mmol) following the general procedure for click reactions outlined above to produce 4-[1-(2-Thiophen-3-yl-ethyl)-1H [1,2,3]triazol-4-ylmethyl]-1H-imidazol-2-ylamine hydrochloride (0.119 g, 60%) of a pale yellow solid. $_1$H NMR (300 MHz, CD$_3$OD) δ 7.42 (s, 1H), δ 7.19 (t, 1H), δ 6.90 (s, 1H), □ 6.78 (d, 1H), S 6.09 (s, 1H), δ 4.47 (t, 2H), δ 3.67 (s, 2H), δ 3.09 (t, 2H) ppm; $_{13}$C; (75 MHz, CD$_3$OD) δ 151.2, 145.7, 137.7, 130.5, 127.8, 125.8, 122.9, 121.9, 110.3, 50.798, 30.7, 23.3 ppm; HRMS (ESI) calcd for C$_{12}$H$_{14}$N$_6$S (M$_+$) 274.1001. found 274.1007.

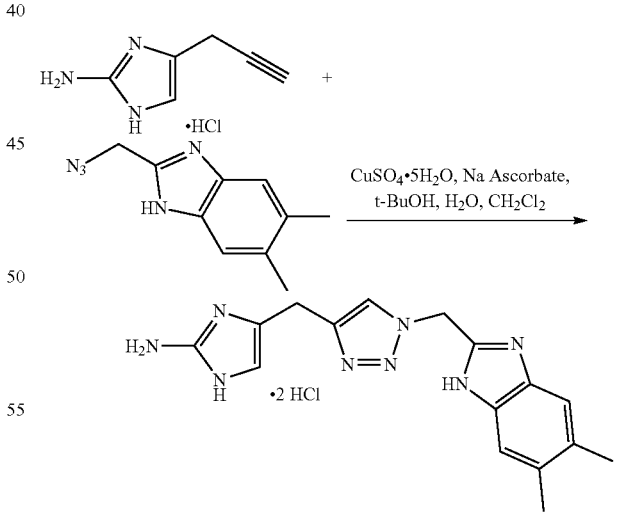

4-Prop-2-ynyl-1H-imidazol-2-ylamine hydrochloride (0.047 g, 0.295 mmol) was reacted with 2-azidomethyl-5,6-dimethyl-1H-benzimidazole (0.071 g, 0.354 mmol) following the general procedure for click reactions outlined above to produce 4-[1-(5,6 Dimethyl-1H-benzoimidazol-2-ylmethyl)-1,1-[1,2,3]triazol-4-ylmethyl]-1H-imidazol-2-ylamine dihydrochloride (0.029 g, 25%) of a yellow solid. $_1$H NMR (300 MHz, CD$_3$OD) δ 8.09 (s, 1H), δ 7.45 (s, 2H), δ 6.52 (s, 1H), δ 6.08 (s, 2H), δ 3.93 (s, 2H), δ 2.35 (s, 6H) ppm; $_{13}$C (75 MHz, CD$_3$OD) δ 142.2, 136.9, 136.6, 124.5, 124.3, 113.8, 113.4, 110.0, 100.4, 85.8, 80.6, 75.3, 74.1, 45.0, 20.9, 19.28 ppm; HRMS (ESI) calcd for C$_{16}$H$_{18}$N$_8$ (M$_+$) 323.1727. found 323.1734.

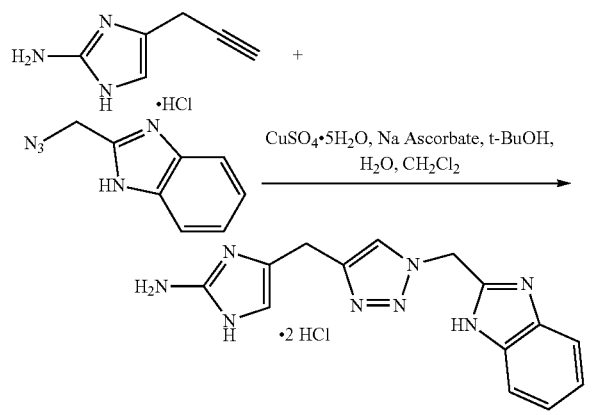

4-Prop-2-ynyl-1H-imidazol-2-ylamine hydrochloride (0.091 g, 0.576 mmol) was reacted with 2-azidomethyl-1H-benzimidazole, which was synthesized using previously reported methods (Hiales et al., Synthesis 1978, 4, 313-315), (0.120 g, 0.691 mmol) following the general procedure for click reactions outlined above to produce 4-[1-(1H-Benzoimidazol-2-ylmethyl)-1H-[1,2,3]triazol-4-ylmethyl] 1Himidazol-2-ylamine dihydrochloride (0.125 g, 59%) of a yellow solid. $_1$H NMR (300 MHz, CD$_3$OD) δ 8.01 (s, 1H), δ 7.58 (d, 2H), δ 7.31 (t, 2H), δ 6.44 (s, 1H), δ 5.98 (s, 2H) δ 3.84 (s, 2H) ppm; $_{13}$C (75 MHz, CD$_3$OD) δ 135.6, 124.7, 123.7, 123.5, 122.8, 112.8, 112.3, 108.4, 83.6, 78.9, 74.0, 73.2, 44.2, 19.3 ppm; HRMS (ESI) calcd for C$_{14}$H$_{14}$N$_8$ (M$_+$) 295.1414. found 295.1420.

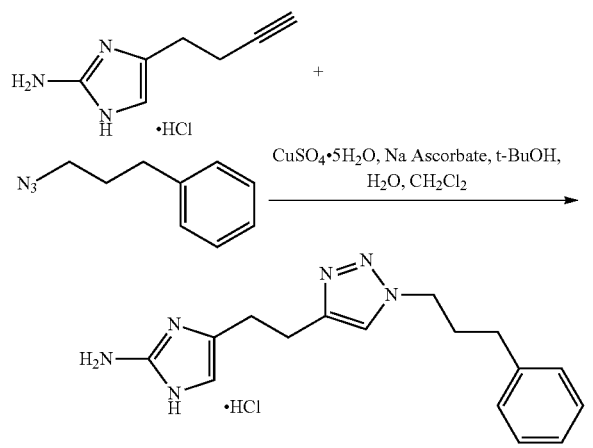

4-But-3-ynyl-1H-imidazol-2-ylamine hydrochloride (0.0735 g, 0.428 mmol) was reacted with (3-azido-propyl) benzene, which was synthesized using previously reported methods (Suenaga et al., Tetrahedron Letters 2003, 44, 5799-5801), (0.083 g, 0.514 mmol) following the general procedure for click reactions outlined above to produce 4-{2-[1-(3-Phenyl-propyl)-1H-[1,2,3]triazol-4-yl]-ethyl}-1H-imidazol-2-ylamine hydrochloride (0.051 g, 36%) of a pale yellow oil. $_1$H NMR (300 MHz, CD$_3$OD) δ 7.87 (s, 1H), δ 7.32-7.22 (m, 5H), δ 6.54 (s, 1H), δ 4.31 (t, 2H), δ 3.05 (t, 2H), δ 2.93 (t, 2H), δ 2.67 (t, 2H), δ 2.23 (m, 2H) ppm; $_{13}$C (75 MHz CD$_3$OD) δ 153.3, 146.6, 140.4, 134.3, 128.8, 128.7, 128.6, 126.6, 121.5, 67.5, 53.9, 32.8, 32.9, 29.5 ppm; HRMS (ESI) calcd for C$_{16}$H$_{20}$N$_6$ (M$_+$) 296.1822. found 296.1828.

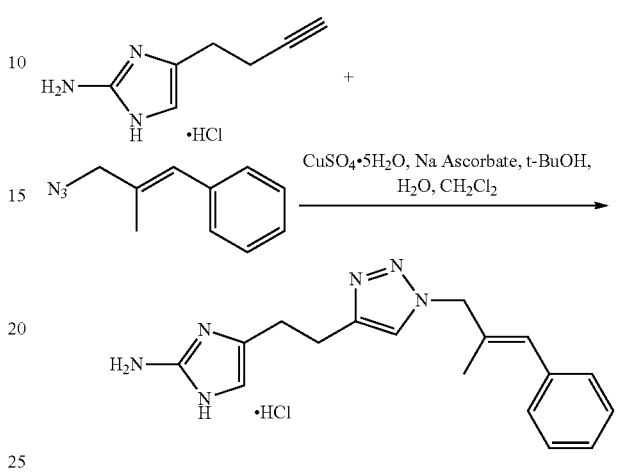

4-But-3-ynyl-1H-imidazol-2-ylamine hydrochloride (0.062 g, 0.362) was reacted with (3-Azido-2-methyl-propenyl)-benzene (0.075 g, 0.434 mmol) following the general procedure for click reactions outlined above to produce 4-{2-[1-(2-Methyl-3-phenyl-allyl)-1H-[1,2,3]triazol-4-yl]-ethyl}-1H-imidazol-2-ylamine hydrochloride (0.054 g, 43%) of a pale yellow oil. $_1$H NMR (300 MHz, CD$_3$OD) δ 8.39 (s, 1H), δ 7.12-7.07 (m, 5H), δ 6.54 (s, 1H), δ 6.36 (s, 1H), δ 5.09 (s, 2H), δ 3.01 (t, 2H), δ 2.76 (t, 2H), δ 1.60 (s, 3H) ppm; $_{13}$C; 147.7, 143.1, 136.3, 132.7, 129.9, 128.9, 128.6, 128.5, 128.2, 127.4, 127.1, 124.9, 109.9, 61.2, 23.0, 22.3, 14.7 ppm; HRMS (ESI) calcd for C$_{16}$H$_{20}$N$_6$ (M$_+$) 308.1749. found 308.1742.

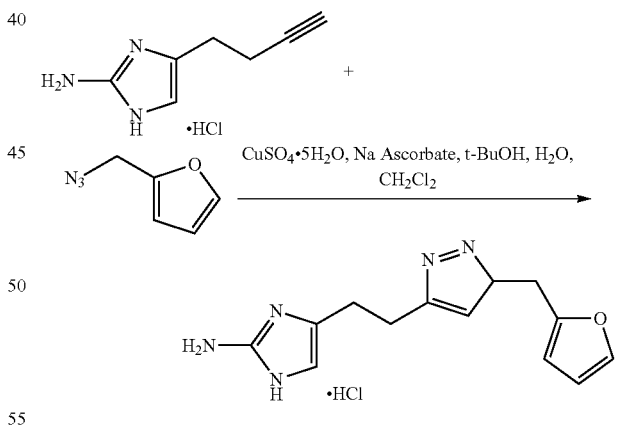

4-But-3-ynyl-1H-imidazol-2-ylamine hydrochloride (0.068 g, 0.399 mmol) was reacted with 2-azidomethyl furan (0.059 g, 0.478 mmol) following the general procedure for click reactions outlined above to produce 4-[2-(1-Furan-2-ylmethyl-1H-[1,2,3]triazol-4-yl)-ethyl]-1H-imidazol-2-ylamine hydrochloride (0.085 g, 72%) of a pale yellow solid. $_1$H NMR (300 MHz, CD$_3$OD) δ 8.06 (s, 1H), δ 7.53 (s, 1H), δ 6.59 (t, 1H), δ 6.49 (s, 1H), δ 6.44 (dd, 1H), δ 3.05 (t, 2H), δ 2.89 (t, 2H) ppm; $_{13}$C (75 MHz, CD$_3$OD) δ 156.4, 154.9, 147.5, 144.1, 126.0, 125.1, 123.8, 110.7, 109.3, 69.8, 23.8, 17.4 ppm; HRMS (ESI) calcd for C$_{12}$H$_{14}$N$_6$O (M$_+$) 259.1301. found 259.1305.

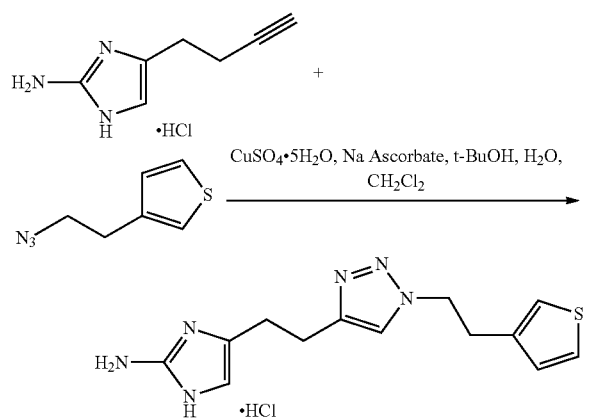

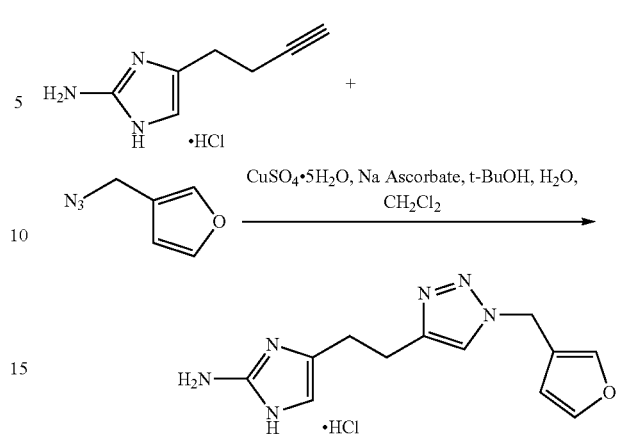

4-But-3-ynyl-1H-imidazol-2-ylamine hydrochloride (0.078 g, 0.45 mmol) was reacted with 3-(2-Azido-ethyl)-thiophene (0.083 g, 0.543 mmol) following the general procedure for click reactions outlined above to produce 4-{2-[1-(2-Thiophen-3-yl-ethyl)-1H-[1,2,3]triazol-4-yl]-ethyl}-1H-imidazol-2-ylamine hydrochloride (0.069 g, 47%) of a pale yellow oil. $_1$H NMR (300 MHz, CD$_3$OD) δ 7.33 (s, 1H), δ 7.19 (dd, 1H), δ 6.85 (d, 1H), δ 6.72 (d, 1H), δ 6.06 (s, 1H), δ 4.45 (t, 2H), δ 3.08 (t, 2H), δ 2.79 (t, 2H), δ 2.59 (t, 2H), ppm; $_{13}$C (75 MHz, CD$_3$OD) δ 149.3, 147.0, 137.7, 132.1, 127.7, 125.8, 122.4, 121.9, 110.6, 50.8, 30.7, 26.6, 24.8 ppm; HRMS (ESI) calcd for $C_{13}H_{17}N_6S$ (M$_+$) 289.1229. found 289.1231.

4-But-3-ynyl-1H-imidazol-2-ylamine hydrochloride (0.066 g, 0.384 mmol) was reacted with 3-azidomethyl-furan (0.057 g, 0.461 mmol) following the general procedure for click reactions outlined above to produce 4-[2-(1-Furan-3-ylmethyl-1H-[1,2,3]triazol-4-yl)-ethyl]-1H-imidazol-2-ylamine hydrochloride (0.061 g, 54%) as a pale yellow solid. $_1$H NMR (300 MHz, CD$_3$OD) δ 7.70 (s, 1H), δ 7.61 (s, 1H), δ 7.46 (s, 1H), δ 6.42 (s, 1H), δ 6.38 (s, 1H), δ 5.41 (s, 2H), δ 2.95 (t, 2H), δ 2.83 (t, 2H) ppm; $_{13}$C (75 MHz, CD$_3$OD) δ 146.3, 144.2, 141.6, 141.5, 126.5, 122.3, 120.2, 109.9, 109.1, 44.8, 24.2, 23.9 ppm; HRMS (ESI) calcd for $C_{12}H_{14}N_6O$ (M$_+$) 259.1301. found 259.1306.

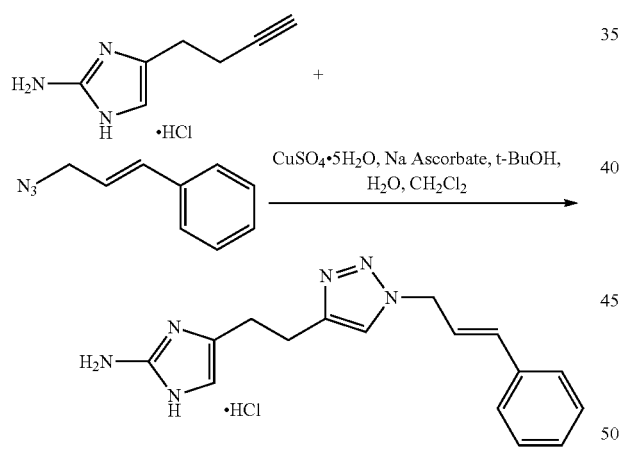

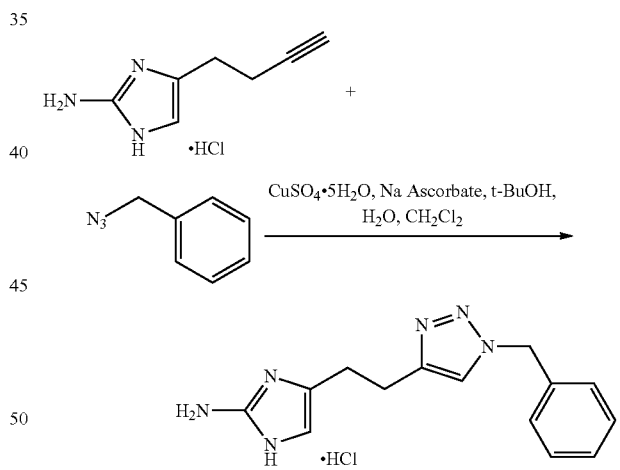

4-But-3-ynyl-1H-imidazol-2-ylamine hydrochloride (0.066 g, 0.383 mmol) was reacted with (3-azido-propenyl)-benzene, which was synthesized using previously reported methods (Rad et al., Tetrahedron Letters 2007, 48, 3445-3449), (0.079 g, 0.460 mmol) following the general procedure for click reactions outlined above to produce 4-{2-[1-(3-Phenyl-allyl)-1H-[1,2,3]triazol-4-yl]-ethyl}-1H-imidazol-2-ylamine hydrochloride (0.049 g, 39%) of a pale yellow oil. $_1$H NMR (300 MHz, CD$_3$OD) δ 8.19 (s, 1H), δ 7.44 (d, 2H), δ 7.29 (m, 3H), δ 6.73 (d, 1H), 6.53 (s, 1H), δ 6.42 (m, 2H), δ 5.24 (d, 2H), δ 3.07 (t, 2H), δ 2.88 (t, 2H) ppm; $_{13}$C 148.6, 145.3, 139.4, 139.2, 129.8, 129.7, 129.6, 128.5, 128.4, 127.6, 54.6, 47.3, 45.9, 26.3, 22.6 ppm; HRMS (ESI) calcd for $C_{16}H_{19}N_6$ (M$_+$) 295.1665. found 295.1670.

4-But-3-ynyl-1H-imidazol-2-ylamine hydrochloride (0.073 g, 0.423 mmol) was reacted with benzyl azide (0.068 g, 0.509 mmol) following the general procedure for click reactions outlined above to produce 4-[2-(1-Benzyl-1H-[1,2,3]triazol-4-yl)-ethyl]-1H-imidazol-2-ylamine hydrochloride (0.059 g, 46%) as a pale yellow oil. $_1$H NMR (300 MHz, CD$_3$OD) δ 7.83 (d, 1H), δ 7.37-7.24 (m, 5H), δ 6.44 (d, 1H), δ 5.54 (d, 2H), δ 2.96 (m, 2H), δ 2.83 (m, 2H) ppm; $_{13}$C (75 MHz, CD$_3$OD) δ 163.7, 147.3, 146.4, 135.7, 128.8, 128.4, 127.9, 127.8, 126.5, 122.6, 109.1, 53.7, 24.1, 23.9 ppm; HRMS (ESI) calcd for $C_{14}H_{16}N_6$ (M$_+$) 269.1515. found 269.1513.

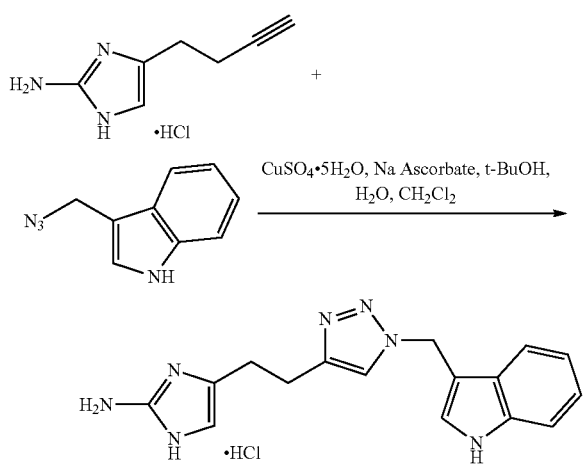

4-But-3-ynyl-1H-imidazol-2-ylamine hydrochloride (0.073 g, 0.429 mmol) was reacted with 3-azidomethyl-indole (0.089 g, 0.515 mmol) following the general procedure for click reactions outlined above to produce 4-{2-[1-(1H-Indol-3-ylmethyl)-1H-[1,2,3]triazol-4-yl]-ethyl]-1Himidazol-2-ylamine hydrochloride (0.086 g, 58%) as a yellow oil. $_1$H NMR (300 MHz, CD$_3$OD) δ 8.11 (s, 1H), δ 7.84 (m, 2H), δ 7.41 (m, 2H), δ 7.06 (d, 1H), δ 5.66 (s, 2H), δ 3.04 (t, 2H), δ 2.85 (t, 2H) ppm; $_{13}$C (75 MHz, CD$_3$OD) δ 147.5, 144.9, 144.8, 134.7, 131.9, 127.2, 127.1, 127.1, 125.8, 125.3, 124.4, 109.5, 49.9, 23.6, 23.2 ppm; HRMS (ESI) calcd for C$_{17}$H$_{19}$N$_7$ (M$_+$) 321.1701. found 321.1704.

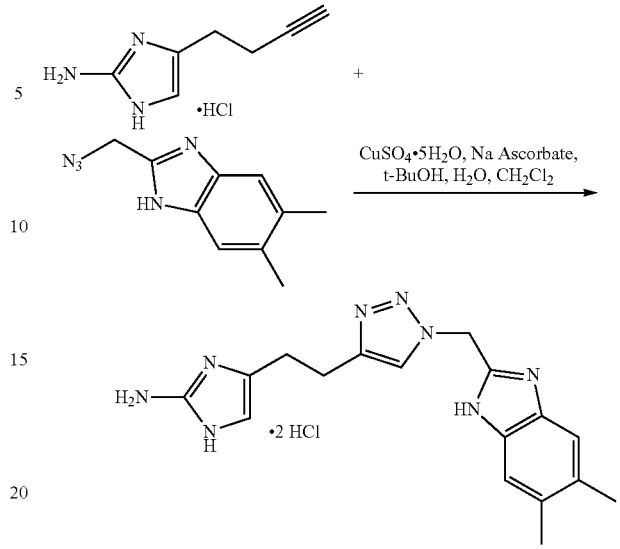

4-But-3-ynyl-1H-imidazol-2-ylamine hydrochloride (0.0734 g, 0.432 mmol) was reacted with 2-azidomethyl-5,6-dimethyl-1H-benzimidazole (0.104 g, 0.518 mmol) following the general procedure for click reactions outlined above to produce 4-{2-[1-(5,6-Dimethyl-1Hbenzoimidazol-2-ylmethyl)-1H-[1,2,3]triazol-4-yl]-ethyl}-1H-imidazol-2-ylamine dihydrochloride (0.104 g, 59%) of a pale yellow solid. $_1$H NMR (300 MHz, CD$_3$OD) δ 7.70 (s, 1H), δ 7.19 (s, 2H), δ 6.23 (s, 1H), δ 5.66 (s, 2H), δ 2.85 (t, 2H), δ 2.68 (t, 2H), □ 2.21 (s, 6H) ppm; $_{13}$C (75 MHz, CD$_3$OD) δ 148.2, 147.0, 146.9, 132.3, 128.9, 122.8, 120.0, 115.1, 109.7, 100.4, 25.1, 24.4, 19.2 ppm; HRMS (ESI) calcd for C$_{17}$H$_{20}$N$_8$ (M$_+$) 337.1883. found 337.1886.

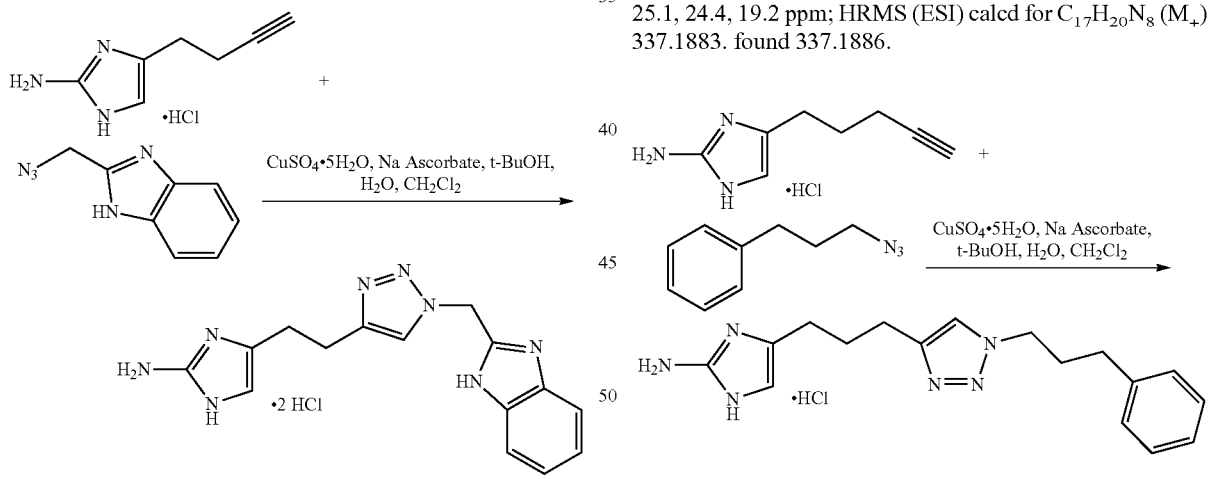

4-But-3-ynyl-1H-imidazol-2-ylamine hydrochloride (0.061 g, 0.361 mmol) was reacted with 2-azidomethyl-1-H-benzimidazole (0.075 g, 0.433 mmol) following the general procedure for click reactions outlined above to produce 4-{2-[1-(1H-Benzoimidazol-2-ylmethyl)-1H-[1,2,3]triazol-4-yl]-ethyl}-1H-imidazol-2-ylamine dihydrochloride (0.066 g, 48%) of a yellow solid. $_1$H NMR (300 MHz, CD$_3$OD) δ 8.05 (s, 1H), δ 7.68 (m. 2H), δ 7.48 (m, 2H), δ 6.38 (s, 1H), δ 6.15 (s, 2H'), δ 2.90 (t, 2H), δ 2.76 (t, 2H) ppm; $_{13}$C (75 MHz, CD$_3$OD) δ 147.4, 146.9, 146.8, 131.3, 127.0, 126.4, 124.1, 114.1, 109.2, 44.7, 24.0, 23.9 ppm; HRMS (ESI) calcd for C$_{15}$H$_{17}$N$_8$ (M$_+$) 309.1570. found 309.1572.

4-Pent-4-ynyl-1H-imidazol-2-ylamine hydrochloride (0.050 g, 0.269 mmol) was reacted with (3-azido-propyl) benzene (0.044 g, 0.273 mmol) following the general procedure for click reactions outlined above to produce 4-{3-[1-(3-Phenyl-propyl)-1H-[1,2,3]triazol-4-yl]-propyl}-1H-imidazol-2-ylamine hydrochloride (0.0318 g, 34%) as a pale yellow solid. $_1$H NMR (300 MHz, DMSO) δ 7.91 (s, 1H), δ 7.29-7.17 (m, 5H), δ 6.62 (s, 2H), δ 6.57 (s, 1H), δ 4.29 (t, 2H), δ 2.59 (t, 2H), δ 2.53 (t, 2H), δ 2.43 (t, 2H) δ 2.09 (m, 2H), δ 1.83 (m, 2H) ppm; $_{13}$C NMR (75 MHz, DMSO) δ 163.6, 156.2, 155.1, 147.4, 146.9, 141.4, 129.1, 127.1, 126.7, 122.6, 109.4, 49.4, 32.6, 32.0, 28.1, 24.9, 24.2 ppm; HRMS (ESI) calcd for C$_{17}$H$_{22}$N$_6$ (M$_+$) 310.1978. found 310.1977.

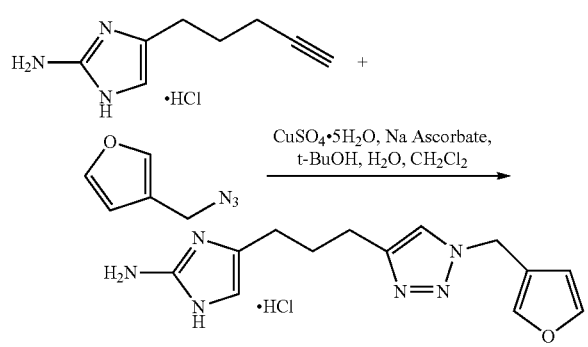

4-Pent-4-ynyl-1H-imidazol-2-ylamine hydrochloride (0.063 g, 0.340 mmol) was reacted with 3-azidomethyl-furan (0.050 g, 0.406 mmol) following the general procedure for click reactions outlined above to produce 4-[3-(1-Furan-3-ylmethyl-1H-[1,2,3]triazol-4-yl)-propyl]-1Himidazol-2-ylamine hydrochloride (0.061 g, 58%) as a pale yellow solid. $_1$H NMR (300 MHz, CD$_3$OD) δ 7.70 (s, 1H), δ 7.56 (s, 1H), δ 7.41 (s, 1H), δ 6.44 (s, 1H), δ 6.35 (s, 1H), δ 5.35 (s, 2H), δ 2.65 (t, 2H), δ 2.45 (t, 2H), δ 1.86 (m, 2H) ppm; $_{13}$C NMR (75 MHz, CD$_3$OD) δ 147.3, 147.3, 144.2, 141.6, 127.2, 122.1, 120.2, 109.9, 108.8, 44.7, 27.8, 24.2, 23.6 ppms; HRMS (ESI) calcd for C$_{13}$H$_{16}$N$_6$O (M$_+$) 272.1458. found 272.1462.

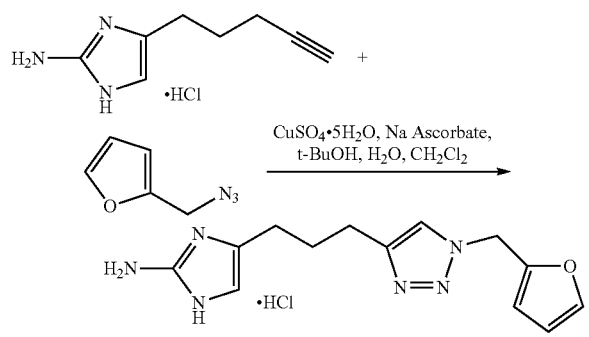

4-Pent-4-ynyl-1H-imidazol-2-ylamine hydrochloride (0.093 g, 0.500 mmol) was reacted with 2-azidomethyl-furan (0.074 g, 0.601 mmol) following the general procedure for click reactions outlined above to produce 4-[3-(1-Furan-2-ylmethyl-1H-[1,2,3]triazol-4-yl)-propyl]-1Himidazol-2-ylamine hydrochloride (0.075, 50%) as a pale yellow solid. $_1$H NMR (300 MHz, DMSO) δ 7.85 (s, 1H), δ 7.65 (s, 1H), δ 6.70 (s, 2H), δ 6.64 (s, 1H), δ 6.52 (t, 1H), δ 6.46 (s, 1H), δ 5.58 (s, 2H), δ 2.61 (t, 2H), δ 2.41 (t, 2H), δ 1.82 (m, 2H) ppm; $_{13}$C NMR (75 MHz, DMSO) δ 163.6, 149.4, 147.9, 147.4, 144.3, 128.5, 122.6, 111.5, 110.3, 109.9, 46.3, 28.4, 24.9 ppm; HRMS (ESI) calcd for C$_{13}$H$_{16}$N$_6$O (M$_+$) 272.1458. found 272.1460.

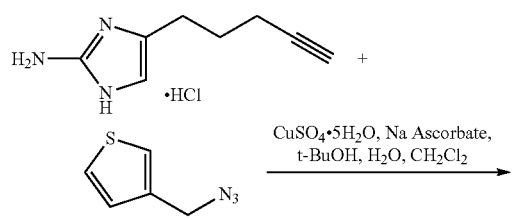

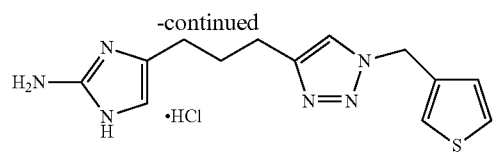

4-Pent-4-ynyl-1H-imidazol-2-ylamine hydrochloride (0.090 g, 0.486 mmol) was reacted with 3-Azidomethyl-thiophene (0.081 g, 0.582 mmol) following the general procedure for click reactions outlined above to produce 4-[3-(1-Thiophen-3-ylmethyl-1H-[1,2,3]triazol-4-yl)-propyl]-1H-imidazol-2-ylamine hydrochloride (0.0727 g, 46%) as a pale yellow solid. $_1$H NMR (300 MHz, CD$_3$OD) δ 7.61 (s, 1H), δ 7.24 (s, 1H), δ 7.23 (d, 1H), δ 6.87 (d, δ 6.29 (s, 1H), δ 2.54 (t, 2H), 2.33 (t, 2H), δ 1.75 (m, 2H) ppm; $_{13}$C NMR (75 MHz, CD$_3$OD) δ 147.6, 147.4, 147.3, 136.1, 127.9, 127.0, 126.9, 124.2, 122.2, 109.1, 53.1, 27.9, 24.3; HRMS (ESI) calcd for C$_{13}$H$_{16}$N$_6$S (M$_+$) 289.1229. found 289.1234.

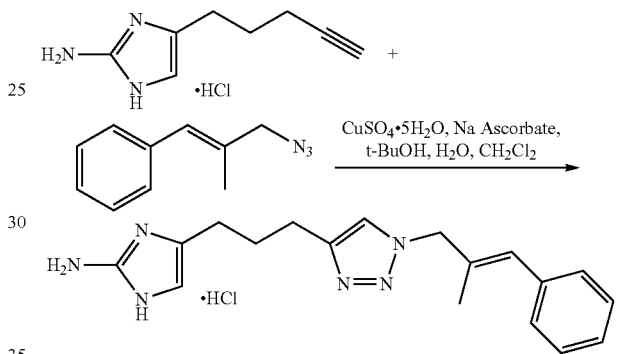

4-Pent-4-ynyl-1H-imidazol-2-ylamine hydrochloride (0.096 g, 0.517 mmol) was reacted with (3-Azido-2-methyl-propenyl)-benzene (0.110 g, 0.635 mmol) following the general procedure for click reactions outlined above to produce 5-{3-[1-(2-Methyl-3-phenyl-allyl)-1H-[1,2,3]triazol-4-yl]-propyl}-1H-imidazol-2-ylamine hydrochloride (0.076, 41%) as a pale yellow solid. $_1$H NMR (300 MHz, CD$_3$OD) δ 7.65 (s, 1H), δ 7.14-7.04 (m, 5H), δ 6.35 (s, 1H), δ 6.28 (s, 1H), δ 4.94 (s, 2H), δ 2.57 (t, 2H), δ 2.34 (t, 2H), δ 1.75 (m, 2H), δ 1.57 (s, 3H) ppm; $_{13}$C NMR (75 MHz, CD$_3$OD) δ 147.5, 136.9, 132.5, 129.7, 128.8, 128.6, 128.4, 128.3, 128.2, 126.9, 122.5, 109.2, 58.1, 61.9, 28.0, 24.3, 24.3, 24.1, 14.6 ppm; HRMS (ESI) calcd for C$_{18}$H$_{22}$N$_6$ (M$_+$) 323.1978. found 323.1984.

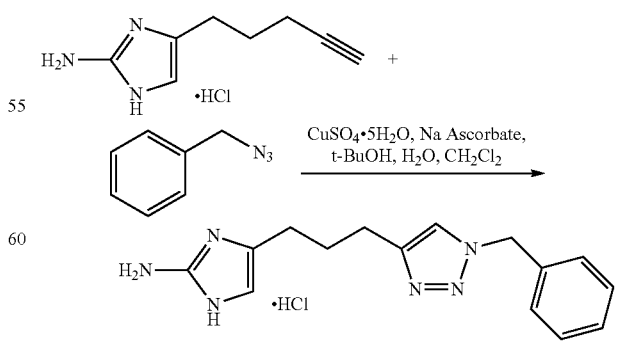

4-Pent-4-ynyl-1H-imidazol-2-ylamine hydrochloride (0.081 g, 0.437 mmol) was reacted with benzyl azide (0.071 g, 0.533 mmol) following the general procedure for click reactions outlined above to produce 4-[3-(1-Benzyl-1H-[1,2,3]triazol-4-yl)-propyl]-1H-imidazol-2-ylamine hydrochloride (0.073 g, 53%) as a pale yellow solid. $_1$H NMR (300 MHz, DMSO) δ 7.93 (s, 1H), δ 7.37-7.27 (m, 5H), δ 6.63 (s, 2H), δ 6.44 (s, 1H), δ 2.61 (t, 2H), δ 2.40 (t, 2H), δ 1.82 (m, 2H) ppm; $_{13}$C NMR (75 MHz, DMSO) δ 163.5, 148.1, 147.4, 135.9, 129.4, 128.7, 128.5, 128.4, 122.8, 122.8, 115.9, 109.9, 53.3, 28.5, 25.0; HRMS (ESI) calcd for $C_{15}H_{18}N_6$ ($M_+$) 282.1665. found 282.1674.

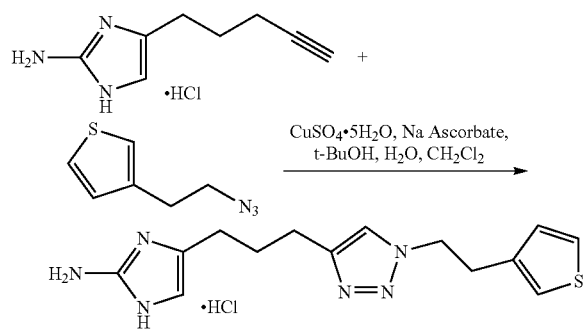

4-Pent-4-ynyl-1H-imidazol-2-ylamine hydrochloride (0.090 g, 0.485 mmol) was reacted with 3-(2-Azido-ethyl)-thiophene (0.089 g, 0.581 mmol) following the general procedure for click reactions outlined above to produce 4-{3-[1-(2-Thiophen-3-yl-ethyl)-1H-[1,2,3]triazol-4-yl]-propyl}-1H-imidazol-2-ylamine hydrochloride (0.067 g, 41%) as a pale yellow solid. $_1$H NMR (300 MHz, CD$_3$OD) δ 7.42 (s, 1H), δ 7.12 (d, 1H), δ 6.83 (s, 1H), δ 6.70 (d, 1H), δ 6.29 (s, 1H), δ 4.41 (t, 2H), δ 3.04 (t, 2H), δ 2.50 (t, 2H), δ 2.29 (t, 2H), δ 1.72 (m, 2H) ppm; $_{13}$C NMR (75 MHz, CD$_3$OD) δ 146.8, 146.8, 137.7, 127.8, 127.6, 125.7, 122.6, 121.9, 109.0, 50.7, 30.7, 27.9, 23.7 ppm; HRMS (ESI) calcd for $C_{14}H_{18}N_6S$ ($M_+$) 302.1313. found 302.1317.

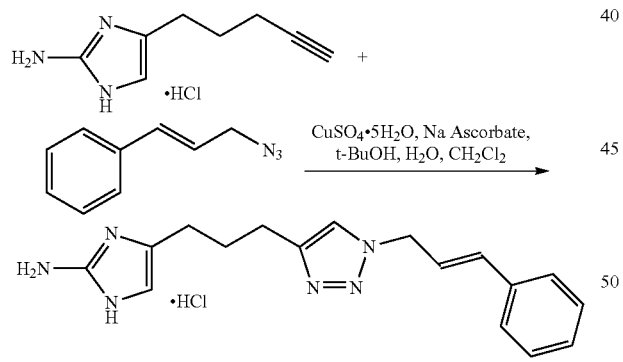

4-Pent-4-ynyl-1H-imidazol-2-ylamine hydrochloride (0.115 g, 0.620 mmol) was reacted with (3-azido-propenyl)-benzene (0.119 g, 0.748 mmol) following the general procedure for click reactions outlined above to produce 4-{3-[1-(3-Phenyl-allyl)-1H-[1,2,3]triazol-4-yl]-propyl}-1Himidazol-2-ylamine hydrochloride (0.082 g, 43%) as a pale yellow solid. $_1$H NMR (300 MHz, CDCl$_3$) δ 7.34-7.24 (m, 6H), δ 6.67 (d, 1H), δ 6.34 (q, 1H), δ 6.25 (s, 1H), δ 5.08 (d, 2H), δ 2.72 (t, 2H), δ 2.47 (t, 2H), δ 1.91 (m, 2H) ppm; $_{13}$C (75 MHz, CD$_3$OD) 149.1, 137.9, 133.5, 129.5, 128.9, 128.7, 128.3, 128.2, 127.2, 126.8, 54.8, 48.9, 31.3, 29.6, 27.5 ppm; HRMS (ESI) calcd for $C_{17}H_{21}N_6$ ($M_+$) 308.1822. found 308.1821.

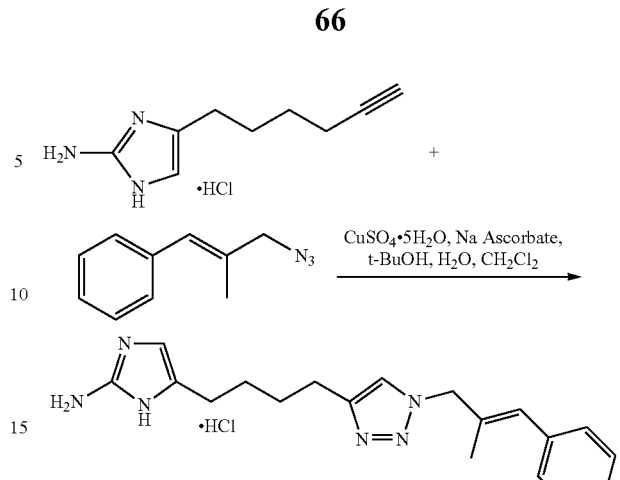

4-Hex-5-ynyl-1H-imidazol-2-ylamine hydrochloride (0.089 g, 0.4.47 mmol) was reacted with (3-Azido-2-methyl-propenyl)-benzene (0.085 g, 0.491 mmol) following the general procedure for click reactions outlined above to produce 4-{4-[1-(2-Methyl-3-phenyl-allyl)-1H-[1,2,3]triazol-4-yl]-butyl}-1H-imidazol-2-ylamine (0.132 g, 79%) as a pale yellow solid. $_1$H NMR (300 MHz, CD$_3$OD) δ 8.36 (s, 1H), 7.03 (m, 5H), 6.49 (s, 1H), 6.25 (s, 1H), 5.05 (s, 2H), δ 2.67 (t, 2H), δ 2.73 (t, 2H), δ 1.56 (s, 3H), δ 1.42 (m, 4H) ppm; $_{13}$C (75 MHz, CD$_3$OD) δ 147.3, 144.7, 136.4, 132.7, 129.9, 128.9, 128.6, 128.5, 128.3, 127.5, 127.2, 126.9, 108.7, 61.2, 27.4, 27.3, 23.8, 22.8, 14.8 ppm; HRMS (ESI) calcd for $C_{19}H_{24}N_6$ ($M_+$) 336.2135. found 336.2134.

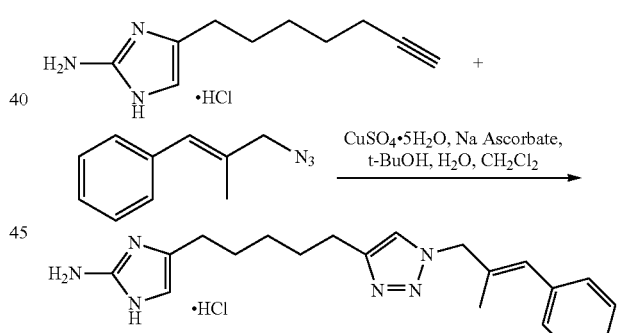

4-Hept-6-ynyl-1H-imidazol-2-ylamine hydrochloride (0.060 g, 0.281 mmol) was reacted with (3-Azido-2-methyl-propenyl)-benzene (0.058 g, 0.336 mmol) following the general procedure for click reactions outlined above to produce 4-{5-[1-(2-Methyl-3-phenyl-allyl)-1H-[1,2,3]triazol-4-yl]-pentyl}-1H-imidazol-2-ylamine hydrochloride (0.064 g, 65%) as a pale yellow solid. $_1$H NMR (300 MHz, CD$_3$OD) δ 8.23 (s, δ 6.93-6.83 (m, 5H), δ 6.38 (s, 1H), δ 6.08 (s, 1H), δ 4.93 (s, 2H), δ 2.51 (t, 2H), δ 2.09 (t, 2H), δ 1.43 (s, 3H), δ 1.41 (m, 2H), δ 1.25 (m, 2H), δ 1.05 (m, 2H) ppm; $_{13}$C (75 MHz, CD$_3$OD) δ 147.7, 144.8, 136.3, 132.8, 129.8, 128.9, 128.6, 128.5, 128.2, 127.6, 127.5, 127.0, 108.5, 61.3, 28.0, 27.6, 27.5, 24.0, 22.9, 14.7 ppm; HRMS (ESI) calcd for $C_{20}H_{27}N_6$ ($M_+$) 351.2291. found 351.2291.

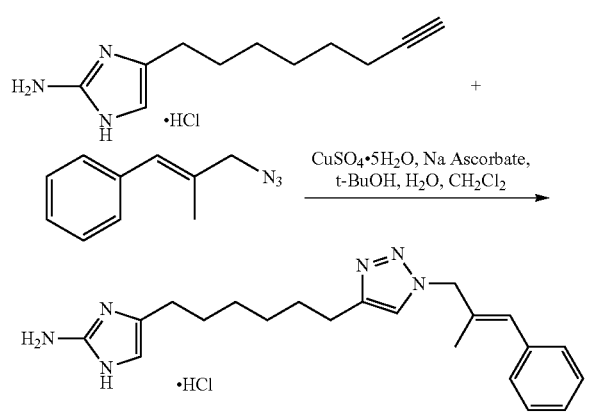

4-Oct-7-ynyl-1H-imidazol-2-ylamine hydrochloride (0.098 g, 0.568 mmol) was reacted with (3-Azido-2-methyl-propenyl)-benzene (0.118 g, 0.681 mmol) following the general procedure for click reactions outlined above to produce 4-{6-[1-(2-Methyl-3-phenyl-allyl)-1H-[1,2,3]triazol-4-yl]-hexyl}-1H-imidazol-2-ylamine hydrochloride (0.147 g, 85%) as a pale yellow solid. $_1$H NMR (300 MHz, CD$_3$OD) δ 8.42 (s, 1H), δ 7.25-7.15 (m, 5H), δ 6.65 (s, 1H), δ 6.36 (s, 1H), δ 5.23 (s, 2H), δ 2.78 (t, 2H), δ 2.38 (t, 2H), δ 1.74 (s, 3H), δ 1.64 (m, 2H), δ 1.51 (m, 2H), δ 1.33 (m, 4H) ppm; $_{13}$C (75 MHz, CD$_3$OD) δ 147.5, 136.3, 132.9, 132.8, 129.9, 128.9, 128.6, 128.5, 128.3, 127.7; HRMS (ESI) calcd for C$_{21}$H$_{29}$N$_6$(M$_+$) 365.2448. found 365.2448.

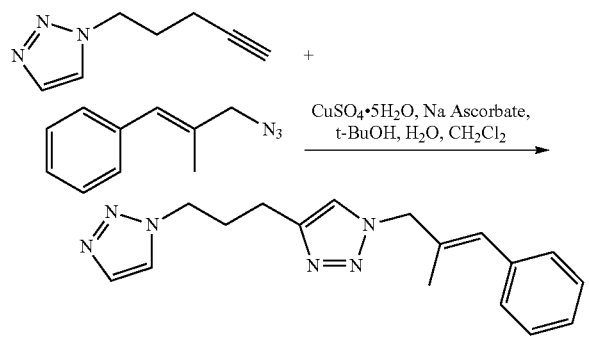

1-Pent-4-ynyl-1H-[1,2,3]triazole (0.100 g, 0.739 mmol) was reacted with (3-Azido-2-methylpropenyl)-benzene (0.154 g, 0.889 mmol) following the general procedure for click reactions outlined above to produce 1-(2-Methyl-3-phenyl-allyl)-4-(3-[1,2,3]triazol-1-yl-propyl)-1H-[1,2,3]triazole (0.227 g, Quantitative) as a white solid. $_1$H NMR (300 MHz, DMSO) δ 7.91 (s, 1H), δ 7.77 (s, 2H), δ 7.40-7.25 (m, 5H), δ 6.47 (s, 1H), δ 5.05 (s, 2H), δ 4.48 (t, 2H), δ 2.62 (t, 2H), δ 2.50 (t, 2H), δ 2.21 (m, 2H), δ 1.74 (s, 3H) ppm; $_{13}$C (75 MHz, DMSO) δ 146.4, 137.1, 134.8, 133.6, 132.8, 129.4, 129.3, 129.2, 128.9, 127.6, 123.0, 57.9, 54.0, 32.9, 29.6, 22.7, 16.2 ppm; HRMS (ESI) calcd for C$_{17}$H$_{21}$N$_6$ (M$_+$) 309.1822. found 309.1821.

Example 2

Activity Testing of 2-AIT Library Members

A Standard Crystal Violet reporter assay is employed to assess the effect of compounds from the 2-amino on the formation of biofilms. Among others, the following strains are tested:

Xanthomonas Xccl
Xanthomonas Xcv.135
Xanthomonas Xcv5
Xanthomonas Xccp
Xanthomonas Xcp60
Xanthomonas Xcp25
Ralstonia solanacearum K66

Xanthomonas is a Gram-negative rod-shaped bacterium that is a common plant pathogen. Xanthomonas bacteria grow almost exclusively in plants. Xanthomonas species testing includes X. vesicatoria (crop=tomato), X. euvesicatoria (crop=pepper), X. campestris (crop=crucifers, particularly cabbage), X. zinniae (crop=zinnia), and X. fragariae (crop=strawberry). Ralstonia solanacearum is a Gram-negative bacterium that is found in soil.

Bacteria are allowed to form biofilms in a multi-well plate in the absence or presence of one or more compounds. Planktonic (or free growing) bacteria are then removed, wells washed vigorously, and crystal violet added. Crystal violet stains the remaining bacteria which, following ethanol solubilization, is quantitated by spectrophotometry (A$_{540}$). Time-dependent and concentration-dependent analysis of each compound are performed.

Example 3

Activity Testing of 2-AIT Library Members on Xanthomonas

Biofilm formation on PVC microtiter wells was accomplished using Xanthomonas strains Xcv 135 (known to infect peppers and tomatoes) and Xcv 5 (known to infect tomatoes but not peppers) as models. The Starting Optical Density (OD at 600 nm) for biofilm attachment assay was 0.55, the temperature for this assay was 28° C., the duration of incubation was 6 hours under, and the assay was static.

Biofilm inhibition results are as follows for screens with Xcv 135. The Xcv 5 strain is tested in the same manner.

| Compound Screened | % Inhibition at 20 μM (vs. Xcv 135) |
|---|---|
| Formula (II)(a)(5)(D) | 86% |
| Formula (II)(a)(6)(D) | 85% |
| Formula (II)(i)(a)(2)(J) | 0% |

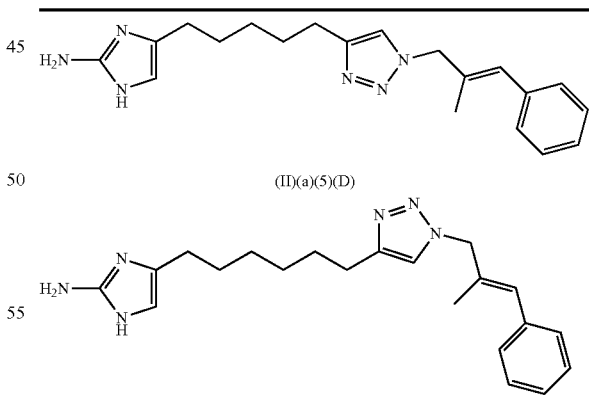

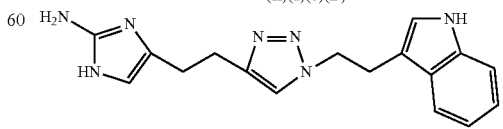

Example 4

Activity Testing in Pepper Plants Inoculated with *Xanthomonas euvesicatoria* (Bacterial Spot)

To test the effects of the triazole derivatives for plant biofilm inhibition activity, the compound of Formula (II)(a)(5)(D) was used as an exemplary compound (the "biofilm inhibitor/disperser" or "BFI" in the text hereinafter of Example 4).

(II)(a)(5)(D)

The compound was evaluated under field conditions to determine whether it controls or enhances control of bacterial spot (caused by the bacterium *Xanthomonas euvesicatoria*) of pepper when applied alone or in tank-mixtures with a copper (Kocide 3000), an antibiotic (GWN-9350, gentamicin), or a putative plant defense activator (Prophyt). Tests were performed April-July 2008 at the North Carolina Agricultural Research Service Sandhills Research Station, Montgomery County.

EXPERIMENTAL DESIGN and TREATMENT APPLICATIONS: Each treatment consisted of two 7-plant rows running east-west replicated in a four-block completely randomized design. Each 7-plant row was 10.5 ft×2 ft. This area was used to calculate the quantity of spray material extrapolated for a per acre basis. Plants of bell pepper cultivar 'X3R-Camelot' were transplanted to the field on Apr. 24, 2008. On May 6, two plants in the south row of each plot of each treatment were inoculated with a suspension of copper-resistant strains of the bacterial pathogen. These plants were destined to serve as the inoculum source for each plot. Each of the spray test materials was mixed in 1.5 liters of water and applied using a backpack sprayer by making a single pass on each side of the plant row. Treatments were applied weekly starting immediately after the plants had been inoculated May 6 followed by 7 additional weekly sprays for a total of 8 applications through June 24.

DATA: Ratings of foliar disease were started May 22, when symptoms were observed on the inoculated plants and continued weekly through June 25. Disease was most severe on the inoculated plants and then spread to the non-inoculated plants. Data from these two groups (inoculated plants and the non-inoculated) were evaluated separately. The results are expressed as disease progress over time using the calculated Area Under the Disease Progress Curve (AUDPC). Two fruit harvests were done; July 1 and 8. Because there had been plant loss in some plots, the number of plants per plot was counted and yields (number of fruit and weight) were calculated and are reported on a per plant basis per treatment. Results are presented in Table 2 below.

TABLE 2

| Treatment & rate/acre (based on 100 gal water/acre) | Mean AUDPC for inoculated plants* | Mean AUDPC for entire plot* | Mean number pepper fruit/plant | Mean fruit yield (lb)/plant |
|---|---|---|---|---|
| 1 - NT Check | 162 a** | 45 a** | 6.0 ab** | 1.85 ab** |
| 2 - Kocide 3000 (30% MCE) 1.25 lb | 123 b | 37 ab | 6.5 ab | 1.86 ab |
| 3 - BFI 0.467 oz (35 mg/L) | 113 b | 42 a | 4.8 b | 1.46 b |
| 4 - GWN-9350 (10%) 3.5 lb + GWN-65 1.0 pt | 74 c | 15 c | 8.6 a | 2.52 a |
| 5 - ProPhyt 5.0 pt | 114 b | 37 ab | 6.5 ab | 2.06 ab |
| 6 - ProPhyt 5.0 pt + BFI 0.467 oz (35 mg/L) | 64 c | 25 bc | 6.3 ab | 1.74 b |
| 7 - GWN-9350 + GWN-65 1.0 pt + BFI 0.467 oz (35 mg/L) | 41 c | 12 c | 8.3 a | 2.51 a |
| 8 - Kocide 3000 1.25 lb + BFI 0.467 oz (35 mg/L) | 62 c | 16 c | 8.6 a | 2.54 a |
| L.S.D. $\alpha = 0.05$ | 34 | 16 | 2.6 | 0.76 |
| and probability of > treatment F value | 0.0001 | 0.0006 | 0.0466 | 0.0483 |

*0-9 rating scale with 0 = no disease, 1 = at least 1 diseased leaf, 2 = 1-5% foliage diseased or defoliated, 3 = 6-10%, 4 = 11-15%, 5 = 16-25%, 6 = 26-50%, 7 = 51-75%, 8 = 76-99%, and 9 = 100% leaves diseased or plant completely defoliated.

**Means within a column followed by the same letter do not differ significantly, L.S.D. $\alpha = 0.05$.

Example 5

Activity Testing in Fungus

The compound of Formula (II)(a)(5)(D) was used as an exemplary compound to evaluate the ability of 2-AIT compounds to inhibit the formation of *Candida albicans* biofilms.

(II)(a)(5)(D)

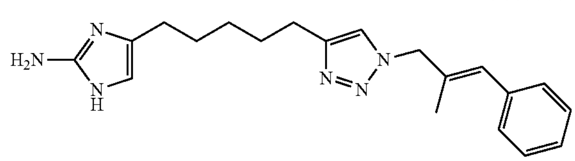

It was screened at 100 μM for its ability to inhibit to the formation of *C. albicans* biofilms using a crystal violet reporter assay. Briefly, biofilms were allowed to form for 24 hours in a 96-well microtiter plate in the absence or presence of 100 μM of the compound. The wells were subsequently washed thoroughly with water to remove free-floating and loosely adherent fungus, and then treated with crystal violet. Crystal violet stains the remaining surface attached fungus (i.e. the biofilm), which following solublization, can be quantified by spectrophotometry ($A_{540}$).

From this initial screen, we determined that the exemplary compound was able to inhibit *C. albicans* formation by 12% at 100 μM. Follow up growth curves at 100 μM demonstrated that this anti-biofilm activity was non-fungicidal (data not shown).

With this initial success of inhibiting fungal biofilms with a 2-AI derivative, we asked the question whether analogue synthesis could deliver alternative 2-AIT derivatives with enhanced anti-biofilm activity in the context of fungal biofilms. Previous work in our lab has demonstrated that 2-AI-based inhibitors of biofilms can be sub-divided into three separate sections: 1) the 2-AI head, 2) the linker region, and 3) the tail region. Structure activity relationship (SAR) data indicates that selectivity and activity can be tuned/enhanced by modification of the tail region.

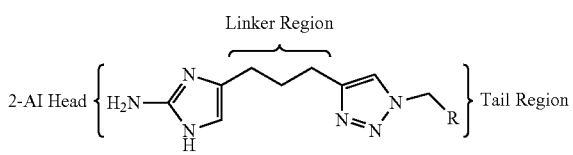

Based upon this data, we synthesized a new pilot library of 2-AI derivatives for anti-biofilm testing in which diversity could be rapidly assembled via substituents off the triazole ring through commercially available carboxylic acids.

The synthetic approach to this library is outlined in Scheme 2. In our previous synthesis of 2-AIT conjugates, we employed the alkyne-derived 2-AI as a precursor to the $Cu^I$-mediated [3+2] alkyne/azide cycloaddition (click reaction). Although this reaction worked well, purification of the resulting product was cumbersome due to the use of copious amounts of ammonia saturated methanol for column chromatography. Therefore, we decided to revise the route by employing a boc-protected 2-AI alkyne that would allow more traditional means of purification (i.e. methanol/dichloromethane columns). The boc-protected scaffold was synthesized from 7-octynoic acid by treatment with oxayl chloride followed by diazomethane and quenching the resulting α-diazo ketone with HBr to generate the intermediate α-bromo ketone. Cyclization with boc-guanidine then delivered the target 2-AI alkyne 5.

Scheme 2. Synthesis of triazole substituted 2-AI derivatives.

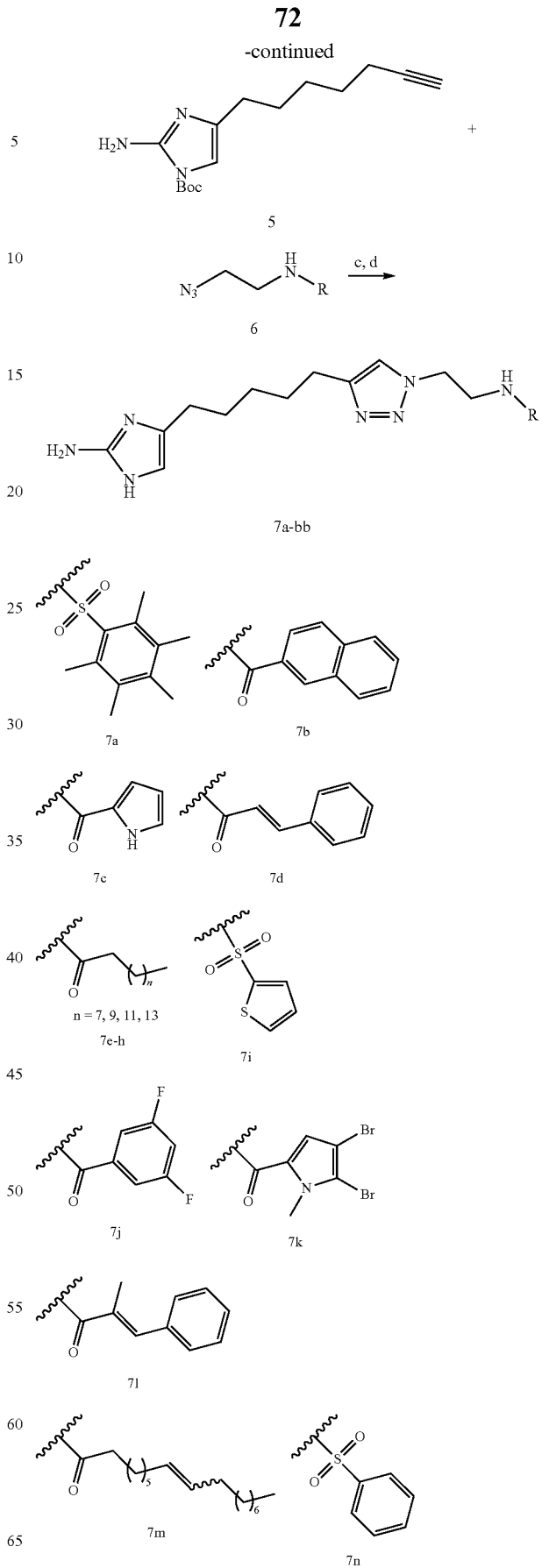

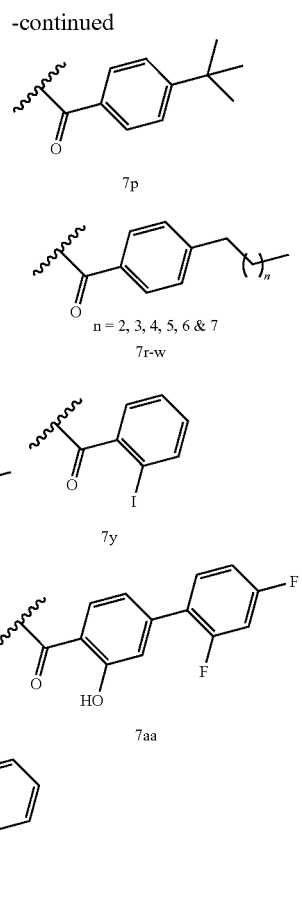

7o, 7p, 7q, 7r-w (n = 2, 3, 4, 5, 6 & 7), 7x, 7y, 7z, 7aa, 7bb a) i. (COCl$_2$), CH$_2$Cl$_2$, DMF (cat.), ii. CH$_2$N$_2$, Et$_2$O — CH$_2$Cl$_2$ iii. HBr 82% b) Boc-guanidine, DMF, rt (59%) c) Azide, CuSO$_4$, Na Ascorbate, EtOH, CH$_2$Cl$_2$, H$_2$O d) Trifluoroacetic acid, CH$_2$Cl$_2$ (58-94% over two steps).

Once 5 had been synthesized, we assembled a diverse array of azido amides to employ in the click reaction to create our pilot library of 2-AIT conjugates. Briefly, 2-bromo-ethylamine was treated with sodium azide to deliver 2-azidoethylamine, which following acylation (via the respective acid chloride) generated the azido amides for elaboration into the 2-AIT pilot library. Each azido amide was then subjected to the click reaction with the 2-AI 5. Boc-deprotection (TFA/CH$_2$Cl$_2$) followed by counterion exchange (trifluoroacetate for chloride) delivered the target 2-AIT library for anti-biofilm screening.

Each member of the pilot library was assayed at 100 µM for its ability to inhibit the formation of C. albicans biofilms using the crystal violet reporter assay. From this assay, 2-AIT derivatives 7f and 7m were determined to be the most potent. Subsequent dose response studies revealed that 7f had an IC$_{50}$ of 2.9 µM while 7m had an IC$_{50}$ of 3.3 µM (Table 3). Growth curve and colony count analysis of 7f and 7m at respective IC$_{50}$ values demonstrated their antibiofilm activity to be non-fungicidal (data not shown).

Next, we addressed whether 7f and 7m could disperse pre-formed C. albicans biofilms. C. albicans was allowed to establish biofilms in 96-well microtiter plate for 24 hours. Plates were then washed to remove any free floating or loosely adherent fungus. The appropriate 2-AIT (7f and 7m) was then added to each well at 75 µM and the plate was allowed to incubate at 37° C. for 24 hours. Wells were then washed with water and stained with CV to quantify any remaining biofilms. In comparison to biofilms treated with media only, compound 7f dispersed 56% while 7m dispersed 62% of the pre-formed biofilm. Once we had established that both compounds could disperse pre-formed biofilms, we quantified this effect by determining 7f and 7 m's EC$_{50}$ value against pre-formed C. albicans biofilms. Here, EC$_{50}$ is defined as the concentration at which the compound will disperse 50% of a pre-formed biofilm. Dose response studies revealed EC$_{50}$'s of 37.2 µM and 24.7 µM for 7f and 7m respectively (Table 1). From a medical perspective, molecules that simply inhibit the formation of a biofilm could be used in a prophylactic sense; however, given that a majority of patients already have an established biofilm infection when they seek medical intervention, molecules that are effective against a pre-formed biofilm are more clinically significant.

Once we had established that these next generation 2-AIT conjugates had the ability to inhibit and disperse C. albicans biofilms, we addressed whether members of this library would also inhibit and disperse biofilms from Cryptococcus neoformans, an opportunistic fungal strain known to infect immunosuppressed patients, especially those with HIV infections. Initial screening of our library showed that 7e and 7m had potent anti-biofilm activity against C. neoformans. Follow up dose response studies revealed IC$_{50}$'s of 1.3 µM and 8.0 µM (Table 3). Comparison of fungal growth in the presence or absence of either compound indicated that each compound was not fungicidal. Unfortunately, neither of these compounds was able to disperse pre-formed C. neoformans biofilms at the concentrations tested.

TABLE 3

Fungal biofilm inhibition and dispersion.

| Compound | IC$_{50}$ (µM) | EC$_{50}$ (µM) |
|---|---|---|
| | C. albicans | |
| 7f | 2.9 ± 0.7 | 37.2 ± 5.7 |
| 7m | 3.3 ± 1.6 | 24.7 ± 4.5 |
| | S. cerevisiae | |
| 7g | 2.7 ± 0.1 | 207.4 ± 7.3 |
| 7h | 50.4 ± 2.2 | 353.7 ± 7.3 |
| 7j | 130.6 ± 16.9 | >400 |
| | C. neoformans | |
| 7e | 1.3 ± 0.3 | — |
| 7m | 8.0 ± 3.4 | — |

Synthesis:

All reagents used for chemical synthesis were purchased from commercially available sources and used without further purification. Chromatography was performed using 60 Å mesh standard grade silica gel from Sorbtech. NMR solvents were obtained from Cambridge Isotope Labs and used as is. $^1$H NMR (300 MHz or 400 MHz) and $^{13}$C NMR (75 MHz or 100 MHz) spectra were recorded at 25° C. on Varian Mercury spectrometers. Chemical shifts (δ) are given in ppm relative to tetramethylsilane or the respective NMR solvent; coupling constants (J) are in hertz (Hz). Abbreviations used are s=singlet, bs=broad singlet, d=doublet, dd=doublet of doublets, t=triplet, dt=doublet of triplets, bt=broad triplet, qt=quartet, m=multiplet, bm=broad multiplet and br=broad.

N-(2-azidoethyl)tetradecanamide

To a 25 mL round-bottomed flask equipped with a magnetic stir bar was added 2-azidoethanamine (0.102 g, 1.18 mmol), DCM (5 mL) and then triethylamine (0.239 g, 2.37 mmol). To this reaction mixture, tetradecanoyl chloride (0.292 g, 1.18 mmol) was added dropwise and allowed to stir at room temperature for 24 hr. Then, the reaction mixture was concentrated de vacuo and then purified via silica gel column chromatography (100% dichloromethane to 1:40 methanol:dichloromethane) to give N-(2-azidoethyl)tetradecanamide (0.245 g, 79% yield). $^1$H NMR (300 MHz, CDCl$_3$) δ 5.86 (s, 1H), δ 3.42 (s, 41-1), δ 2.18 (t, J=7.8 Hz, 2H), δ 1.62 (m, 2H), δ 1.24 (m, 20H), δ 0.87 (t, J=3.9 Hz, 3H) ppm; $^{13}$C NMR (75 MHz, CDCl$_3$) δ 173.7, 51.2, 39.1, 36.9, 32.1, 29.9, 29.8, 29.7, 29.6, 29.5, 25.9, 22.9, 14.4 ppm; HRMS (ESI) calcd for C$_{16}$H$_{32}$N$_4$O (M+) 296.2576. found 296.2566.

N-(2-azidoethyl)octadec-9-enamide

As in the synthesis of N-(2-azidoethyl)tetradecanamide, octadec-9-enoyl chloride (0.374 g, 1.24 mmol) was reacted with 2-azidoethanamine (0.107 g, 1.24 mmol) and triethylamine (0.252 g, 2.49 mmol) in dichloromethane (5 mL) to give N-(2-azidoethyl)octadec-9-enamide (0.309 g, 71% yield). $^1$H NMR (300 MHz, CDCl$_3$) δ 6.30 (s, 1H), δ 5.29 (m, 2H), δ 3.39 (d, J=2.1 Hz, 2H), δ 3.38 (d, J=2.4 Hz, 2H), δ 2.19 (t, J=7.2 Hz, 2H), δ 1.97 (m, 4H), δ 1.59 (t, J=7.5 Hz, 2H), δ 1.26 (m, 20H), δ 0.84 (t, J=6.6 Hz, 3H) ppm; $^{13}$C NMR (75 MHz, CDCl$_3$) δ 173.9, 130.2, 129.9, 51.1, 39.1, 36.8, 32.1, 30.0, 29.9, 29.7, 29.5, 29.4, 29.3, 27.4, 27.3, 25.9, 22.9, 14.3 ppm; HRMS (ESI) calcd for C$_{20}$H$_{38}$N$_4$O (M+) 350.3046. found 350.3039.

N-(2-azidoethyl)thiophene-2-sulfonamide

As in the synthesis of N-(2-azidoethyl)tetradecanamide, thiophene-2-sulfonyl chloride (0.218 g, 1.19 mmol) was reacted with 2-azidoethanamine (0.103 g, 1.19 mmol) and triethylamine (0.241 g, 2.39 mmol) in dichloromethane (5 mL) to give N-(2-azidoethyl)thiophene-2-sulfonamide (0.221 g, 80% yield). $^1$H NMR (300 MHz, CDCl$_3$) δ 7.62 (d, J=1.2 Hz, 1H), δ 7.59 (d, J=1.2 Hz, 1H), 7.08 (t, J=3.9 Hz, 1H), 5.52 (s. 1H), 3.41 (t, J=5.4 Hz, 2H), 3.17 (q, J=5.4, 3.8 Hz, 2H) ppm; $^{13}$C NMR (75 MHz, CDCl$_3$) δ 140.6, 132.7, 132.6, 127.9, 50.9, 42.9 ppm; HRMS (ESI) calcd for C$_6$H$_8$N$_4$O$_2$S$_2$ (M+) 232.0089. found 232.0084.

N-(2-azidoethyl)-5-(dimethylamino)naphthalene-1-sulfonamide

As in the synthesis of N-(2-azidoethyl)tetradecanamide, 5-(dimethylamino)naphthalene-1-sulfonyl chloride (0.321 g, 1.19 mmol) was reacted with 2-azidoethanamine (0.103 g, 1.19 mmol) and triethylamine (0.241 g, 2.38 mmol) in dichloromethane (5 mL) to give N-(2-azidoethyl)-5-(dimethylamino)naphthalene-1-sulfonamide (0.328 g, 86% yield). $^1$H NMR (300 MHz, CDCl$_3$) δ 8.52 (d, J=8.4 Hz, 1H), δ 8.28 (d, J=8.4 Hz, 1H), δ 8.22 (d, J=0.9 Hz, 1H), δ 7.53 (t, J=8.1 Hz, 1H), δ 7.50 (t, J=7.5 Hz, 1H), δ 7.17 (d, J=7.8 Hz, 1H), δ 5.58 (t, J=1.8 Hz, 1H), δ 3.28 (t, J=5.7 Hz, 2H), δ 3.03 (q, J=6.3, 5.7 Hz, 2H), δ 2.85 (s, 6H) ppm; $^{13}$C NMR (75 MHz, CDCl$_3$) δ 152.3, 134.8, 130.9, 130.1, 129.7, 128.9, 123.4, 118.9, 115.6, 51.0, 45.6, 42.6 ppm; HRMS (ESI) calcd for C$_{14}$H$_{17}$N$_5$O$_2$S (M+) 319.1103. found 319.1104.

N-(2-azidoethyl)-2,3,4,5,6-pentamethylbenzenesulfonamide

As in the synthesis of N-(2-azidoethyl)tetradecanamide, 2,3,4,5,6-pentamethylbenzene-1-sulfonyl chloride (0.304 g, 1.23 mmol) was reacted with 2-azidoethanamine (0.106 g, 1.23 mmol) and triethylamine (0.249 g, 2.46 mmol) in dichloromethane (5 mL) to give N-(2-azidoethyl)-2,3,4,5,6-pentamethylbenzenesulfonamide (0.296 g, 81% yield). $^1$H NMR (300 MHz, CDCl$_3$) δ 5.12 (t, J=3.9 Hz, 1H) δ 3.35 (t, J=5.4 Hz, 2H), δ 3.05 (q, J=6.0, 5.1 Hz, 2H), 2.59 (s, 6H), δ 2.28 (s, 3H), 2.24 (s, 6H) ppm; $^{13}$C NMR (75 MHz, CDCl$_3$) δ 139.9, 136.1, 135.2, 134.2, 51.1, 42.3, 19.2, 17.9, 17.3 ppm; HRMS (ESI) calcd for C$_{13}$H$_{20}$N$_4$O$_2$S (M+) 296.1307. found 296.1304.

N-(2-azidoethyl)benzenesulfonamide

As in the synthesis of N-(2-azidoethyl)tetradecanamide, benzenesulfonyl chloride (0.201 g, 1.16 mmol) was reacted with 2-azidoethanamine (0.100 g, 1.16 mmol) and triethylamine (0.235 g, 2.32 mmol) in dichloromethane (5 mL) to give N-(2-azidoethyl)benzenesulfonamide (0.289 g, 84% yield). $^1$H NMR (300 MHz, CDCl$_3$) δ 7.90 (d, J=1.8 Hz, 2H), δ 7.55 (m, 3H), δ 5.47 (s, 1H), δ 3.39 (t, J=5.1 Hz, 2H), δ 3.12 (t, J=5.4 Hz, 2H) ppm; $^{13}$C NMR (75 MHz, CDCl$_3$) δ 139.8, 133.2, 129.5, 127.2, 50.9, 42.6 ppm; HRMS (ESI) calcd for C$_6$H$_8$N$_4$O$_2$S (M+) 226.0524. found 226.0523.

(E)-N-(2-azidoethyl)-4-phenylbut-3-enamide

As in the synthesis of N-(2-azidoethyl)tetradecanamide, (E)-4-phenylbut-3-enoyl chloride (0.198 g, 1.19 mmol) was reacted with 2-azidoethanamine (0.114 g, 1.19 mmol) and triethylamine (0.239 g, 2.37 mmol) in dichloromethane (5 mL) to give (E)-N-(2-azidoethyl)-4-phenylbut-3-enamide (0.168 g, 55% yield). $^1$H NMR (300 MHz, CDCl$_3$) δ 7.68 (d, J=15.6 Hz, 1H), δ 7.45 (d, J=3.3 Hz, 2H), δ 7.29 (m, 3H), δ 7.04 (t, J=4.1 Hz, 1H), δ 6.59 (d, J=15.9 Hz, 1H), δ 3.55 (q, J=6.0, 5.1 Hz, 2H), δ 3.47 (t, J=1.5 Hz, 2H) ppm; $^{13}$C NMR (75 MHz, CDCl$_3$) δ 166.9, 141.6, 134.9, 130.1, 129.1, 128.1, 120.8, 51.1, 39.4 ppm; HRMS (ESI) calcd for C$_{11}$H$_{12}$N$_4$O (M+) 216.1011. found 216.1005.

N-(2-azidoethyl)-2-(phenylthio)acetamide

As in the synthesis of N-(2-azidoethyl)tetradecanamide, 2-(phenylthio)acetyl chloride (0.222 g, 1.19 mmol) was reacted with 2-azidoethanamine (0.102 g, 1.19 mmol) and triethylamine (0.240 g, 2.37 mmol) in dichloromethane (5 mL) to give N-(2-azidoethyl)-2-(phenylthio)acetamide (0.179 g, 64% yield). $^1$H NMR (300 MHz, CDCl$_3$) δ 7.29 (m, 4H), δ 7.18 (m, 2H), δ 3.60 (s, 2H), 3.34 (m, 4H) ppm; $^{13}$C NMR (75 MHz, CDCl$_3$) δ 168.6, 134.8, 129.5, 128.6, 127.1, 50.8, 39.3, 37.7 ppm; HRMS (ESI) calcd for C$_{10}$H$_{12}$N$_4$OS (M+) 236.0732. found 236.0729.

N-(2-azidoethyl)palmitamide

As in the synthesis of N-(2-azidoethyl)tetradecanamide, (0.338 g, 1.23 mmol) was reacted with 2-azidoethanamine (0.106 g, 1.23 mmol) and triethylamine (0.249 g, 2.46 mmol) in dichloromethane (5 mL) to give N-(2-azidoethyl)palmitamide (0.336 g, 84% yield). $^1$H NMR (300 MHz, CDCl$_3$) δ 6.11 (s, 1H), δ 3.41 (s, 4H), δ 2.17 (t, J=7.5 Hz, 2H), δ 1.60 (m, 2H), δ 1.23 (m, 2H), δ 0.85 (t, 6.3 Hz, 3H) ppm; $^{13}$C NMR (75 MHz, CDCl$_3$) δ 173.9, 51.1, 39.1, 36.9, 32.1, 29.9, 29.8, 29.8, 29.7, 29.6, 29.5, 25.9, 22.9, 14.3 ppm; HRMS (ESI) calcd for C$_{18}$H$_{36}$N$_4$O (M+) 324.2889. found 324.2879.

N-(2-azidoethyl)decanamide

As in the synthesis of N-(2-azidoethyl)tetradecanamide, decanoyl chloride (0.251 g, 1.32 mmol) was reacted with 2-azidoethanamine (0.114 g, 1.32 mmol) and triethylamine (0.267 g, 2.64 mmol) in dichloromethane (5 mL) to give N-(2-azidoethyl)decanamide (0.262 g, 83% yield). $^1$H NMR (300 MHz, CDCl$_3$) δ 6.49 (s, 1H), δ 3.36 (s, 2H), δ 3.35 (s, 2H), δ 2.14 (t, J=7.2 Hz, 2H), δ 1.46 (m, 2H), δ 1.21 (m, 12H), δ 0.81 (t, J=6.0 Hz, 3H) ppm; $^{13}$C NMR (75 MHz, CDCl$_3$) δ 174.1, 50.9, 39.1, 36.8, 32.0, 29.7, 29.6, 29.5, 29.4, 25.9, 22.8, 14.3 ppm; HRMS (ESI) calcd for C$_{12}$H$_{24}$N$_4$O (M+) 240.1950. found 240.1947.

N-(2-azidoethyl)-2-iodobenzamide

As in the synthesis of N-(2-azidoethyl)tetradecanamide, 2-iodobenzoyl chloride (0.312 g, 1.17 mmol) was reacted with 2-azidoethanamine (0.101 g, 1.17 mmol) and triethylamine (0.237 g, 2.34 mmol) in dichloromethane (5 mL) to give N-(2-azidoethyl)-2-iodobenzamide (0.272 g, 74% yield). $^1$H NMR (300 MHz, CDCl$_3$) δ 7.84 (d, J=7.2 Hz, 1H), δ 7.33 (m, 2H), S 7.08 (t, J=3.3 Hz, 1H), δ 6.51 (s, 1H), δ 3.54 (s, 2H), δ 3.53 (s, 2H) ppm; $^{13}$C NMR (75 MHz, CDCl$_3$) δ 169.9, 141.9, 140.0, 131.5, 128.4, 128.4, 92.7, 50.8, 39.6 ppm; HRMS (ESI) calcd for C$_9$H$_{91}$N$_4$O (M+) 315.9821. found 315.9820.

N-(2-azidoethyl)-4-tert-butylbenzamide

As in the synthesis of N-(2-azidoethyl)tetradecanamide, 4-tert-butylbenzoyl chloride (0.244 g, 1.23 mmol) was reacted with 2-azidoethanamine (0.106 g, 1.23 mmol) and triethylamine (0.249 g, 2.47 mmol) in dichloromethane (5 mL) to give N-(2-azidoethyl)-4-tert-butylbenzamide (0.221 g, 73% yield). $^1$H NMR (300 MHz, CDCl$_3$) δ 7.73 (d, J=6.6 Hz, 2H), δ 7.43 (d, J=9.0 Hz, 2H), δ 6.95 (t, J=3.9 Hz, 1H), δ 3.59 (q, J=5.4, 5.7 Hz, 2H), δ 3.50 (t, J=5.1 Hz, 2H), δ 1.31 (s, 9H) ppm; $^{13}$C NMR (75 MHz, CDCl$_3$) δ 168.2, 155.4, 131.4, 127.2, 125.8, 51.1, 39.7, 35.2, 31.4 ppm; HRMS (ESI) calcd for C$_{13}$H$_{18}$N$_4$O (M+) 246.1480. found 246.1479.

N-(2-azidoethyl)-3,5-difluorobenzamide

As in the synthesis of N-(2-azidoethyl)tetradecanamide, 3,5-difluorobenzoyl chloride (0.219 g, 1.24 mmol) was reacted with 2-azidoethanamine (0.107 g, 1.24 mmol) and triethylamine (0.251 g, 2.48 mmol) in dichloromethane (5 mL) to give N-(2-azidoethyl)-3,5-difluorobenzamide (0.280 g, 59% yield). $^1$H NMR (300 MHz, CDCl$_3$) δ 7.32 (s, 2H), 7.29 (s, 1H), 6.91 (t, J=2.4 Hz, 1H), 3.58 (q, J=5.7, 5.1 Hz, 2H), 3.51 (t, J=4.8 Hz, 2H) ppm; $^{13}$C NMR (75 MHz, CDCl$_3$) δ 165.9, 164.7, 161.5, 161.4, 137.6, 110.7, 106.9, 50.7, 39.9 ppm; HRMS (ESI) calcd for C$_9$H$_8$F$_2$N$_4$O$_2$S (M+) 226.0666. found 226.0662.

N-(2-azidoethyl)-2,4,6-trichlorobenzamide

As in the synthesis of N-(2-azidoethyl)tetradecanamide, (0.301 g, 1.23 mmol) was reacted with 2-azidoethanamine (0.106 g, 1.23 mmol) and triethylamine (0.249 g, 2.47 mmol) in dichloromethane (5 mL) to give N-(2-azidoethyl)-2,4,6-trichlorobenzamide (0.317 g, 88% yield). $^1$H NMR (300 MHz, CDCl$_3$) δ 7.27 (2H, s), δ 6.88 (s, 1H), δ 3.54 (s, 2H), δ 3.53 (s, 2H) ppm; $_{13}$C NMR (75 MHz, CDCl$_3$) δ 164.4, 135.9, 134.3, 132.9, 128.2, 50.7, 39.4 ppm; HRMS (ESI) calcd for C$_9$H$_7$N$_4$O (M+) 291.9685. found 291.9681.

N-(2-azidoethyl)-2-naphthamide

As in the synthesis of N-(2-azidoethyl)tetradecanamide, 2-naphthoyl chloride (0.237 g, 1.24 mmol) was reacted with 2-azidoethanamine (0.107 g, 1.24 mmol) and triethylamine (0.252 g, 2.49 mmol) in dichloromethane (5 mL) to give N-(2-azidoethyl)-2-naphthamide (0.234 g, 77% yield). $^1$H NMR (300 MHz, CDCl$_3$) δ 8.69 (s, 1H), δ 7.84 (m, 4H), δ 7.50 (m, 2H), 6.97 (t, J=4.2 Hz, 1H), δ 3.68 (q, J=4.8, 1.2 Hz, 2H), 3.56 (t, J=3.0 Hz, 2H) ppm; $^{13}$C NMR (75 MHz, CDCl$_3$) δ 168.3, 135.1, 132.8, 131.5, 129.2, 128.8, 128.0, 127.9, 127.1, 123.8, 51.2, 39.8 ppm; HRMS (ESI) calcd for C$_{13}$H$_{12}$N$_4$O (M+) 240.1011. found 240.1007.

N-(2-azidoethyl)-4-heptylbenzamide

As in the synthesis of N-(2-azidoethyl)tetradecanamide, 4-heptylbenzoyl chloride (0.289 g, 1.21 mmol) was reacted with 2-azidoethanamine (0.104 g, 1.21 mmol) and triethylamine (0.245 g, 2.42 mmol) in dichloromethane (5 mL) to give N-(2-azidoethyl)-4-heptylbenzamide (0.260 g, 75% yield). $^1$H NMR (300 MHz, CDCl$_3$) δ 7.73 (d, J=7.8 Hz, 2H), δ 7.19 (d, J=7.8 Hz, 3H), δ 3.57 (q, J=5.7, 5.4 Hz, 2H), δ 3.47 (t, J=5.7 Hz, 2H), δ 2.61 (t, J=7.5 Hz, 2H), δ 1.61 (m, 2H), δ 1.26 (m, 8H), δ 0.87 (t, J=6.0 Hz, 3H) ppm; $^{13}$C NMR (75 MHz, CDCl$_3$) δ 168.3, 147.3, 131.7, 128.8, 127.4, 50.9, 39.7, 36.1, 32.0, 31.4, 29.4, 29.3, 22.9, 14.3 ppm; HRMS (ESI) calcd for C$_{16}$H$_{24}$N$_4$O (M+) 288.1950. found 288.1943.

N-(2-azidoethyl)-4-butylbenzamide

As in the synthesis of N-(2-azidoethyl)tetradecanamide, (0.242 g, 1.22 mmol) was reacted with 2-azidoethanamine (0.105 g, 1.22 mmol) and triethylamine (0.246 g, 2.43 mmol) in dichloromethane (5 mL) to give N-(2-azidoethyl)-4-butylbenzamide (0.224 g, 75% yield). $^1$H NMR (300 MHz, CDCl$_3$) δ 7.73 (d, J=8.4 Hz, 2H), δ 7.39 (t, J=1.8 Hz, 1H), δ 7.17 (d, J=8.1 Hz, 2H), δ 3.55 (q, J=8.7, 5.7 Hz, 2H), δ 3.45 (t, J=5.7 Hz, 2H), δ 2.60 (t, J=7.8 Hz, 2H), δ 1.56 (m, 2H), δ 1.30 (m, 2H), δ 0.90 (t, J=4.2 Hz, 3H) ppm; $^{13}$C NMR (75 MHz, CDCl$_3$) δ 168.5, 147.2, 131.7, 128.8, 127.4, 50.9, 39.7, 35.7, 33.5, 22.5, 14.1 ppm; HRMS (ESI) calcd for C$_{13}$H$_{18}$N$_4$O (M+) 246.1481. found 246.1476.

N-(2-azidoethyl)-4-hexylbenzamide

As in the synthesis of N-(2-azidoethyl)tetradecanamide, 4-hexylbenzoyl chloride (0.293 g, 1.30 mmol) was reacted with 2-azidoethanamine (0.112 g, 1.30 mmol) and triethylamine (0.264 g, 2.61 mmol) in dichloromethane (5 mL) to give N-(2-azidoethyl)-4-hexylbenzamide (0.299 g, 84% yield). $^1$H NMR (300 MHz, CDCl$_3$) δ 7.75 (d, J=8.1 Hz, 2H), δ 7.43 (t, J-3.9 Hz, 1H), δ 7.17 (d, J=7.8 Hz, 2H), δ 3.55 (q, J=6.3, 5.7 Hz, 2H), δ 3.46 (t, J=5.7 Hz, 2H), δ 2.59 (t, J=7.5 Hz, 2H), δ 1.58 (m, 2H), δ 1.29 (m, 4H), δ 0.87 (t, J=6.9 Hz, 3H) ppm; $^{13}$C NMR (75 MHz, CDCl$_3$) δ 168.6, 147.3, 131.7, 130.3, 128.8, 127.5, 50.9, 39.7, 35.9, 31.6, 31.1, 22.7, 14.2 ppm; HRMS (ESI) calcd for C$_{15}$H$_{22}$N$_4$O (M+) 274.1794. found 274.1789.

N-(2-azidoethyl)-4-pentylbenzamide

As in the synthesis of N-(2-azidoethyl)tetradecanamide, 4-pentylbenzoyl chloride (0.283 g, 1.35 mmol) was reacted with 2-azidoethanamine (0.116 g, 1.35 mmol) and triethylamine (0.273 g, 2.69 mmol) in dichloromethane (5 mL) to give N-(2-azidoethyl)-4-pentylbenzamide (0.267 g, 76% yield). $^1$H NMR (300 MHz, CDCl$_3$) δ 7.74 (d, J=8.1 Hz, 2H), δ 7.61 (t, J=5.1 Hz, 1H), δ 7.15 (d, J=8.4 Hz, 2H), δ 3.54 (q, J=5.7, 5.1 Hz, 2H), δ 3.44 (t, J=5.7 Hz, 2H), δ 2.58 (t, J=7.5 Hz, 2H), δ 1.57 (m, 2H), δ 1.26 (m, 4H), δ 0.86 (t, J=6.6 Hz, 3H) ppm; $^{13}$C NMR (75 MHz, CDCl$_3$) δ 168.6, 147.2, 131.7, 128.7, 127.5, 50.8, 39.7, 35.9, 31.6, 31.1, 22.7, 14.2 ppm; HRMS (ESI) calcd for C$_{14}$H$_{20}$N$_4$O (M+) 260.1637. found 260.1632.

N-(2-azidoethyl)biphenyl-4-carboxamide

As in the synthesis of N-(2-azidoethyl)tetradecanamide, (0.283 g, 1.31 mmol) was reacted with 2-azidoethanamine (0.113 g, 1.31 mmol) and triethylamine (0.264 g, 2.61 mmol) in dichloromethane (5 mL) to give N-(2-azidoethyl)biphenyl-4-carboxamide (0.297 g, 85% yield). $^1$H NMR (300 MHz, CDCl$_3$) δ 7.88 (d, 2H), δ 7.67 (m, 4H), δ 7.44 (m, 3H), δ 6.63 (s, 1H), δ 3.67 (q, J=6.0, 1.8 Hz, 2H), δ 3.58 (t, J=6.0 Hz, 2H) ppm; $^{13}$C NMR (75 MHz, CDCl$_3$) δ 167.8, 144.8, 140.1, 132.9, 129.2, 128.3, 127.8, 127.5, 127.4, 51.2, 39.7 ppm; HRMS (ESI) calcd for C$_{15}$H$_{14}$N$_4$O (M+) 266.1168. found 266.1162.

N-(2-azidoethyl)-4,5-dibromo-1-methyl-1H-pyrrole-2-carboxamide

As in the synthesis of N-(2-azidoethyl)tetradecanamide, (0.529 g, 1.38 mmol) was reacted with 2-azidoethanamine (0.119 g, 1.38 mmol) and triethylamine (0.279 g, 2.75 mmol) in dichloromethane (5 mL) to give N-(2-azidoethyl)-4,5-dibromo-1-methyl-1H-pyrrole-2-carboxamide (0.331 g, 69% yield). $^1$H NMR (300 MHz, CD$_3$OD) δ 6.84 (s, 1H), δ 3.91 (s, 3H), δ 3.50 (t, J=3.6 Hz, 2H), δ 3.25 (t, J=1.5 Hz, 2H) ppm; $^{13}$C NMR (75 MHz, CD$_3$OD) δ 161.7, 127.7, 114.7, 111.4, 97.8, 50.4, 38.9, 35.1 ppm; HRMS (ESI) calcd for C$_8$H$_9$N$_5$O (M+) 348.9174. found 348.9183.

N-(2-azidoethyl)-1H-pyrrole-2-carboxamide

As in the synthesis of N-(2-azidoethyl)tetradecanamide, (0.249 g, 1.17 mmol) was reacted with 2-azidoethanamine (0.101 g, 1.17 mmol) and triethylamine (0.237 g, 2.34 mmol) in dichloromethane (5 mL) to give N-(2-azidoethyl)-1H-pyrrole-2-carboxamide (0.137 g, 66% yield). $^1$H NMR (300 MHz, CD$_3$OD) δ 6.88 (d, J=1.5 Hz, 1H), δ 6.77 (d, J=2.4 Hz, 1H), δ 6.14 (t, J=2.4 Hz, 1H), δ 3.46 (t, J=5.7 Hz, 2H), δ 3.37 (q, J=5.7, 14.7 Hz, 2H) ppm; $^{13}$C NMR (75 MHz, CD$_3$OD) δ 162.9, 125.6, 122.2, 121.9, 110.9, 109.2, 50.6, 38.9 ppm; HRMS (ESI) calcd for C$_7$H$_9$N$_5$O (M+) 179.0807. found 179.0803.

N-(2-azidoethyl)-4-bromo-1H-pyrrole-2-carboxamide

As in the synthesis of N-(2-azidoethyl)tetradecanamide, (0.408 g, 1.34 mmol) was reacted with 2-azidoethanamine (0.115 g, 1.34 mmol) and triethylamine (0.270 g, 2.67 mmol) in dichloromethane (5 mL) to give N-(2-azidoethyl)-4-bromo-1H-pyrrole-2-carboxamide (0.299 g, 82% yield). $^1$H NMR (300 MHz, CD$_3$OD) δ 6.93 (s, 1H), δ 6.80 (s, 1H), δ 3.49 (t, J=0.6 Hz, 2H), δ 3.41 (t, J=0.9 Hz, 2H) ppm; $^{13}$C NMR (75 MHz, CD$_3$OD) δ 161.7, 126.1, 122.0, 112.4, 96.4, 50.5, 38.9 ppm; HRMS (ESI) calcd for C$_7$H$_8$BrN$_5$O (M+) 256.9912. found 256.9908.

N-(2-azidoethyl)-4-nonylbenzamide

As in the synthesis of N-(2-azidoethyl)tetradecanamide, the acid chloride (0.354 g, 1.40 mmol) was reacted with 2-azidoethanamine (0.121 g, 1.40 mmol) and triethylamine (0.284 g, 2.80 mmol) in dichloromethane (5 mL) to give N-(2-azidoethyl)-4-nonylbenzamide (0.339 g, 80% yield).

$^1$H NMR (300 MHz, CDCl$_3$) δ 6.21 (s, 1H), δ 3.40 (s, 4H), δ 2.19 (t, J=7.2 Hz, 2H), δ 1.62 (t, J=6.0 Hz, 2H), δ 1.22 (bs, 14H), δ 0.842 (t, J=6.3 Hz, 3H) ppm; $^{13}$C NMR (75 MHz, CDCl$_3$) δ 173.8, 51.1, 30.1, 36.8, 32.1, 29.8, 29.7, 29.6, 29.5, 29.2, 25.9, 22.9, 14.3 ppm; HRMS (ESI) calcd for C$_{14}$H$_{28}$N$_4$O (M+) 268.2263. found 268.2259.

N-(2-azidoethyl)-4-nonylbenzamide

As in the synthesis of N-(2-azidoethyl)tetradecanamide, (0.383 g, 1.43 mmol) the acid chloride was reacted with 2-azidoethanamine (0.124 g, 1.43 mmol) and triethylamine (0.290 g, 2.87 mmol) in dichloromethane (5 mL) to give N-(2-azidoethyl)-4-nonylbenzamide (0.441 g, 97% yield). $^1$H NMR (300 MHz, CDCl$_3$) δ 7.72 (d, 2H), δ 7.26 (t, 1H), δ 7.18 (d, 2H), δ 3.57 (q, 2H), δ 3.45 (t, 2H), δ 2.60 (t, 2H), δ 1.58 (m, 2H), δ 1.27 (m, 12H), δ 0.86 (t, 3H) ppm; $^{13}$C NMR (75 MHz, CDCl$_3$) δ 168.5, 147.3, 131.7, 128.8, 127.4, 50.9, 39.7, 36.1, 32.1, 31.5, 29.8, 29.7, 29.6, 29.5, 22.9, 14.4 ppm; HRMS (ESI) calcd for C$_{18}$H$_{28}$N$_4$O (M+) 316.2263. found 316.2268.

N-(2-azidoethyl)-4-octylbenzamide

As in the synthesis of N-(2-azidoethyl)tetradecanamide, (0.262 g, 1.19 mmol) the acid chloride was reacted with 2-azidoethanamine (0.103 g, 1.19 mmol) and triethylamine (0.242 g, 2.39 mmol) in dichloromethane (5 mL) to give N-(2-azidoethyl)-4-octylbenzamide (0.220 g, 69% yield). $^1$H NMR (300 MHz, CDCl$_3$) δ 7.73 (d, 2H), δ 7.37 (t, 1H), δ 7.17 (d, 2H), 63.56 (q, 2H), δ 3.44 (t, 2H), δ 2.59 (t, 2H), δ 1.58 (m, 2H), δ 1.27 (m, 10H), 60.86 (t, 3H) ppm; $^{13}$C NMR (75 MHz, CDCl$_3$) δ 168.4, 147.3, 131.7, 128.8, 127.4, 50.9, 39.7, 36.1, 32.1, 31.5, 29.7, 29.5, 29.5, 22.9, 14.3 ppm; HRMS (ESI) calcd for C$_{17}$H$_{28}$N$_4$O (M+) 302.2107. found 302.2104.

(E)-N-(2-azidoethyl)-2-methyl-3-phenylaycrylamide

To a 25 mL round-bottomed flask equipped with a magnetic stir bar was added (E)-2-methyl-3-phenylacrylic acid (0.0.512 g, 3.15 mmol) and dichloromethane (10 mL). Oxalyl chloride (0.400 g, 3.15 mmol) was added dropwise to the reaction mixture and allowed to stir for one hour. Then, the reaction mixture was concentrated de vacuo. To the crude mixture was then added dichloromethane (10 mL), 2-azidoethanamine (0.299 g, 3.47 mmol) and then triethylamine (0.351 g, 3.47 mmol) and allowed to stir for two hours. The reaction mixture was then concentrated de vacuo and then purified via silica gel column chromatography (100% dichloromethane to 1:40 methanol:dichloromethane) to give (E)-N-(2-azidoethyl)-2-methyl-3-phenylacrylamide (0.698 g, 96% yield). $^1$H NMR (300 MHz, CDCl$_3$) δ 7.39 (m, 6H), δ 7.01 (s, 1H), δ 3.51 (t, J=4.5 Hz, 2H), δ 3.45 (t, J=4.8 Hz, 2H), δ 2.13 (s, 3H) ppm; $^{13}$C NMR (75 MHz, CDCl$_3$) δ 170.5, 136.2, 134.5, 132.0, 130.3, 129.6, 128.9, 128.6, 128.3, 50.9, 39.8, 14.5 ppm; HRMS (ESI) calcd for C$_{12}$H$_{14}$N$_4$O (M+) 230.1168. found 230.1165.

N-(2-azidoethyl)-2',4'-difluoro-3-hydroxybiphenyl-4-carboxamide

To a 25 mL round-bottomed flask equipped with a magnetic stir bar was added 2',4'-difluoro-3-hydroxybiphenyl-4-carboxylic acid (0.301, 1.20 mmol), N,N-Dimethylformamide (5 mL), N,N'-Dicyclohexylcarbodiimide (0.248 g, 1.20 mmol) and n-methylmorpholine (0.25 mL). The reaction mixture was cooled to 0° C. and allowed to stir. Then, 2-azidoethanamine (0.1037 g, 1.20 mmol) was added dropwise and allowed to slowly warm to room temperature while stirring for 24 hr. The reaction mixture was diluted with water, extracted with dichloromethane, washed with 1N HCl, washed with saturated sodium bicarbonate, washed with brine and then concentrated de vacuo. The resulting residue was then purified via silica gel column chromatography (1:40 methanol:dichloromethane to 1:10 methanol:dichloromethane) to give N-(2-azidoethyl)-2',4'-difluoro-3-hydroxybiphenyl-4-carboxamide (0.232 g, 61% yield). $^1$H NMR (300 MHz, CDCl$_3$) δ 7.60 (s, 1H), δ 7.47 (d, J=6.0 Hz, 1H), δ 7.29 (m, 2H), δ 7.02 (d, J=6.6 Hz, 1H), δ 6.88 (m, 2H) ppm; $^{13}$C NMR (75 MHz, CDCl$_3$) δ 170.3, 160.8, 135.1, 131.3, 131.2, 131.3, 131.2, 126.8, 118.8, 114.6, 112.0, 111.8, 104.8, 104.6, 104.3, 50.7, 39.3 ppm; HRMS (ESI) calcd for C$_{15}$H$_{12}$F$_2$N$_4$O$_3$(M+) 318.0928. found 318.0933.

General Procedure for Click Reactions and Subsequent Boc Deprotection:

The terminal alkyne (1.0 equiv.) was dissolved in a 1:1:1 mixture of ethanol, water and methylene chloride (ca. 9 mL per 0.300 g of terminal alkyne). To this solution, the appropriate azide (1.0 equiv.) was added while stirring vigorously at room temperature. Copper (II) sulfate (15 mol %) and sodium ascorbate (45 mol %) were then added sequentially to the solution. Reaction mixtures were allowed to stir until completion via TLC analysis (12-24 hrs). The solvents were then removed de vacuo in which the resulting residue was dissolved in dichloromethane and purified via silica gel column chromatography (1:40 methanol:dichloromethane to 1:10 methanol:dichloromethane). To remove the Boc protecting group, the resulting product was then dissolved in a 1:4 trifluoroacetic acid:dichloromethane mixture and allowed to stir for 5 hr. Upon completion, the reaction mixture was concentrated de vacuo and then left on a high vacuum overnight. Then, methanol supplemented with HCl was added to the product forming the HCl salt of the deprotected product and then was concentrated de vacuo. The resulting residue was washed with diethyl ether and then placed on a high vacuum overnight.

N-(2-(4-(5-(2-amino-1H-imidazol-4-yl)pentyl)-1H-1,2,3-triazol-1-yl)ethyl)-2-(phenylthio)acetamide hydrochloride tert-butyl 2-amino-4-(hept-6-ynyl)-1H-imidazole-1-carboxylate (0.112 g, 0.405 mmol) was reacted with N-(2-azidoethyl)-2-(phenylthio)acetamide (0.096 g, 0.405 mmol) following the general click procedure to give tert-butyl 2-amino-4-(5-(1-(2-(2-(phenylthio)acetamido)ethyl)-1H-1,2,3-triazol-4-yl)pentyl)-1H-imidazole-1-carboxylate $^1$H NMR (300 MHz, CDCl$_3$) δ 7.45 (s, 1H), δ 7.19 (m, 5H), δ 7.13 (s, 1H), δ 6.43 (s, 1H), δ 6.13 (bs, 2H), δ 4.29 (s, 2H), δ 3.68 (s, 2H), δ 3.57 (s, 2H), δ 2.56 (s, 2H), δ 2.35 (s, 2H), δ 1.52 (m, 15H) ppm; $^{13}$C NMR (75 MHz, CDCl$_3$) δ 187.8, 172.0, 169.1, 162.4, 156.9, 135.0, 129.5, 128.3, 126.8, 121.8, 85.00, 49.4, 39.9, 37.4, 29.4, 28.9, 28.4, 28.2, 27.6, 25.6 ppm; HRMS (ESI) calcd for C$_{25}$H$_{35}$N$_7$O$_3$S (M+) 513.2522. found 513.2522, which was subsequently deprotected to give N-(2-(4-(5-(2-amino-1H-imidazol-4-yl)pentyl)-1H-1,2,3-triazol-1-yl)ethyl)-2-(phenylthio)acetamide hydrochloride (0.133 g, 73% yield). $^1$H NMR (300 MHz, CD$_3$OD) δ 8.47 (s, 1H), δ 7.30 (s, 4H), δ 7.19 (s, 1H), δ 6.58 (s, 1H), δ 4.66 (s, 2H), δ 3.76 (s, 2H), δ 3.64 (s, 2H), δ 2.84 (s, 2H), δ 2.34 (s, 2H), δ 1.73 (s, 2H), δ 1.64 (s, 2H), δ 1.26 (s, 2H) ppm; $^{13}$C NMR (75 MHz, CD$_3$OD) δ 170.9, 159.3, 158.9, 147.2, 135.6, 128.1, 128.9, 127.6, 126.6, 108.7, 108.6, 52.-, 39.1, 37.5, 37.2, 36.6, 36.1, 30.8, 28.1, 27.9, 27.7, 24.2, 23.7, 23.6 ppm; HRMS (ESI) calcd for C$_{20}$H$_{27}$N$_7$OS (M+) 413.1998. found 413.1991.

N-(2-(4-(5-(2-amino-1H-imidazol-4-yl)pentyl)-1H-1,2,3-triazol-1-yl)ethyl)thiophene-2-sulfonamide hydrochloride tert-butyl 2-amino-4-(hept-6-ynyl)-1H-imidazole-1-carboxylate (0.105 g, 0.379 mmol) was reacted with N-(2-azidoethyl)thiophene-2-sulfonamide (0.099 g, 0.379 mmol) following the general click procedure to give tert-butyl 2-amino-4-(5-(1-(2-(thiophene-2-sulfonamido)ethyl)-1H-1,2,3-triazol-4-yl)pentyl)-1H-imidazole-1-carboxylate $^1$H NMR (300 MHz, CDCl$_3$) δ 7.49 (s, 3H), δ 7.39 (s, 1H), δ 6.99 (s, 1H), δ 6.41 (bm, 3H), δ 4.43 (s, 2H), δ 3.42 (s, 2H), δ 2.54 (s, 2H), δ 2.09 (s, 2H), δ 1.51 (m, 13H), δ 1.19 (s, 2H) ppm; $^{13}$C NMR (75 MHz, CDCl$_3$) δ 150.8, 149.4, 148.1, 141.1, 138.3, 132.2, 132.1, 127.7, 122.6, 85.2, 53.8, 50.2, 43.2, 31.2, 29.9, 29.2, 28.8, 28.1, 25.5 ppm; HRMS (ESI) calcd for C$_{21}$H$_{31}$N$_7$O$_4$S$_2$(M+) 509.1879. found 509.1879, which was subsequently deprotected to give N-(2-(4-(5-(2-amino-1H-imidazol-4-yl)pentyl)-1H-1,2,3-triazol-1-yl)ethyl)thiophene-2-sulfonamide hydrochloride (0.098 g, 58% yield). $^1$H NMR (400 MHz, CD$_3$OD) δ 8.37 (s, 1H), δ 7.76 (s, 1H), δ 7.57 (s, 1H), δ 7.11 (s, 1H), δ 6.46 (s, 1H), δ 4.79 (s, 2H), δ 3.55 (s, 2H), δ 2.50 (s, 2H), δ 1.66-1.18 (bm, 8H) ppm; $^{13}$C NMR (100 MHz, CD$_3$OD) δ 175.6, 155.6, 147.2, 140.9, 132.7, 132.3, 127.8, 127.7, 108.8, 53.1, 42.2, 36.8, 28.1, 27.8, 27.5, 24.9, 24.3, 23.8 ppm; HRMS (ESI) calcd for C$_{16}$H$_{23}$N$_7$O$_2$S$_2$(M+) 409.1355. found 409.1354.

N-(2-(4-(5-(2-amino-4H-imidazol-4-yl)pentyl)-1H-1,2,3-triazol-1-yl)ethyl)-5-(dimethylamino)naphthalene-1-sulfonamide hydrochloride tert-butyl 2-amino-4-(hept-6-ynyl)-1H-imidazole-1-carboxylate (0.112 g, 0.403 mmol) was reacted with N-(2-azidoethyl)-5-(dimethylamino)naphthalene-1-sulfonamide (0.140 g, 0.403 mmol) following the general click procedure to give tert-butyl 2-amino-4-(5-(1-(2-(5-(dimethylamino)naphthalene-1-sulfonamido)ethyl)-1H-1,2,3-triazol-4-yl)pentyl)-1H-imidazole-1-carboxylate $^1$H NMR (300 MHz, CDCl$_3$) δ 8.48 (d, J=8.4 Hz, 1H), δ 8.24 (d, J=8.4 Hz, 1H), δ 8.17 (d, J=7.2 Hz, 1H), δ 7.44 (m, 3H), δ 7.09 (s, 1H), δ 7.07 (d, J=7.5 Hz, 1H), δ 6.44 (s, 1H), δ 6.09 (bs, 2H), δ 4.32 (s, 2H), δ 3.36 (s, 2H), δ 2.52 (s, 2H), δ 2.22 (s, 2H), δ 1.43 (m, 13H), δ 1.22 (s, 2H) ppm; $^{13}$C NMR (75 MHz, CDCl$_3$) δ 176.9, 152.1, 149.6, 148.0, 138.6, 135.1, 130.7, 130.1, 129.7, 129.4, 128.5, 123.3, 122.4, 119.1, 115.5, 84.9, 67.5, 50.3, 50.2, 45.6, 42.9, 37.9, 29.1, 28.9, 28.2, 28.0, 25.5 ppm; HRMS (ESI) calcd for C$_{29}$H$_{40}$N$_8$O$_4$S (M+) 596.2893. found 596.2881, which was subsequently deprotected to give N-(2-(4-(5-(2-amino-1H-imidazol-4-yl)pentyl)-1H-1,2,3-triazol-1-yl)ethyl)-5-(dimethylamino)naphthalene-1-sulfonamide hydrochloride (0.139 g, 65% yield). $^1$H NMR (400 MHz, CD$_3$OD) δ 8.70 (t, J=4.8 Hz, 2H), δ 8.31 (s, 1H), δ 8.08 (s, 2H), δ 7.82 (s, 2H), δ 6.43 (s, 1H), δ 4.55 (s, 2H), δ 3.32 (s, 8H), 2.63 (s, 2H), δ 2.48 (s, 2H), δ 1.66 (s, 4H), δ 1.40 (s, 2H) ppm; $^{13}$C NMR (100 MHz, CD$_3$OD) δ 159.9, 147.3, 140.7, 136.8, 129.9, 129.3, 127.8, 127.7, 126.5, 119.3, 108.6, 108.4, 76.7, 67.3, 51.5, 42.3, 37.4, 36.5, 28.3, 27.9, 27.6, 24.1, 24.0, 23.7 ppm; HRMS (ESI) calcd for C$_{24}$H$_{32}$N$_8$O$_2$S (M+) 496.2369. found 496.2359.

tert-butyl 2-amino-4-(5-(1-(2-(phenylsulfonamido)ethyl)-1H-1,2,3-triazol-4-yl)pentyl)-1H-imidazole-1-carboxylate hydrochloride tert-butyl 2-amino-4-(hept-6-ynyl)-1H-imidazole-1-carboxylate (0.114 g, 0.410 mmol) was reacted with N-(2-azidoethyl)benzenesulfonamide (0.104 g, 0.410 mmol) following the general click procedure to give tert-butyl 2-amino-4-(5-(1-(2-(phenylsulfonamido)ethyl)-1H-1,2,3-triazol-4-yl)pentyl)-1H-imidazole-1-carboxylate $^1$H NMR (300 MHz, CDCl$_3$) δ 7.81 (d, J=6.9 Hz, 2H), δ 7.44 (m, 5H), δ 6.44 (s, 1H), δ 6.07 (s, 2H), δ 4.42 (t, J=5.7 Hz, 2H), δ 3.36 (t, J=5.4 Hz, 2H), δ 2.57 (t, J=7.2 Hz, 2H), δ 2.20 (s, 2H), δ 1.47 (m, 13H), δ 1.29 (s, 2H) ppm; $^{13}$C NMR (75 MHz, CDCl$_3$) δ 202.9, 149.5, 148.2, 140.2, 132.8, 129.4, 127.1, 122.5, 106.5, 85.0, 53.7, 50.3, 42.9, 32.7, 31.2, 29.9, 29.2, 28.9, 28.2, 26.3, 25.5 ppm; HRMS (ESI) calcd for C$_{23}$H$_{33}$N$_7$O$_4$S (M+) 503.2315. found 503.2310, which was subsequently deprotected to give tert-butyl 2-amino-4-(5-(1-(2-(phenylsulfonamido)ethyl)-1H-1,2,3-triazol-4-yl)pentyl)-1H-imidazole-1-carboxylate hydrochloride (0.142 g, 64% yield). $^1$H NMR (300 MHz, CD$_3$OD) δ 7.81 (d, J=6.6 Hz, 2H), δ 7.56 (m, 4H), δ 6.47 (s, 1H), δ 4.62 (s, 2H), δ 3.41 (s, 2H), δ 2.78 (s, 2H), δ 2.48 (s, 2H), δ 1.72 (s, 2H), δ 1.63 (s, 2H), δ 1.42 (s, 2H) ppm; $^{13}$C NMR (75 MHz, CD$_3$OD) δ 176.2, 165.6, 159.9, 147.3, 140.2, 132.8, 129.3, 127.7, 126.8, 108.5, 108.4, 515.8, 42.3, 28.1, 27.9, 27.6, 24.1 ppm; HRMS (ESI) calcd for C$_{18}$H$_{25}$N$_7$O$_2$S (M+) 403.1790. found 403.1781.

N-(2-(4-(5-(2-amino-1H-imidazol-4-yl)pentyl)-1H-1,2,3-triazol-1-yl)ethyl)-2,3,4,5,6-pentamethylbenzenesulfonamide hydrochloride tert-butyl 2-amino-4-(hept-6-ynyl)-1H-imidazole-1-carboxylate (0.120 g, 0.434 mmol) was reacted with N-(2-azidoethyl)-2,3,4,5,6-pentamethylbenzenesulfonamide (0.141 g, 0.434 mmol) following the general click procedure to give tert-butyl 2-amino-4-(5-(1-(2-(2,3,4,5,6-pentamethylphenylsulfonamido)ethyl)-1H-1,2,3-triazol-4-yl)pentyl)-1H-imidazole-1-carboxylate $^1$H NMR (300 MHz, CDCl$_3$) δ 7.30 (s, 1H), δ 7.01 (s, 1H), δ 6.44 (s, 1H), δ 6.17 (s, 2H), δ 4.35 (s, 2H), δ 3.34 (s, 2H), δ2.47 (s, 2H), δ 2.48 (s, 6H), δ 2.20 (m, 11H), δ 1.43 (m, 15H) ppm; $^{13}$C NMR (75 MHz, CDCl$_3$) δ 149.6, 148.1, 139.7, 136.2, 134.9, 134.3, 122.4, 84.9, 53.7, 50.2, 42.5, 31.1, 29.3, 28.9, 28.4, 28.2, 25.6, 19.1, 17.9, 17.2 ppm; HRMS (ESI) calcd for C$_{28}$H$_{43}$N$_7$O$_4$S (M+) 573.3097. found 573.3086, which was subsequently deprotected to give N-(2-(4-(5-(2-amino-1H-imidazol-4-yl)pentyl)-1H-1,2,3-triazol-1-yl)ethyl)-2,3,4,5,6-pentamethylbenzenesulfonamide hydrochloride (0.143 g, 76% yield). $^1$H NMR (400 MHz, CD$_3$OD) δ 8.11 (s, 1H), δ 6.42 (s, 1H), δ 4.48 (s, 2H), δ 3.34 (s, 2H), δ 2.65 (s, 2H), δ 2.40 (s, 8H), δ 2.12 (s, 9H), δ 1.58 (s, 4H), δ 1.19 (s, 2H) ppm; $^{13}$C NMR (100 MHz, CD$_3$OD) δ 159.9, 147.3, 139.6, 136.1, 134.8, 134.0, 127.8, 127.6, 108.6, 108.4, 54.1, 51.5, 41.8, 36.5, 28.2, 28.1, 27.7, 24.1, 23.7, 18.2, 16.8, 16.1 ppm; HRMS (ESI) calcd for C$_{23}$H$_{35}$N$_7$O$_2$S (M+) 473.2573. found 473.2565.

(E)-N-(2-(4-(5-(2-amino-1H-imidazol-4-yl)pentyl)-1H-1,2,3-triazol-1-yl)ethyl)-2-methyl-3-phenylacrylamide hydrochloride tert-butyl 2-amino-4-(hept-6-ynyl)-1H-imidazole-1-carboxylate (0.1103 g, 0.397 mmol) was reacted with (E)-N-(2-azidoethyl)-2-methyl-3-phenylacrylamide (0.092 g, 0.397 mmol) following the general click procedure to give (E)-tert-butyl 2-amino-4-(5-(1-(2-(2-methyl-3-phenylacrylamido)ethyl)-1H-1,2,3-triazol-4-yl)pentyl)-1H-imidazole-1-carboxylate $^1$H NMR (300 MHz, CDCl$_3$) δ 7.28 (m, 7H), δ 6.94 (s, 2H), 6.06 (s, 2H), δ 4.46 (s, 2H), δ 3.79 (s, 2H), δ 2.61 (s, 2H), δ 2.27 (s, 2H), δ 1.99 (s, 3H), δ 1.49 (bs, 11H), δ 1.18 (s, 4H) ppm; $^{13}$C NMR (75 MHz, CDCl$_3$) δ 192.4, 191.3, 170.4, 150.9, 140.2, 136.2, 134.8, 131.6, 129.6, 128.6, 128.1, 122.1, 95.8, 85.2, 74.3, 53.7, 52.6, 50.7, 49.4, 40.1, 29.9, 29.3, 28.9, 28.2, 25.6, 14.4 ppm; HRMS (ESI) calcd for C$_{27}$H$_{37}$N$_7$O$_3$ (M+) 507.2958. found 507.2942, which was subsequently deprotected to give (E)-N-(2-(4-(5-(2-amino-1H-imidazol-4-yl)pentyl)-1H-1,2,3-triazol-1-yl)ethyl)-2-methyl-3-phenylacrylamide hydrochloride (0.148 g, 84% yield). $^1$H NMR (400 MHz, CD$_3$OD) δ 8.78 (s, 1H), δ 7.33 (s, 4H), δ 7.26 (s, 1H), δ 7.19 (s, 1H), δ 6.42 (s, 1H), δ 4.78 (s, 2H), δ 3.84 (s, 2H), δ 2.87 (s, 2H), δ 2.44 (s, 2H), δ 1.99 (s, 3H), δ 1.76 (s, 2H), δ 1.59 (s, 2H), δ 1.42 (s, 2H) ppm; $^{13}$C NMR (100 MHz, CD$_3$OD) δ 174.7, 136.0, 134.4, 131.5, 129.3, 128.7, 128.3, 128.0, 127.6, 108.6, 94.6, 53.1, 39.2, 27.6, 27.9, 27.7, 27.6, 24.1, 23.8, 23.1, 14.3, 13.4 ppm; HRMS (ESI) calcd for C$_{22}$H$_{29}$N$_7$O (M+) 407.2434. found 407.2429.

N-(2-(4-(5-(2-amino-1H-imidazol-4-yl)pentyl)-1H-1,2,3-triazol-1-yl)ethyl)cinnamamide hydrochloride tert-butyl 2-amino-4-(hept-6-ynyl)-1H-imidazole-1-carboxylate (0.106 g, 0.384 mmol) was reacted with N-(2-azidoethyl)cinnamamide (0.083 g, 0.384 mmol) following the general click procedure to give (E)-tert-butyl 2-amino-4-(5-(1-(2-cinnamamidoethyl)-1H-1,2,3-triazol-4-yl)pentyl)-1H-imidazole-1-carboxylate $^1$H NMR (300 MHz, CDCl$_3$) δ 7.67 (s, 1H), δ 7.51 (d, J=11.1 Hz, 1H), δ 7.28 (m, 6H), δ 6.45 (t, J=14.1 Hz, 2H), δ 6.08 (s, 2H), δ 4.47 (s, 2H), δ 3.79 (s, 2H), δ 2.57 (s, 2H), δ 2.23 (s, 2H), δ 1.50 (bs, 13H), δ 1.28 (s, 2H) ppm; $^{13}$C NMR (75 MHz, CDCl$_3$) δ 166.9, 150.4, 149.5, 148.3, 141.2, 138.9, 134.9, 129.9, 128.9, 128.0, 122.1, 120.8, 106.5, 84.8, 53.7, 49.5, 39.9, 31.1, 29.3, 28.9, 28.3, 28.2, 25.6 ppm; HRMS (ESI) calcd for C$_{26}$H$_{35}$N$_7$O$_3$ (M+) 493.2801. found 493.2800, which was subsequently deprotected to give N-(2-(4-(5-(2-amino-1H-imidazol-4-yl)pentyl)-1H-1,2,3-triazol-1-yl)ethyl)cinnamamide hydrochloride (0.097 g, 59% yield). $^1$H NMR (400 MHz, CD$_3$OD) δ 8.10 (s, 1H), δ 7.49 (s, 3H), δ 7.32 (s, 3H), δ 6.30 d, J=10.8 Hz, 1H), δ 6.39 (s, 1H), δ 4.66 (s, 2H), δ 3.83 (s, 2H), δ 2.73 (s, 2H), δ 2.40 (s, 2H), δ 1.57 (s, 2H), δ 1.55 (s, 2H), δ 1.36 (s, 2H) ppm; $^{13}$C NMR (100 MHz, CD$_3$OD) δ 167.8, 160.5, 150.2, 147.3, 141.1, 134.8, 130.7, 129.9, 128.8, 127.8, 127.6, 124.9, 23 9, 120.2, 108.5, 108.3, 53.1, 39.3, 36.5, 30.6, 28.4, 28.1, 27.6, 26.5, 24.2, 24.1, 23.7 ppm; HRMS (ESI) calcd for C$_{21}$H$_{27}$N$_7$O (M+) 393.2277. found 393.2273.

N-(2-(4-(5-(2-amino-1H-imidazol-4-yl)pentyl)-1H-1,2,3-triazol-1-yl)ethyl)heptadec-8-enamide hydrochloride tert-butyl 2-amino-4-(hept-6-ynyl)-1H-imidazole-1-carboxylate (g, mmol) was reacted with N-(2-azidoethyl)octadec-9-enamide (g, mmol) following the general click procedure to give tert-butyl 2-amino-4-(5-(1-(2-heptadec-8-enamidoethyl)-1H-1,2,3-triazol-4-yl)pentyl)-1H-imidazole-1-carboxylate $^1$H NMR (300 MHz, CDCl$_3$) δ 7.26 (s, 1H), δ 6.81 (s, 1H), δ 6.42 (s, 2H), δ 5.88 (s, 1H), δ 5.27 (s, 2H), δ 4.38 (s, 2H), δ 3.65 (s, 2H), δ 2.60 (s, 2H), δ 2.09 (s, 2H), δ 1.53-1.01 (m, 35H), 0.79 (t, J=6.3 Hz, 3H) ppm; $^{13}$C NMR (75 MHz, CDCl$_3$) δ 174.2, 173.8, 148.3, 130.3, 130.1, 129.9, 129.8, 121.9, 85.1, 67.1, 49.5, 39.5, 39.1, 38.0, 37.7, 36.7, 36.6, 32.8, 32.3, 32.1, 31.7, 29.9, 29.8, 29.7, 29.5, 29.3, 29.2, 28.9, 28.7, 28.1, 28.0, 27.9, 27.4, 27.3, 27.3, 26.9, 25.9, 25.6, 25.3, 22.9, 22.8, 22.6, 14.3, 14.2 ppm; HRMS (ESI) calcd for C$_{35}$H$_{61}$N$_7$O$_3$(M+) 627.4836. found 627.4823, which was subsequently deprotected to give N-(2-(4-(5-(2-amino-1H-imidazol-4-yl)pentyl)-1H-1,2,3-triazol-1-yl)ethyl)heptadec-8-enamide hydrochloride (0.128 g, 66% yield). $^1$H NMR (400 MHz, CD$_3$OD) δ 8.36 (s, 1H), δ 6.96 (s, 1H), δ 6.45 (s, 1H), δ 6.09 (s, 1H), δ 4.58 (s, 2H), δ 3.58 (s, 2H), δ 2.75 (s, 2H), δ 2.10 (s, 2H), δ 1.96 (s, 4H), δ 1.69 (s, 2H), δ 1.41 (m, 4H), 1.23 (s, 24H), δ 0.84 (s, 3H) ppm; $^{13}$C NMR (100 MHz, CD$_3$OD) δ 175.5, 158.8, 155.7, 147.3, 129.7, 129.6, 127.6, 108.5, 94.6, 76.7, 51.3, 50.4, 48.6, 48.4, 48.2, 47.9, 47.8, 47.5, 47.3, 38.9, 37.5, 36.6, 45.9, 45.8, 33.9, 32.6, 31.9, 31.5, 29.8, 29.5, 29.4, 29.3, 29.2, 29.1, 28.2, 27.8, 27.0, 25.8, 24.9, 24.2, 23.8, 22.5, 13.5, 13.3 ppm; HRMS (ESI) calcd for C$_{30}$H$_{53}$N$_7$O (M+) 527.4312. found 527.4298.

N-(2-(4-(5-(2-amino-1H-imidazol-4-yl)pentyl)-1H-1,2,3-triazol-1-yl)ethyl)decanamide hydrochloride tert-butyl 2-amino-4-(hept-6-ynyl)-1H-imidazole-1-carboxylate (0.114 g, 0.412 mmol) was reacted with N-(2-azidoethyl)decanamide (0.099 g, 0.412 mmol) following the general click procedure to give tert-butyl 2-amino-4-(5-(1-(2-decanamidoethyl)-1H-1,2,3-triazol-4-yl)pentyl)-1H-imidazole-1-carboxylate $^1$H NMR (400 MHz, CDCl$_3$) δ 7.23 (s, 1H), δ 6.57 (s, 1H), δ 6.43 (s, 1H), δ 6.09 (s, 2H), δ 4.38 (s, 2H), δ 3.67 (s, 2H), δ 2.61 (t, J=5.4 Hz, 2H), δ 2.08 (s, 2H), δ 2.08 (t, J=5.7 Hz, 2H), δ 1.42 (m, 15H), δ 1.17 (m, 14H), δ 0.79 (t, J=4.5 Hz, 3H) ppm; $^{13}$C NMR (100 MHz, CDCl$_3$) δ 174.2, 149.7, 148.4, 138.8, 121.9, 106.6, 84.9, 49.5, 39.5, 36.7, 32.1, 31.3, 30.6, 29.9, 29.7, 29.6, 29.5, 29.5, 29.3, 29.0, 28.3, 28.2, 25.9, 25.6, 25.5, 22.9, 14.3 ppm; HRMS (ESI) calcd for C$_{27}$H$_{47}$N$_7$O$_3$(M+) 517.3740. found 517.3736, which was subsequently deprotected to give N-(2-(4-(5-(2-amino-1H-imidazol-4-yl)pentyl)-1H-1,2,3-triazol-1-yl)ethyl)decanamide hydrochloride (0.137 g, 73% yield). $^1$H NMR (300 MHz, CD$_3$OD) δ 8.55 (s, 1H), δ 6.53 (s, 1H), 4.72 (s, 2H), δ 3.75 (s, 2H), 2.89 (s, 2H), δ 2.54 (t, J=6.8 Hz, 2H), δ 2.16 (t, J=7.2 Hz, 2H), δ 1.81 (s, 2H), δ 1.69 (s, 2H), δ 1.49 (m, 4H), δ 1.28 (s, 12H), δ 0.89 (t, 3H) ppm; $^{13}$C NMR (75 MHz, CD$_3$OD) δ 175.7, 147.3, 128.5, 127.6, 125.1, 120.8, 108.6, 108.4, 105.6, 63.1, 59.3, 52.5, 48.6, 48.3, 48.1, 47.9, 47.7, 47.5, 57.3, 38.7, 336.6, 35.8, 36.6, 35.8, 31.8, 30.6, 29.4, 29.3, 29.3, 29.2, 28.0, 27.8, 27.7, 25.8, 24.1, 23.9, 23.3, 22.6 ppm; HRMS (ESI) calcd for C$_{22}$H$_{39}$N$_7$O (M+) 417.3216. found 417.3209.

N-(2-(4-(5-(2-amino-1H-imidazol-4-yl)pentyl)-1H-1,2,3-triazol-1-yl)ethyl)dodecanamide hydrochloride tert-butyl 2-amino-4-(hept-6-ynyl)-1H-imidazole-1-carboxylate (0.107 g, 0.387 mmol) was reacted with N-(2-azidoethyl)dodecanamide (0.104 g, 0.387 mmol) following the general click procedure to give tert-butyl 2-amino-4-(5-(1-(2-dodecanamidoethyl)-1H-1,2,3-triazol-4-yl)pentyl)-1H-imidazole-1-carboxylate $^1$H NMR (300 MHz, CDCl$_3$) δ 7.36 (s, 1H), δ 6.94 (s, 1H), δ 6.49 (s, 1H), δ 6.23 (s, 2H), δ 4.46 (t, J=5.1 Hz, 2H), δ 3.74 (q, J=5.1, 5.7 Hz, 2H), δ 2.68 (t, J=7.5 Hz, 2H), δ 2.34 (t, J=6.9 Hz, 2H), δ 2.16 (t, J=7.5 Hz, 2H), δ 1.54 (m, 13H), δ 1.47 (m, 2H), δ 1.24 (m, 18H), δ 0.87 (t, J=6.6 Hz, 3H) ppm; $^{13}$C NMR (75 MHz, CDCl$_3$) δ 174.3, 150.4, 149.5, 148.3, 138.5, 121.9, 106.5, 84.9, 49.5, 39.5, 36.6, 34.1, 32.1, 29.8, 29.8, 29.7, 29.6, 29.5, 29.3, 28.9, 28.2, 28.1, 29.0, 26.9. 25.6, 22.9, 14.3 ppm; HRMS (ESI) calcd for C$_{29}$H$_{51}$N$_7$O$_3$ (M+) 545.4053. found 545.4053, which was subsequently deprotected to give N-(2-(4-(5-(2-amino-1H-imidazol-4-yl)pentyl)-1H-1,2,3-triazol-1-yl)ethyl)dodecanamide hydrochloride (0.155 g, 83% yield). $^1$H NMR (400 MHz, CD$_3$OD) δ 8.31 (s, 1H), δ 6.49 (s, 1H), δ 4.63 (s, 2H), δ 3.97 (s, 2H), δ 2.81 (s, 2H), δ 2.51 (t, J=7.2 Hz, 2H), δ 2.14 (t, J=7.2 Hz, 2H), δ 1.76 (s, 2H), δ 1.67 (s, 2H), δ 1.51 (s, 2H), δ 1.44 (s, 2H), δ 1.26 (bs, 16H), δ 0.71 (s, 3H) ppm; $^{13}$C NMR (100 MHz, CD$_3$OD) δ 175.6, 159.4, 147.3, 127.6, 108.5, 51.3, 48.6, 38.8, 35.8, 31.9, 29.6, 29.5, 29.4, 29.3, 29.2, 28.2, 28.1, 27.7, 24.8, 24.2, 23.9, 22.6, 22.5, 13.4, 13.3 ppm; HRMS (ESI) calcd for C$_{24}$H$_{43}$N$_7$O (M+) 445.3429. found 445.3524.

N-(2-(4-(5-(2-amino-1H-imidazol-4-yl)pentyl)-1H-1,2,3-triazol-1-yl)ethyl)tetradecanamide hydrochloride tert-butyl 2-amino-4-(hept-6-ynyl)-1H-imidazole-1-carboxylate (0.111 g, 0.401 mmol) was reacted with N-(2-azidoethyl)tetradecanamide (0.130 g, 0.401 mmol) following the general click procedure to give tert-butyl 2-amino-4-(5-(1-(2-tetradecanamidoethyl)-1H-1,2,3-triazol-4-yl)pentyl)-1H-imidazole-1-carboxylate $^1$H NMR (300 MHz, CDCl$_3$) δ 7.26 (s, 1H), δ 6.85 (s, 1H), δ 6.42 (s, 1H), δ 6.05 (s, 1H), δ 4.38 (s, 2H), δ 3.66 (s, 2H), δ 2.60 (s, 2H), δ 2.11 (s, 2H), δ 2.08 (t, J=3.6 Hz, 2H), δ 1.41 (m, 13H), δ 1.32 (s, 2H), δ 1.17 (s, 18H), δ 0.77 (t, J=6.6 Hz, 3H) ppm; $^{13}$C NMR (75 MHz, CDCl$_3$) δ 202.9, 174.3, 149.6, 148.3, 121.9, 100.1, 84.8, 49.5, 42.3, 39.5, 36.7, 32.1, 29.9, 29.8, 29.7, 29.6, 29.5, 29.5, 29.3, 28.9, 28.1, 25.9, 25.6, 22.9, 14.3 ppm; HRMS (ESI) calcd for C$_{31}$H$_{55}$N$_7$O$_3$(M+) 573.4366. found 573.4365, which was subsequently deprotected to give N-(2-(4-(5-(2-amino-1H-imidazol-4-yl)pentyl)-1H-1,2,3-triazol-1-yl)ethyl)tetradecanamide hydrochloride (0.118 g, 87% yield). $^1$H NMR (400 MHz, CD$_3$OD) δ 8.51 (s, 1H), δ 6.53 (s, 1H), δ 4.71 (s, 2H), δ 3.75 (s, 2H), δ 2.89 (s, 2H), δ 2.54 (t, J=6.8 Hz, 2H), δ 2.17 (t, J=6.8 Hz, 2H), δ 1.80 (s, 2H), δ 1.69 (s, 2H), δ 1.54 (s, 2H), δ 1.48 (s, 2H), δ 1.28 (s, 20H), 0.88 (t, J=6.8 Hz, 3H) ppm; $^{13}$C NMR (100 MHz, CD$_3$OD) δ 175.6, 161.8, 147.2, 127.6, 127.4, 108.5, 52.3, 38.8, 36.6, 35.8, 31.9, 30.6, 29.7, 29.6, 29.5, 29.4, 29.2, 28.0, 27.9, 27.7, 25.8, 24.1, 23.6, 23.4, 22.6, 13.4 ppm; HRMS (ESI) calcd for C$_{26}$H$_{47}$N$_7$O (M+) 473.3842. found 473.3834.

N-(2-(4-(5-(2-amino-1H-imidazol-4-yl)pentyl)-1H-1,2,3-triazol-1-yl)ethyl)palmitamide hydrochloride tert-butyl 2-amino-4-(hept-6-ynyl)-1H-imidazole-1-carboxylate (0.087 g, 0.313 mmol) was reacted with N-(2-azidoethyl)palmitamide (0.102 g, 0.313 mmol) following the general click procedure to give tert-butyl 2-amino-4-(5-(1-(2-palmitamidoethyl)-1H-1,2,3-triazol-4-yl)pentyl)-1H-imidazole-1-carboxylate $^1$H NMR (300 MHz, CDCl$_3$) δ 7.29 (s, 1H), δ 6.78 (t, J=4.5 Hz, 1H), δ 6.41 (s, 1H), δ 6.19 (s, 2H), δ 4.39 (t, J=5.4 Hz, 2H), 83.67 (q, J=5.5, 4.8 Hz, 2H), δ 2.61 (t, J=6.9 Hz, 2H), δ 2.12 (t, J=6.5 Hz, 2H), δ 2.07 (t, J=7.5 Hz, 2H), δ 1.42 (m, 13H), δ 1.42 (m, 2H), δ 1.32 (m, 22H), 0.81 (t, J=5.4 Hz, 3H) ppm; $^{13}$C NMR (75 MHz, CDCl$_3$) δ 176.8, 174.3, 173.9, 149.5, 148.3, 121.9, 106.4, 85.0, 67.2, 51.1, 49.5, 39.5, 39.1, 38.1, 36.8, 36.7, 32.1, 29.9, 29.8, 29.7, 29.6, 29.5, 29.3, 28.9, 28.3, 28.2, 27.9, 25.9, 25.6, 22.9, 14.3 ppm; HRMS (ESI) calcd for C$_{33}$H$_{59}$N$_7$O$_3$(M+) 601.4679. found 601.4671, which was subsequently deprotected to give N-(2-(4-(5-(2-amino-1H-imidazol-4-yl)pentyl)-1H-1,2,3-triazol-1-yl)ethyl)palmitamide hydrochloride (0.155 g, 92% yield). $^1$H NMR (300 MHz, CD$_3$OD) δ 8.59 (s, 1H), δ 6.53 (s, 1H), δ 4.72 (s, 2H), δ 3.75 (s, 2H), δ 2.90 (s, 2H), δ 2.54 (s, 2H), δ 2.16 (t, J=7.2 Hz, 2H), δ 1.80 (s, 2H), δ 1.69 (s, 2H), δ 1.51 (s, 4H), δ 1.28 (bs, 24H), δ 0.71 (t, J=6.3 Hz, 3H) ppm; $^{13}$C NMR (75 MHz, CD$_3$OD) δ 175.7, 147.2, 145.6, 128.4, 127.6, 108.6, 67.2, 52.7, 37.4, 36.5, 35.8, 31.9, 29.7, 29.5, 29.4, 29.2, 28.0, 27.9, 27.8, 27.7, 25.8, 24.1, 23.6, 23.2, 22.6 ppm; HRMS (ESI) calcd for C$_{28}$H$_{51}$N$_7$O (M+) 501.4155. found 501.4143.

N-(2-(4-(5-(2-amino-1H-imidazol-4-yl)pentyl)-1H-1,2,3-triazol-1-yl)ethyl)-4,5-dibromo-1-methyl-1H-pyrrole-2-carboxamide hydrochloride tert-butyl 2-amino-4-(hept-6-ynyl)-1H-imidazole-1-carboxylate (0.116 g, 0.417 mmol) was reacted with N-(2-azidoethyl)-4,5-dibromo-1-methyl-1H-pyrrole-2-carboxamide (0.145 g, 0.417 mmol) following the general click procedure to give tert-butyl 2-amino-4-(5-(1-(2-(4,5-dibromo-1-methyl-1H-pyrrole-2-carboxamido)ethyl)-1H-1,2,3-triazol-4-yl)pentyl)-1H-imidazole-1-carboxylate $^1$H NMR (300 MHz, CDCl$_3$) δ 7.76 (s, 1H), δ 7.32 (s, 1H), δ 6.81 (s, 1H), δ 6.49 (s, 1H), δ 6.17 (s, 2H), δ 4.52 (s, 2H), δ 3.94 (s, 3H), δ 3.84 (s, 2H), δ 2.65 (t, J=7.2 Hz, 2H), δ 2.30 (m, 2H), δ 1.58 (m, 13H), δ 1.35 (m, 2H); $^{13}$C NMR (75 MHz, CDCl$_3$) δ 161.2, 149.6, 148.2, 138.8, 127.4, 122.2, 114.9, 111.9, 106.5, 98.2, 84.5, 49.5, 39.7, 35.9, 29.3, 28.9, 28.2, 28.0, 27.7, 25.6 ppm; HRMS (ESI) calcd for C$_{23}$H$_{32}$N$_8$O$_3$ (M+) 626.0964. found 626.0960, which was subsequently deprotected to give N-(2-(4-(5-(2-amino-1H-imidazol-4-yl)pentyl)-1H-1,2,3-triazol-1-yl)ethyl)-4,5-dibromo-1-methyl-1H-pyrrole-2-carboxamide hydrochloride (0.151 g, 64% yield). $^1$H NMR (400 MHz, CD$_3$OD) δ 8.24 (s, 1H), δ 6.86 (s, 1H), δ 6.56 (s, 1H), δ 4.71 (s, 2H), δ 3.81 (s, 5H), 2.78 (s, 2H), δ 2.44 (t, J=7.2 Hz, 2H), δ 1.69 (s, 2H), δ 1.59 (s, 2H), δ 1.37 (s, 2H) ppm; $^{13}$C NMR (100 MHz, CD$_3$OD) δ 161.4, 150.2, 159.8, 159.4, 147.3, 127.6, 127.3, 114.9, 111.6, 108.4, 97.9, 51.3, 39.0, 35.2, 28.3, 28.0, 27.6, 24.2, 23.8 ppm; HRMS (ESI) calcd for C$_{18}$H$_{24}$Br$_2$N$_8$O (M+) 526.0439. found 526.0425.

N-(2-(4-(5-(2-amino-1H-imidazol-4-yl)pentyl)-1H-1,2,3-triazol-1-yl)ethyl)-4-bromo-1H-pyrrole-2-carboxamide hydrochloride tert-butyl 2-amino-4-(hept-6-ynyl)-1H-imidazole-1-carboxylate (0.104 g, 0.375 mmol) was reacted with N-(2-azidoethyl)-4-bromo-1H-pyrrole-2-carboxamide (0.131 g, 0.375 mmol) following the general click procedure to give tert-butyl 2-amino-4-(5-(1-(2-(4-bromo-1H-pyrrole-2-carboxamido)ethyl)-1H-1,2,3-triazol-4-yl)pentyl)-1H-imidazole-1-carboxylate $^1$H NMR (300 MHz, CDCl$_3$) δ 11.44 (s, 1H), δ 7.84 (s, 1H), δ 7.28 (s, 1H), δ 6.84 (s, 1H), δ 6.74 (s, 1H), δ 6.46 (s, 1H), δ 4.89 (s, 2H), δ 3.82 (s, 2H), δ 2.57 (s, 2H), δ 2.28 (s, 2H), δ 1.55 (m, 13H), δ 1.29 (m, 2H) ppm; $^{13}$C NMR (75 MHz, CDCl$_3$) δ 186.8, 161.4, 150.7, 149.3, 148.2, 137.6, 126.3, 122.5, 122.1, 113.1, 100.4, 96.9, 85.4, 49.6, 29.1, 28.7, 28.2, 27.7, 25.5 ppm; HRMS (ESI) calcd for C$_{22}$H$_{31}$BrN$_8$O$_3$(M+) 534.1703. found 534.1705, which was subsequently deprotected to give N-(2-(4-(5-(2-amino-1H-imidazol-4-yl)pentyl)-1H-1,2,3-triazol-1-yl)ethyl)-4-bromo-1H-pyrrole-2-carboxamide hydrochloride (0.129 g, 73% yield). $^1$H NMR (400 MHz, CD$_3$OD) δ 8.42 (s, 1H), δ 6.93 (s, 1H), δ 6.82 (s, 1H), δ 6.47 (s, 1H), δ 4.76 (s, 2H), δ 3.87 (s, 2H), δ 2.79 (s, δ 2.45 (s, 2H), δ 1.69 (s, δ 1.60 (s, 2H), δ 1.37 (s, 2H) ppm; $^{13}$C NMR (100 MHz, CD$_3$OD) δ 161.4, 159.5, 159.1, 147.3, 147.2, 127.6, 125.8, 122.3, 122.1, 112.8, 108.6, 108.5, 96.4, 51.9, 38.9, 28.0, 27.9, 27.6, 24.1, 23.6 ppm; HRMS (ESI) calcd for C$_{17}$H$_{23}$BrN$_8$O (M+) 434.1178. found 434.1171.

N-(2-(4-(5-(2-amino-1H-imidazol-4-yl)pentyl)-1H-1,2,3-triazol-1-yl)ethyl)-1H-pyrrole-2-carboxamide hydrochloride tert-butyl 2-amino-4-(hept-6-ynyl)-1H-imidazole-1-carboxylate (0.097 g, 0.349 mmol) was reacted with N-(2-azidoethyl)-1H-pyrrole-2-carboxamide (0.063 g, 0.349 mmol) following the general click procedure to give tert-butyl 4-(5-(1-(2-(1H-pyrrole-2-carboxamido)ethyl)-1H-1,2,3-triazol-4-yl)pentyl)-2-amino-1H-imidazole-1-carboxylate $^1$H NMR (300 MHz, CDCl$_3$) δ 8.18 (s, 1H), δ 7.36 (d, J=5.7 Hz, 2H), δ 7.24 (s, 1H), δ 6.84 (t, J=8.1 Hz, 1H), δ 6.43 (s, 1H), δ 6.04 (s, 2H), 4.49 (s, 2H), δ 3.89 (s, 2H), δ 2.53 (s, 2H), δ 2.09 (s, 2H), δ 1.44 (m, 13H), δ 1.24 (s, 2H) ppm; $^{13}$C NMR (75 MHz, CDCl$_3$) δ 165.9, 164.8, 164.6, 161.5, 137.5, 122.3, 111.0, 110.7, 107.5, 107.1, 106.8, 85.1, 49.4, 40.5, 29.3, 28.9, 28.2, 25.5 ppm; HRMS (ESI) calcd for C$_{22}$H$_{32}$N$_3$O$_3$ (M+) 456.2597. found 456.2590, which was subsequently deprotected to give N-(2-(4-(5-(2-amino-1H-imidazol-4-yl)pentyl)-1H-1,2,3-triazol-1-yl)ethyl)-1H-pyrrole-2-carboxamide hydrochloride (0.129 g, 94% yield). $^1$H NMR (400 MHz, CD$_3$OD) δ 8.65 (s, 1H), δ 7.41 (s, 2H), δ 7.17 (s, 1H), δ 6.50 (s, 1H), δ 4.74 (s, 2H), δ 3.98 (s, 2H), δ 2.88 (s, 2H), δ 2.49 (s, 2H), δ 1.78 (m, 4H), δ 1.44 (s, 2H) ppm; $^{13}$C NMR (100 MHz, CD$_3$OD) δ 166.3, 164.5, 162.0, 161.9, 137.4, 110.6, 110.3, 110.2, 108.5, 17.1, 106.8, 59.3, 52.4, 39.5, 36.5, 27.9, 27.8, 27.6, 24.1, 23.5, 23.3 ppm; HRMS (ESI) calcd for C$_{17}$H$_{24}$N$_8$O (M+) 356.2073. found 356.2080.

N-(2-(4-(5-(2-amino-1H-imidazol-4-yl)pentyl)-1H-1,2,3-triazol-1-yl)ethyl)-4-tert-butylbenzamide hydrochloride tert-butyl 2-amino-4-(hept-6-ynyl)-1H-imidazole-1-carboxylate (0.070 g, 0.253 mmol) was reacted with N-(2-azidoethyl)-4-tert-butylbenzamide (0.062 g, 0.253 mmol) following the general click procedure to give tert-butyl 2-amino-4-(5-(1-(2-(4-tert-butylbenzamido)ethyl)-1H-1,2,3-triazol-4-yl)pentyl)-1H-imidazole-1-carboxylate $^1$H NMR (300 MHz, CDCl$_3$) δ 7.71 (d, J=7.5 Hz, 2H), δ 7.64 (t, J=5.7 Hz, 1H), δ 7.36 (d, J=7.5 Hz, 2H), δ 7.27 (s, 1H), δ 6.42 (s, 1H), δ 5.99 (s, 2H), δ 4.51 (t, J=5.7 Hz, 2H), δ 3.88 (q, J=5.1, 5.3 Hz, 2H), δ 2.58 (t, J=7.5 Hz, 2H), δ 2.22 (t, J=7.5 Hz, 2H), δ 1.52 (m, 13H), δ 1.21 (m, $^1$H) ppm; $^{13}$C NMR (75 MHz, CDCl$_3$) δ 168.2, 155.3, 150.4, 149.6, 148.3, 138.9, 131.2, 127.3, 125.6, 122.2, 106.5, 84.8, 49.4, 40.2, 35.1, 31.3, 31.1, 29.3, 28.9, 28.3, 28.2, 28.1, 25.6 ppm; HRMS (ESI) calcd for C$_{28}$H$_{41}$N$_7$O$_3$(M+) 523.3271. found 523.3270, which was subsequently deprotected to give N-(2-(4-(5-(2-amino-1H-imidazol-4-yl)pentyl)-1H-1,2,3-triazol-1-yl)ethyl)-4-tert-butylbenzamide hydrochloride (0.105 g, 90% yield). $^1$H NMR (400 MHz, CD$_3$OD) δ 8.48 (s, 1H), δ 7.76 (d, J=6.3 Hz, 2H), δ 7.48 (d, J=6.3 Hz, 2H), δ 6.50 (s, 1H), δ 4.84 (s, 2H), δ 3.95 (s, 2H), δ 2.85 (s, 2H), δ 2.46 (t, J=5.4 Hz, 2H), δ 1.73 (s, 2H), δ 1.57 (m, 2H), δ 1.39 (s, 2H), δ 1.31 (s, 9H) ppm; $^{13}$C NMR (100 MHz, CD$_3$OD) δ 169.2, 155.6, 147.3, 130.8, 129.9, 127.6, 127.2, 127.1, 126.7, 125.4, 125.3, 119.5, 108.6, 108.5, 52.3, 39.4, 34.6, 30.4, 27.9, 27.8, 27.6, 24.1, 23.2, 22.2 ppm; HRMS (ESI) calcd for C$_{23}$H$_{33}$N$_7$O (M+) 423.2747. found 423.2741.

N-(2-(4-(5-(2-amino-1H-imidazol-4-yl)pentyl)-1H-1,2,3-triazol-1-yl)ethyl)-2-naphthamide hydrochloride tert-butyl 2-amino-4-(hept-6-ynyl)-1H-imidazole-1-carboxylate (0.095 g, 0.344 mmol) was reacted with N-(2-azidoethyl)-2-naphthamide (0.083 g, 0.344 mmol) following the general click procedure to give tert-butyl 4-(5-(1-(2-(2-naphthamido)ethyl)-1H-1,2,3-triazol-4-yl)pentyl)-2-amino-1H-imidazole-1-carboxylate $^1$H NMR (300 MHz, CDCl$_3$) δ 8.24 (s, 1H), δ 8.01 (s, 1H), δ 7.72 (m, 4H), δ 7.39 (m, 2H), δ 7.26 (s, 1H), δ 6.33 (s, 1H), S 6.04 (s, 2H), δ 4.51 (s, 2H), δ 3.88 (s, 2H), δ 2.48 (t, 2H), δ 2.12 (s, 2H), δ 1.47 (m, 13H), δ 1.17 (s, 2H) ppm; $^{13}$C NMR (75 MHz, CDCl$_3$) δ 168.5, 150.4, 149.5, 148.3, 138.6, 134.9, 132.7, 131.4, 129.2, 128.5, 128.1, 127.9, 126.8, 124.0, 122.3, 106.5, 84.9, 49.4, 40.4, 29.9, 29.2, 28.9, 28.6, 28.2, 27.9, 28.6, 27.9, 27.8, 25.6 ppm; HRMS (ESI) calcd for C$_{28}$H$_{35}$N$_7$O$_3$(M+) 517.2801. found 517.2792, which was subsequently deprotected to give N-(2-(4-(5-(2-amino-1H-imidazol-4-yl)pentyl)-1H-1,2,3-triazol-1-yl)ethyl)-2-naphthamide hydrochloride (0.140 g, 90% yield). $^1$H NMR (300 MHz, CD$_3$OD) δ ppm; $^{13}$C NMR (75 MHz, CD$_3$OD) δ ppm; HRMS (ESI) calcd for C$_{23}$H$_{27}$N$_7$O (M+) 417.2277. found 417.2274.

N-(2-(4-(5-(2-amino-1H-imidazol-4-yl)pentyl)-1H-1,2,3-triazol-1-yl)ethyl)-2-iodobenzamide hydrochloride tert-butyl 2-amino-4-(hept-6-ynyl)-1H-imidazole-1-carboxylate (0.083 g, 0.299 mmol) was reacted with N-(2-azidoethyl)-2-iodobenzamide (0.095 g, 0.299 mmol) following the general click procedure to give tert-butyl 2-amino-4-(5-(1-(2-(2-iodobenzamido)ethyl)-1H-1,2,3-triazol-4-yl)pentyl)-1H-imidazole-1-carboxylate $^1$H NMR (300 MHz, CDCl$_3$) δ 7.74 (d, J=7.5 Hz, 2H), δ 7.57 (t, J=4.5 Hz, 1H), δ 7.36 (s, 1H), δ 7.22 (s, 2H), δ 6.97 (m, 1H), δ 6.39 (s, 1H), δ 5.97 (s, 2H), δ 4.48 (t, J=5.1 Hz, 2H), δ 3.85 (m, 2H), δ 2.44 (t, J=7.5 Hz, 2H), δ 2.18 (t, J=6.6 Hz, 2H), δ 1.45 (m, 13H), δ 1.18 (m, 2H) ppm; $^{13}$C NMR (75 MHz, CDCl$_3$) δ 170.3, 150.4, 149.5, 148.2, 141.8, 139.9, 138.7, 131.3, 128.4, 128.3, 122.3, 106.5, 92.8, 84.9, 49.2, 40.5, 29.2, 28.9, 28.3, 28.2, 28.0, 25.5 ppm; HRMS (ESI) calcd for C$_{24}$H$_{321}$N$_7$O$_3$ (M+) 593.1611. found 593.1603, which was subsequently deprotected to give N-(2-(4-(5-(2-amino-1H-imidazol-4-yl)pentyl)-1H-1,2,3-triazol-1-yl)ethyl)-2-iodobenzamide hydrochloride (0.125 g, 79% yield). $^1$H NMR (400 MHz, CD$_3$OD) δ 8.35 (s, 1H), δ 7.88 (d, J=7.8 Hz, 1H), δ 7.45 (t, J=6.9 Hz, 1H), δ 7.34 (d, J=6.9 Hz, 1H), δ 7.15 (t, J=7.5 Hz, 1H), δ 6.47 (s, 1H), δ 4.78 (s, 2H), δ 3.99 (s, 2H), δ 2.83 (s, 2H), δ 2.44 (t, J=6.9 Hz, 2H), δ 1.76 (s, 2H), δ 1.64 (s, 2H), δ 1.29 (s, 2H) ppm; $^{13}$C NMR (75 MHz, CD$_3$OD) δ 171.6, 159.2, 147.3, 142.1, 139.8, 131.2, 128.2, 127.7, 124.4, 92.1, 52.2, 40.8, 39.4, 31.2, 28.3, 28.1, 27.7, 24.1, 20.9, 15.9, 10.7 ppm; HRMS (ESI) calcd for C$_{19}$H$_{24}$IN$_7$O (M+) 493.1087. found 493.1085.

N-(2-(4-(5-(2-amino-1H-imidazol-4-yl)pentyl)-1H-1,2,3-triazol-1-yl)ethyl)-4-heptylbenzamide hydrochloride tert-butyl 2-amino-4-(hept-6-ynyl)-1H-imidazole-1-carboxylate (0.125 g, 0.449 mmol) was reacted with N-(2-azidoethyl)-4-heptylbenzamide (0.129 g, 0.449 mmol) following the general click procedure to give tert-butyl 2-amino-4-(5-(1-(2-(4-heptylbenzamido)ethyl)-1H-1,2,3-triazol-4-yl)pentyl)-1H-imidazole-1-carboxylate $^1$H NMR (400 MHz, CDCl$_3$) δ 7.78 (s, 1H), δ 7.65 (d, 2H), δ 7.27 (s, 1H), δ 7.09 (d, 2H), δ 6.39 (s, 1H), δ 6.22 (s, 2H), δ 4.47 (s, 2H), δ 3.81 (s, 2H), δ 3.96 (s, 4H), δ 2.20 (s, 2H), δ 2.05 (s, 2H), 1.48 (m, 12H), δ 1.17 (m, 8H), δ 0.77 (t, J=6.4 Hz, 3H); $^{13}$C NMR (100 MHz, CDCl$_3$) δ 168.3, 149.6, 148.2, 147.1, 138.6, 131.5, 128.6, 127.4, 122.1, 106.4, 84.8, 67.1, 49.4, 40.2, 37.9, 36.9, 31.9, 31.3, 31.1, 29.8, 28.4, 29.3, 28.9, 28.3, 28.1, 28.0, 25.5, 22.8, 14.3 ppm; HRMS (ESI) calcd for C$_{31}$H$_{47}$N$_7$O$_3$ (M+) 565.3704. found 656.3737, which was subsequently deprotected to give N-(2-(4-(5-(2-amino-1H-imidazol-4-yl)pentyl)-1H-1,2,3-triazol-1-yl)ethyl)-4-heptylbenzamide hydrochloride (0.194 g, 86% yield). $^1$H NMR (300 MHz, CD$_3$OD) δ 8.25 (s, 1H), δ 7.71 (d, J=5.4 Hz, 2H), δ 7.24 (d, J=5.7 Hz, 2H), δ 6.45 (s, 1H), δ 4.74 (s, 2H), 3.90 (s, 2H), δ 2.63 (s, 2H), δ 2.61 (t, 2H), δ 2.41 (s, 2H), δ 1.58 (m, 6H), δ 1.26 (m, 10H), δ 0.85 (t, J=4.8 Hz, 3H) ppm; $^{13}$C NMR (100 MHz, CD$_3$OD) δ 169.2, 150.2, 147.4, 131.2, 128.5, 127.6, 127.3, 108.4, 51.4, 39.6, 36.5, 35.6, 31.8, 331.3, 29.1, 29.1, 28.3, 28.0, 27.7, 24.1, 22.6, 13.4, 13.3 ppm; HRMS (ESI) calcd for C$_{26}$H$_{39}$N$_7$O (M+) 465.3216. found 465.3207.

N-(2-(4-(5-(2-amino-1H-imidazol-4-yl)pentyl)-1H-1,2,3-triazol-1-yl)ethyl)-4-hexylbenzamide hydrochloride tert-butyl 2-amino-4-(hept-6-ynyl)-1H-imidazole-1-carboxylate (0.097 g, 0,349 mmol) was reacted with N-(2-azidoethyl)-4-hexylbenzamide (0.096 g, 0.349 mmol) following the general click procedure to give tert-butyl 2-amino-4-(5-(1-(2-(4-hexylbenzamido)ethyl)-1H-1,2,3-triazol-4-yl)pentyl)-1H-imidazole-1-carboxylate $^1$H NMR (300 MHz, CDCl$_3$) δ 7.65 (d, J=8.1 Hz, 2H), δ 7.55 (t, J=6.7 Hz, 1H), δ 7.26 (s, 1H), δ 7.09 (d, J=7.8 Hz, 2H), δ 6.39 (s, 1H), δ 6.04 (s, 2H), δ 4.48 (t, J=4.8 Hz, 2H), δ 3.83 (q, J=5.6, 4.8 Hz, 2H), δ 2.56 (q, J=7.5, 8.1 Hz, 4H), δ 2.24 (t, J=6.9 Hz, 2H), δ 1.50 (m, 13H), δ 1.21 (m, 1H), δ 0.77 (t, J=5.7 Hz, 3H) ppm; $^{13}$C NMR (75 MHz, CDCl$_3$) δ 168.3, 148.3, 147.3, 138.7, 131.4, 128.7, 127.4, 122.2, 106.4, 84.9, 73.9, 49.5, 40.2, 36.0, 31.8, 31.3, 29.9, 29.3, 29.1, 28.9, 28.2, 28.1, 28.0, 25.6, 22.8, 14.3 ppm; HRMS (ESI) calcd for C$_{30}$H$_{45}$N$_7$O$_3$ (M+) 551.3584. found 551.3581, which was subsequently deprotected to give N-(2-(4-(5-(2-amino-1H-imidazol-4-yl)pentyl)-1H-1,2,3-triazol-1-yl)ethyl)-4-hexylbenzamide hydrochloride (0.164 g, 96% yield). $^1$H NMR (400 MHz, CD$_3$OD) δ 8.28 (s, 1H), δ 7.67 (d, J=7.6 Hz, 2H), δ 7.21 (d, J=7.6 Hz, 2H), δ 6.43 (s, 1H), δ 4.72 (s, 2H), δ 3.87 (s, 2H), δ 2.74 (s, 2H), δ 2.58 (t, J=7.6 Hz, 2H), δ 2.31 (t, J=6.8 Hz, 2H), δ 1.66 (s, 2H), δ 1.55 (s, 4H), δ 1.35 (s, 2H), δ 1.25 (s, 6H), δ 0.66 (t, J=8.8 Hz, 3H) ppm; $^{13}$C NMR (100 MHz, CD$_3$OD) δ 169.2, 159.5, 147.4, 147.3, 131.2, 108.4, 51.2, 48.5, 48.3, 48.1, 47.9, 47.7, 47.5, 47.3, 39.5, 36.5, 35.6, 31.6, 31.7, 31.2, 28.8, 28.2, 27.9, 27.7, 24.1, 23.9, 22.6, 13.3, 9.9 ppm; HRMS (ESI) calcd for C$_{25}$H$_{37}$N$_7$O (M+) 451.3059. found 451.3058.

N-(2-(4-(5-(2-amino-1H-imidazol-4-yl)pentyl)-1H-1,2,3-triazol-1-yl)ethyl)-4-butylbenzamide hydrochloride tert-butyl 2-amino-4-(hept-6-ynyl)-1H-imidazole-1-carboxylate (0.123 g, 0.443 mmol) was reacted with N-(2-azidoethyl)-4-butylbenzamide (0.109 g, 0.443 mmol) following the general click procedure to give tert-butyl 2-amino-4-(5-(1-(2-(4-butylbenzamido)ethyl)-1H-1,2,3-triazol-4-yl)pentyl)-1H-imidazole-1-carboxylate $^1$H NMR (300 MHz, CDCl$_3$) δ 7.67 (s, 1H), δ 7.67 (d, J=7.5 Hz, 2H), δ 7.29 (s, 1H), δ 7.11 (d, J=7.5 Hz, 2H), δ 6.42 (s, 1H), δ 6.25 (s, 2H), δ 4.48 (s, 2H), δ 3.83 (s, 2H), δ 2.56 (t, J=7.2 Hz, 4H), δ 2.21 (s, 2H), 1.47 (m, 13H), δ 1.21 (m, 4H), δ 0.83 (t, J=7.2 Hz, 3H) ppm; $^{13}$C NMR (75 MHz, CDCl$_3$) δ168.3, 140.6, 149.5, 148.2, 147.1, 138.4, 131.5, 128.7, 127.4, 122.2, 106.4, 84.9, 49.4, 40.2, 35.7, 33.5, 29.2, 28.9, 28.3, 28.1, 27.9, 25.5, 22.4, 14.1 ppm; HRMS (ESI) calcd for C$_{28}$H$_{41}$N$_7$O$_3$ (M+) 523.3271. found 523.3261, which was subsequently deprotected to give N-(2-(4-(5-(2-amino-1H-imidazol-4-yl)pentyl)-1H-1,2,3-triazol-1-yl)ethyl)-4-butylbenzamide hydrochloride (0.191 g, 94% yield). $^1$H NMR (300 MHz, CD$_3$OD) δ 8.43 (s, 1H), δ 7.69 (s, 2H), δ 7.22 (s, 2H), δ 6.44 (s, 1H), δ 4.73 (s, 2H), δ 3.89 (s, 2H), δ 3.34 (s, 2H), δ 2.59 (s, 4H), δ 2.41 (s, 2H), δ 1.54 (s, 4H), δ 1.29 (s, 4H), δ 0.88 (t, J=6.9 Hz, 3H) ppm; $^{13}$C NMR (75 MHz, CD$_3$OD) δ 169.2, 165.1, 160.3, 158.1, 147.4, 141.4, 131.2, 128.5, 127.7, 127.3, 126.9, 92.9, 39.6, 36.3, 33.4, 30.9, 28.0, 27.7, 24.1, 22.2, 13.2, 12.1, 10.9, 8.9, 6.2, 2.5 ppm; HRMS (ESI) calcd for $C_{23}H_{33}N_7O$ (M+) 423.2747. found 423.2738.

N-(2-(4-(5-(2-amino-1H-imidazol-4-yl)pentyl)-1H-1,2,3-triazol-1-yl)ethyl)-4-pentylbenzamide hydrochloride tert-butyl 2-amino-4-(hept-6-ynyl)-1H-imidazole-1-carboxylate (0.113 g, 0.408 mmol) was reacted with N-(2-(4-(5-(2-amino-1H-imidazol-4-yl)pentyl)-1H-1,2,3-triazol-1-yl)ethyl)biphenyl-4-carboxamide hydrochloride (0.106 g, 0.408 mmol) following the general click procedure to give tert-butyl 2-amino-4-(5-(1-(2-(4-pentylbenzamido)ethyl)-1H-1,2,3-triazol-4-yl)pentyl)-1H-imidazole-1-carboxylate $^1$H NMR (300 MHz, CDCl$_3$) δ 7.75 (s, 1H), δ 7.67 (d, J=7.5 Hz, 2H), δ 7.27 (s, 1H), δ 7.12 (d, J=7.8 Hz, 2H), δ 4.48 (s, 2H), δ 3.84 (s, 2H), δ 2.55 (m, 4H), δ 2.22 (s, 2H), δ 1.50 (s, 13H), δ 1.23 (s, 8H), δ 0.80 (t, J=5.7 Hz, 3H); $^{13}$C NMR (75 MHz, CDCl$_3$) δ ppm 168.3, 150.5, 149.5, 148.2, 147.2, 138.6, 131.5, 128.7, 127.4, 106.4, 84.8, 49.4, 40.2, 35.9, 31.6, 31.0, 29.3, 28.9, 28.1, 27.9, 25.6, 22.6, 14.2; HRMS (ESI) calcd for $C_{29}H_{43}N_7O_3$ (M+) 537.3427. found 537.3420, which was subsequently deprotected to give N-(2-(4-(5-(2-amino-1H-imidazol-4-yl)pentyl)-1H-1,2,3-triazol-1-yl)ethyl)-4-pentylbenzamide hydrochloride (0.178 g, 92% yield). $^1$H NMR (300 MHz, CD$_3$OD) δ 8.41 (s, 1H), δ 7.69 (d, J=7.5 Hz, 2H), δ 7.21 (d, J=7.2 Hz, 2H), δ 6.46 (s, 1H), δ 4.84 (s, 2H), δ 3.90 (s, 2H), δ 2.79 (s, 2H), δ 2.58 (t, J=7.8 Hz, 2H), δ 2.39 (t, J=7.2 Hz, 2H), δ 1.68 (s, 2H), δ 1.55 (s, 4H), δ 1.26 (s, 6H), δ 0.84 (t, J=6.6 Hz, 3H) ppm; $^{13}$C NMR (75 MHz, CD$_3$OD) δ 169.2, 159.5, 158.9, 147.5, 147.3, 131.1, 128.5, 127.6, 127.4, 108.5, 54.2, 51.9, 39.5, 35.6, 31.4, 30.9, 30.6, 28.4, 27.9, 27.6, 26.9, 24.1, 23.5, 22.9, 22.4, 13.3 ppm; HRMS (ESI) calcd for $C_{24}H_{35}N_7O$ (M+) 437.2903. found 437.2892.

N-(2-(4-(5-(2-amino-1H-imidazol-4-yl)pentyl)-1H-1,2,3-triazol-1-yl)ethyl)-2,4,6-trichlorobenzamide hydrochloride tert-butyl 2-amino-4-(hept-6-ynyl)-1H-imidazole-1-carboxylate (0.088 g, 0.318 mmol) was reacted with N-(2-azidoethyl)-2,4,6-trichlorobenzamide (0.093 g, 0.318 mmol) following the general click procedure to give tert-butyl 2-amino-4-(5-(1-(2-(2,4,6-trichlorobenzamido)ethyl)-1H-1,2,3-triazol-4-yl)pentyl)-1H-imidazole-1-carboxylate $^1$H NMR (300 MHz, CDCl$_3$) δ 8.22 (s, 1H), δ 7.34 (s, 1H), δ 7.26 (s, 2H), δ 6.42 (s, 1H), δ 5.97 (s, 2H), δ 4.51 (s, 2H), δ 3.94 (s, 2H), δ 2.45 (t, 2H), δ 2.20 (s, 2H), δ 1.47 (m 13H), δ 1.21 (m, 2H) ppm; $^{13}$C NMR (75 MHz, CDCl$_3$) δ 164.7, 148.0, 135.7, 134.6, 132.9, 128.7, 128.1, 127.3, 122.3, 84.9, 53.7, 49.3, 39.9, 31.8, 29.2, 28.9, 28.2, 25.5, 22.8, 14.3; HRMS (ESI) calcd for $C_{24}H_{30}Cl_3N_7O_3$ (M+) 569.1476. found 569.1477, which was subsequently deprotected to give N-(2-(4-(5-(2-amino-1H-imidazol-4-yl)pentyl)-1H-1,2,3-triazol-1-yl)ethyl)-2,4,6-trichlorobenzamide hydrochloride (0.116 g, 72% yield). $^1$H NMR (300 MHz, CD$_3$OD) δ 8.36 (s, 1H), δ 7.45 (s, 2H), δ 6.46 (s, 1H), δ 4.77 (s, 2H), δ 3.97 (s, 2H), δ 2.80 (s, 2H), δ 2.48 (t, J=6.9 Hz, 2H), δ 1.73 (s, 2H), δ 1.62 (s, 2H), δ 1.41 (s, 2H) ppm; $^{13}$C NMR (75 MHz, CD$_3$OD) δ 165.5, 147.3, 136.9, 134.5, 132.7, 128.2, 128.0, 127.6, 108.6, 51.2, 39.0, 28.1, 27.7, 24.1, 23.8 ppm; HRMS (ESI) calcd for $C_{19}H_{22}Cl_3N_7O$ (M+) 469.0951. found 469.0941.

N-(2-(4-(5-(2-amino-1H-imidazol-4-yl)pentyl)-1H-1,2,3-triazol-1-yl)ethyl)-3,5-difluorobenzamide hydrochloride tert-butyl 2-amino-4-(hept-6-ynyl)-1H-imidazole-1-carboxylate (0.123 g, 0.442 mmol) was reacted with N-(2-azidoethyl)-3,5-difluorobenzamide (0.100 g, 0.442 mmol) following the general click procedure to give tert-butyl 2-amino-4-(5-(1-(2-(3,5-difluorobenzamido)ethyl)-1H-1,2,3-triazol-4-yl)pentyl)-1H-imidazole-1-carboxylate $^1$H NMR (300 MHz, CDCl$_3$) δ 8.25 (s, 1H), δ 7.39 (m, 3H), δ 6.88 (t, J=4.8 Hz, 1H), δ 6.43 (s, 1H), δ 6.38 (bs, 2H), δ 4.55 (s, 2H), δ 3.93 (s, 2H), δ 2.56 (t, J=5.1 Hz, 2H), δ 2.24 (s, 2H), δ 1.55 (m, 14H), δ 1.23 (s, 2H) ppm; $^{13}$C NMR (75 MHz, CDCl$_3$) δ 165.9, 164.3, 164.2, 161.9, 150.3, 149.3, 148.2, 137.6, 122.4, 111.0, 110.8, 107.3, 107.1, 106.8, 106.6, 85.5, 49.3, 40.4, 29.9, 29.5, 29.1, 28.7, 28.2, 27.9, 27.5, 25.4 ppm; HRMS (ESI) calcd for $C_{24}H_{31}F_2N_7O_3$ (M+) 503.2456. found 503.2458, which was subsequently deprotected to give N-(2-(4-(5-(2-amino-1H-imidazol-4-yl)pentyl)-1H-1,2,3-triazol-1-yl)ethyl)-3,5-difluorobenzamide hydrochloride (0.115 g, 59% yield). $^1$H NMR (400 MHz, CD$_3$OD) δ 8.55 (s, 1H), δ 7.42 (d, J=2.0 Hz, 2H), δ 7.29 (t, J=2.40 Hz, 1H), δ 6.51 (s, 1H), δ 4.84 (t, J=4.8 Hz, 2H), δ 3.96 (q, J=13.2, 4.8 Hz, 2H), δ 2.89 (t, J=7.2 Hz, 2H), δ 2.49 (t, J=7.2 Hz, 2H), δ 1.79 (m, 2H), δ 1.75 (m, 2H), δ 1.44 (m, 2H) ppm; $^{13}$C NMR (100 MHz, CD$_3$OD) δ 164.5, 164.4, 127.6, 126.9, 110.6, 110.6, 110.3, 108.5, 107.1, 106.8, 106.6, 52.5, 39.5, 30.4, 27.9, 27.8, 27.6, 24.0, 23.8, 23.1 ppm; FIRMS (ESI) calcd for $C_{19}H_{23}F_2N_7O$ (M+) 403.1932. found 403.1926.

N-(2-(4-(5-(2-amino-1H-imidazol-4-yl)pentyl)-1H-1,2,3-triazol-1-yl)ethyl)biphenyl-4-carboxamide hydrochloride tert-butyl 2-amino-4-(hept-6-ynyl)-1H-imidazole-1-carboxylate (0.093 g, 0.334 mmol) was reacted with N-(2-azidoethyl)biphenyl-4-carboxamide (0.089 g, 0.334 mmol) following the general click procedure to give tert-butyl 2-amino-4-(5-(1-(2-biphenyl-4-ylcarboxamidoethyl)-1H-1,2,3-triazol-4-yl)pentyl)-1H-imidazole-1-carboxylate $^1$H NMR (300 MHz, CDCl$_3$) δ 7.91 (d, J=5.1 Hz, 3H), δ 7.57 (t, J=8.4 Hz, 4H), δ 7.44 (t, J=6.9 Hz, 3H), δ 7.34 (1H), δ 4.60 (t, J=5.1 Hz, 2H), δ 3.96 (q, J=5.1, 5.4 Hz, 2H), δ 2.63 (t, J=7.2 Hz, 2H), δ 2.27 (t, J=7.5 Hz, 2H), δ 1.62 (m, 13H), δ 1.33 (m, 2H) ppm; $^{13}$C NMR (75 MHz, CDCl$_3$) δ 168.0, 149.6, 148.3, 144.6, 140.1, 138.8, 132.8, 129.1, 128.2, 128.0, 127.4, 127.3, 122.2, 84.9, 49.4, 40.3, 29.3, 28.9, 28.3, 28.2, 28.1, 25.6 ppm; FIRMS (ESI) calcd for $C_{30}H_{37}N_7O_3$ (M+) 543.2958. found 543.2949, which was subsequently deprotected to give N-(2-(4-(5-(2-amino-1H-imidazol-4-yl)pentyl)-1H-1,2,3-triazol-1-yl)ethyl)biphenyl-4-carboxamide hydrochloride (0.093 g, 58% yield). $^1$H NMR (300 MHz, CD$_3$OD) δ 8.35 (s, 1H), δ 7.88 (d, J=8.1 Hz, 2H), δ 7.65 (d, J=8.4 Hz, 2H), δ 7.57 (d, J=7.5 Hz, 2H), δ 7.39 (t, J=7.5 Hz, 2H), δ 7.34 (t, J=7.2 Hz, 1H), δ 6.39 (s, 1H), δ 4.81 (s, 2H), δ 3.96 (s, 2H), δ 2.78 (s, 2H), δ 2.37 (t, J=7.5 Hz, 2H), δ 1.67 (s, 2H), δ 1.56 (t, 2H), δ 1.33 (s, 2H) ppm; $^{13}$C NMR (75 MHz, CD$_3$OD) δ 203.6, 158.9, 160.1, 159.5, 159.1, 159.0, 158.5, 149.8, 147.2, 144.6, 132.4, 128.9, 127.9, 127.6, 126.9, 126.4, 108.4, 51.7, 39.5, 27.9, 27.6, 24.0, 23.5, 7.2 ppm; HRMS (ESI) calcd for $C_{25}H_{29}N_7O$ (M+) 443.2434. found 443.2423.

N-(2-(4-(5-(2-amino-1H-imidazol-4-yl)pentyl)-1H-1,2,3-triazol-1-yl)ethyl)-4-octylbenzamide hydrochloride tert-butyl 2-amino-4-(hept-6-ynyl)-1H-imidazole-1-carboxylate (0.078 g, 0.282 mmol) was reacted with N-(2-azidoethyl)-4-octylbenzamide (0.085 g, 0.282 mmol) following the general click procedure to give tert-butyl 2-amino-4-(5-(1-(2-(4-octylbenzamido)ethyl)-1H-1,2,3-triazol-4-yl)pentyl)-1H-imidazole-1-carboxylate $^1$H NMR (300 MHz, CDCl$_3$) δ 7.64 (s, 2H), δ 7.47 (s, 1H), δ 7.21 (s, 1H), δ 7.09 (s, 2H), δ 6.47 (bs, 3H), δ 4.48 (s, 2H), δ 3.84 (s, 2H), δ 2.53 (s, 4H), δ 2.28 (t, J=15.9 Hz, 2H), δ 1.51 (bs, 6H), δ 1.18 (bs, 10H), 0.77 (t, J=6.6 Hz, 3H) ppm; $^{13}$C NMR (75 MHz, CDCl$_3$) δ 180.7, 180.2, 168.3, 147.4, 142.4, 139.2, 131.4, 128.8, 127.4, 107.4, 49.6, 40.2, 36.1, 32.1, 31.4, 29.9, 29.6, 29.5, 28.8, 28.2, 28.1, 25.4, 22.9, 14.3 ppm; HRMS (ESI) calcd for C$_{32}$H$_{49}$N$_7$O$_3$ (M+) 579.3896. found 579.3890, which was subsequently deprotected to give N-(2-(4-(5-(2-amino-1H-imidazol-4-yl)pentyl)-1H-1,2,3-triazol-1-yl) ethyl)-4-octylbenzamide hydrochloride (0.097 g, 67% yield). $^1$H NMR (400 MHz, CD$_3$OD) δ 7.65 (s, 2H), δ 7.23 (s, 3H), δ 6.45 (s, 1H), δ 3.97 (s, 4H), δ 2.60 (s, 4H), δ 2.47 (s, 2H), δ 1.57 (m, 6H), δ 1.27 (bm, 12H), δ 0.83 (t, J=6.4 Hz, 3H) ppm; $^{13}$C NMR (100 MHz, CD$_3$OD) δ 183.5, 172.0, 169.3, 161.8, 153.9, 147.4, 131.2, 128.5, 127.7, 127.3, 119.1, 108.8, 104.7, 94.6, 63.4, 38.7, 35.6, 31.8, 31.3, 29.3, 29.2, 29.1, 28.1, 27.7, 27.1, 24.2, 22.5, 13.3, 12.6 ppm; HRMS (ESI) calcd for C$_{27}$H$_{41}$N$_7$O (M+) 479.3372. found 479.3378.

N-(2-(4-(5-(2-amino-1H-imidazol-4-yl)pentyl)-1H-1,2,3-triazol-1-yl)ethyl)-4-nonylbenzamide hydrochloride tert-butyl 2-amino-4-(hept-6-ynyl)-1H-imidazole-1-carboxylate (g, mmol) was reacted with (g, mmol) following the general click procedure to give tert-butyl 2-amino-4-(5-(1-(2-(4-nonylbenzamido)ethyl)-1H-1,2,3-triazol-4-yl)pentyl)-1H-imidazole-1-carboxylate $^1$H NMR (300 MHz, CDCl$_3$) δ 7.70 (d, J=7.2 Hz, 2H), δ 7.29 (s, 1H), δ 7.27 (t, J=8.7 Hz, 1H), δ 7.16 (d, J=7.2 Hz, 2H), δ 4.53 (s, 2H), δ 3.91 (s, 2H), δ 2.61 (m, 4H), δ 2.41 (m, 1H), δ 2.14 (s, 1H), δ 1.56 (bs, 15H), δ 1.23 (bs, 14H), δ 0.83 (t, J=6.6 Hz, 3H) ppm; $^{13}$C NMR (75 MHz, CDCl$_3$) δ 188.1, 169.7, 168.3, 164.4, 148.0, 147.4, 131.4, 128.8, 127.4, 122.2, 51.6, 49.5, 40.2, 36.0, 32.1, 31.4, 29.7, 29.6, 29.5, 29.4, 29.3, 28.2, 25.6, 22.9, 14.3 μm; HRMS (ESI) calcd for C$_{33}$H$_{51}$N$_7$O$_3$ (M+) 593.4053. found 593.4049, which was subsequently deprotected to give N-(2-(4-(5-(2-amino-1H-imidazol-4-yl)pentyl)-1H-1,2,3-triazol-1-yl)ethyl)-4-nonylbenzamide hydrochloride (0.183 g, 74% yield). $^1$H NMR (400 MHz, CD$_3$OD) δ 8.66 (s, 1H), δ 7.69 (s, 2H), δ 7.25 (s, 2H), δ 6.54 (s, 1H), δ 4.81 (s, 2H), δ 3.62 (s, 2H), δ 2.85 (s, 2H), δ 2.63 (s, 2H), δ 2.46 (s, 2H), δ 1.75 (s, 2H), δ 1.39 (s, 4H), δ 1.29 (m, 14H), δ 0.88 (s, 3H) ppm; $^{13}$C NMR (100 MHz, CD$_3$OD) δ 205.0, 169.2, 147.5, 147.3, 131.2, 128.5, 127.3, 108.9, 108.6, 96.0, 52.4, 51.6, 39.3, 38.9, 35.6, 31.9, 31.3, 30.6, 29.5, 29.4, 29.3, 29.2, 28.1, 27.9, 27.7, 24.1, 23.6, 22.6, 13.4 ppm; HRMS (ESI) calcd for C$_{28}$H$_{43}$N$_7$O (M+) 493.3529. found 493.3522.

N-(2-(4-(5-(2-amino-1H-imidazol-4-yl)pentyl)-1H-1,2,3-triazol-1-yl)ethyl)-2',4'-difluoro-3-hydroxybiphenyl-4-carboxamide hydrochloride tert-butyl 2-amino-4-(hept-6-ynyl)-1H-imidazole-1-carboxylate (0.085 g, 0.306 mmol) was reacted with N-(2-azidoethyl)-2',4'-difluoro-3-hydroxybiphenyl-4-carboxamide (0.097 g, 0.306 mmol) following the general click procedure to give tert-butyl 2-amino-4-(5-(1-(2-(2',4'-difluoro-3-hydroxybiphenyl-4-ylcarboxamido)ethyl)-1H-1,2,3-triazol-4-yl)pentyl)-1H-imidazole-1-carboxylate $^1$H NMR (300 MHz, CDCl$_3$) δ 8.54 (S, 1H), δ 7.83 (s, 1H), δ 7.37 (d, J=7.2 Hz, 1H), δ 7.28 (s, 1H), δ 7.18 (s, 1H), δ 6.89 (d, J=7.8 Hz, 1H), δ 6.72 (s, 2H), δ 6.39 (s, 1H), δ 4.57 (s, 2H), δ 3.81 (s, 2H), δ 3.34 (s, 1H), δ 2.47 (s, 2H), δ 2.07 (s, 2H), δ 1.49 (m, 13H), δ 1.17 (s, 2H) ppm; $^{13}$C NMR (75 MHz, CDCl$_3$) δ 169.5, 163.7, 161.3, 160.5, 159.9, 150.5, 149.2, 148.2, 137.1, 136.3, 134.5, 131.4, 12.8, 126.8, 124.4, 122.3, 117.9, 116.1, 111.9, 111.6, 106.7, 104.8, 104.4, 104.1, 85.8, 50.5, 49.4, 46.6, 50.0, 37.9, 29.9, 28.9, 28.5, 28.3, 28.1, 27.4, 25.3, 25.0 ppm; HRMS (ESI) calcd for C$_{30}$H$_{35}$F$_2$N$_4$O$_4$(M+) 595.2729. found 595.2717, which was subsequently deprotected to give (0.137 g, 84% yield). $^1$H NMR (400 MHz, CD$_3$OD) δ 8.60 (s, 1H), δ 7.89 (s, 1H), δ 7.52 (s, 2H), δ 6.97 (t, J=6.3 Hz, 3H), δ 6.45 (s, 1H), δ 4.81 (s, 2H), δ 2.78 (s, 2H), δ 2.42 (s, 2H), δ 1.72 (s, 2H), δ 1.61 (d, J=7.8 Hz, 2H), δ 1.38 (s, 2H) ppm; $^{13}$C NMR (100 MHz, CD$_3$OD) δ 172.9, 169.8, 161.6, 159.5, 147.2, 134.4, 131.7, 128.4, 127.6, 126.0, 117.5, 115.6, 111.7, 111.5, 108.5, 104.2, 104.0, 103.7, 94.6, 51.9, 39.0, 27.9, 27.6, 26.8, 24.1, 23.8 ppm; HRMS (ESI) calcd for C$_{25}$H$_{27}$F$_2$N$_7$O$_2$ (M+) 459.2194. found 459.2190.

Procedure to Determine the Inhibitory Effect of Test Compounds on C. albicans, C. neoformans and a Mixed S. epidermidis/C. albicans Biofilm Formation:

Inhibition assays were performed by taking an overnight culture of yeast or yeast/bacteria strain and subculturing it at an OD$_{600}$ of 0.05 into YPD (Yeast extract, peptone and dextrose (BD 242820)) media for the yeast alone or tryptic soy broth for the S. epidermidis/C. albicans. Stock solutions of predetermined concentrations of the test compound were then made in the necessary media. These stock solutions were aliquoted (100 μL) into the wells of the 96-well PVC microtiter plate. Sample plates were then wrapped in GLAD Press n' Seal® followed by an incubation under stationary conditions for 24 h at 37° C. After incubation, the media was discarded from the wells and the plates were washed thoroughly with water. Plates were then stained with 100 μL of 0.1% solution of crystal violet (CV) and then incubated at ambient temperature for 30 min. Plates were washed with water again and the remaining stain was solubilized with 200 μL of 95% ethanol. A sample of 125 μL of solubilized CV stain from each well was transferred to the corresponding wells of a polystyrene microtiter dish. Biofilm inhibition was quantitated by measuring the OD$_{540}$ of each well in which a negative control lane wherein no biofilm was formed served as a background and was subtracted out.

Procedure to Determine the Dispersal Effect of Test Compounds on C. albicans and C. neoformans Preformed Biofilms:

Dispersion assays were performed by taking an overnight culture of bacterial strain and subculturing it at an OD$_{600}$ of 0.01 into Yeast extract, peptone and dextrose (BD 242820) media. The resulting bacterial suspension was aliquoted (100 μL) into the wells of a 96-well PVC microtiter plate. Plates were then wrapped in GLAD Press n' Seal® followed by an incubation under stationary conditions at ambient temperature to establish the biofilms. After 24 h, the media was discarded from the wells and the plates were washed thoroughly with water. Stock solutions of predetermined concentrations of the test compound were then made in the necessary media. These stock solutions were aliquoted (100 μL) into the wells of the 96-well PVC microtiter plate with the established biofilms. Media alone was added to a subset of the wells to serve as a control. Sample Plates were then incubated for 24 h at 37° C. After incubation, the media was discarded from the wells and the plates were washed thoroughly with water. Plates were then stained with 100 μL of 0.1% solution of crystal violet (CV) and then incubated at ambient temperature for 30 min. Plates were washed with water again and the remaining stain was solubilized with 200 μL, of 95% ethanol. A sample of 125 μL of solubilized CV stain from each well was transferred to the corresponding wells of a polystyrene microtiter dish. Biofilm dispersion was quantitated by measuring the $OD_{540}$ of each well in which a negative control lane wherein no biofilm was formed served as a background and was subtracted out.

The foregoing is illustrative of the present invention, and is not to be construed as limiting thereof. The invention is defined by the following claims, with equivalents of the claims to be included therein.

That which is claimed is:

1. An agricultural composition comprising:
   (a) an agriculturally acceptable carrier; and
   (b) an antimicrobial or biofilm removing or inhibiting compound of Formula (II)(a):

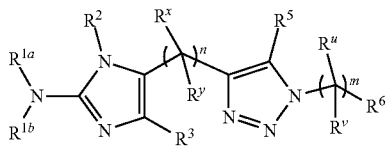

(II)(a)

wherein:
   $R^{1a}$ and $R^{1b}$ are each H;
   $R^2$, $R^3$ and $R^5$ are each independently H or alkyl;
   each occurrence of $R^x$, $R^y$, $R^u$ and $R^v$ is present or absent (depending upon chain saturation), and are each independently H or alkyl;
   $R^6$ is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, nitro, carboxy, amino acid sidechain, amino acid and peptide,
   wherein $R^6$ is optionally substituted with one, two, three or four substituents independently selected from the group consisting of: halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
   n=0 to 10; and
   m=0 to 20;
   or an agriculturally acceptable salt thereof,
   wherein said composition further comprises a microbicide, a bacteriophage or a plant defense activator.

2. The composition of claim 1, wherein said composition comprises a microbicide.

3. The composition of claim 2, wherein said microbicide comprises copper.

4. The composition of claim 1, further comprising an antibiotic.

5. The composition of claim 1, wherein said composition comprises a bacteriophage.

6. The composition of claim 1, wherein said composition comprises a plant defense activator.

7. The composition of claim 1, wherein said carrier is an aqueous carrier or a solid particulate carrier.

8. The composition of claim 1, wherein said compound of Formula (II)(a) is a compound of Formula (II)(a)(5)(D):

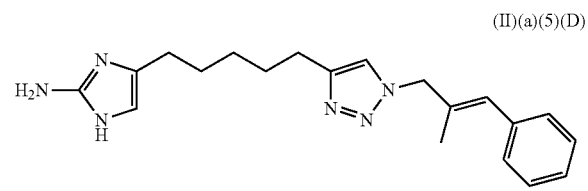 [SMILES: C/C(=C\c1ccccc1)Cn1cc(CCCCCc2c[nH]c(N)n2)nn1]

(II)(a)(5)(D)

or an agriculturally acceptable salt thereof.

9. A method of removing or inhibiting microbial biofilm formation or microbial infection in a plant or plant part thereof, comprising applying to said plant or plant part a treatment effective amount of a compound of Formula (II)(a):

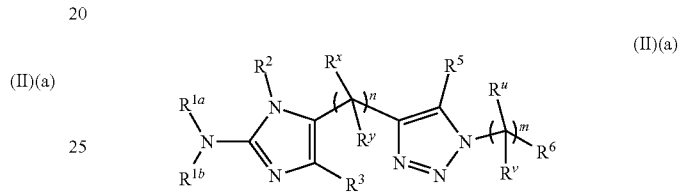

(II)(a)

wherein:
   $R^{1a}$ and $R^{1b}$ are each H;
   $R^2$, $R^3$ and $R^5$ are each independently H or alkyl;
   each occurrence of $R^x$, $R^y$, $R^u$ and $R^v$ is present or absent (depending upon chain saturation), and are each independently H or alkyl;
   $R^6$ is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, nitro, carboxy, amino acid sidechain, amino acid and peptide,
   wherein $R^6$ is optionally substituted with one, two, three or four substituents independently selected from the group consisting of: halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
   n=0 to 10; and
   m=0 to 20;
   or an agriculturally acceptable salt thereof.

10. The method of claim 9, wherein said plant is a fruit crop plant or a vegetable crop plant.

11. The method of claim 9, wherein said microbial biofilm formation or microbial infection is caused by a fungi.

12. The method of claim 9, wherein said compound is applied to said plant in an amount effective to treat or control a fungal disease selected from the group consisting of rots, leaf molds, blights, wilts, damping-off, spot, root rot, stem rot, mildew, brown spot, gummosis, melanose, post-bloom fruit drop, scab, alternaria, canker, flyspeck, fruit blotch, dieback, downy mildews, ear rots, anthracnose bunts, smut, rust, eyespot and pecky rice.

13. The method of claim 9, wherein said compound of Formula (II)(a) is a compound of Formula (II)(a)(5)(D):

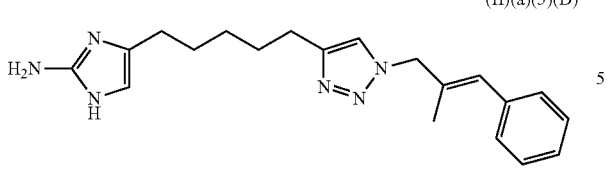

or an agriculturally acceptable salt thereof.

14. A method of enhancing the effects of a microbicide comprising applying a compound of Formula (II)(a):

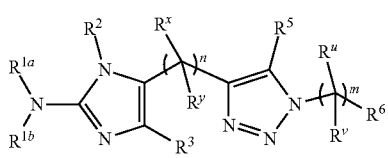

wherein:
$R^{1a}$ and $R^{1b}$ are each H;
$R^2$, $R^3$ and $R^5$ are each independently H or alkyl;
each occurrence of $R^x$, $R^y$, $R^u$ and $R^v$ is present or absent (depending upon chain saturation), and are each independently H or alkyl;
$R^6$ is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, nitro, carboxy, amino acid sidechain, amino acid and peptide,
wherein $R^6$ is optionally substituted with one, two, three or four substituents independently selected from the group consisting of: halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
n=0 to 10; and
m=0 to 20;
or an agriculturally acceptable salt thereof, in combination with said microbicide.

15. The method of claim 14, wherein said microbicide comprises copper.

16. The method of claim 14, wherein said microbicide is an antibiotic or a bacteriophage.

17. The method of claim 14, wherein said compound of Formula (II)(a) is a compound of Formula (II)(a)(5)(D):

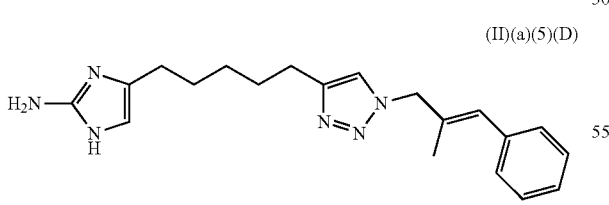

or an agriculturally acceptable salt thereof.

18. A method of enhancing the effects of a plant defense activator comprising applying a compound of Formula (II)(a):

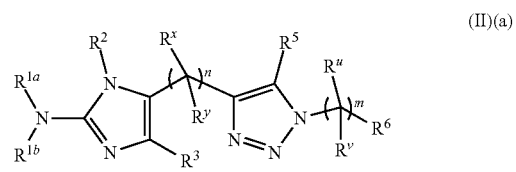

wherein:
$R^{1a}$ and $R^{1b}$ are each H;
$R^2$, $R^3$ and $R^5$ are each independently H or alkyl;
each occurrence of $R^x$, $R^y$, $R^u$ and $R^v$ is present or absent (depending upon chain saturation), and are each independently H or alkyl;
$R^6$ is independently selected from the group consisting of: H, hydroxy, acyl, alkyl, alkenyl, alkynyl, cycloalkyl, heterocyclo, aryl, heteroaryl, alkoxy, amino, amide, thiol, sulfone, sulfoxide, nitro, carboxy, amino acid sidechain, amino acid and peptide,
wherein $R^6$ is optionally substituted with one, two, three or four substituents independently selected from the group consisting of: halo, hydroxy, acyl, alkyl, alkenyl, alkynyl, cycloalkyl, heterocyclo, aryl, heteroaryl, alkoxy, amino, amide, thiol, sulfone, sulfoxide, oxo, oxy, nitro, carbonyl, carboxy, amino acid sidechain, amino acid and peptide;
n=0 to 10; and
m=0 to 20;
or an agriculturally acceptable salt thereof, in combination with said plant defense activator.

19. The method of claim 18, wherein said compound of Formula (II)(a) is a compound of Formula (II)(a)(5)(D):

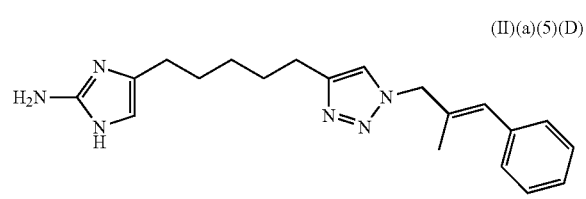 [SMILES: C/C(=C\c1ccccc1)Cn1cc(CCCCCc2c[nH]c(N)n2)nn1]

or an agriculturally acceptable salt thereof.

* * * * *